(12) United States Patent
Blackburn et al.

(10) Patent No.: US 10,183,930 B2
(45) Date of Patent: Jan. 22, 2019

(54) CRYSTALLINE FORMS AND PROCESSES FOR THE PREPARATION OF CANNABINOID RECEPTOR MODULATORS

(71) Applicant: Arena Pharmaceuticals, Inc., San Diego, CA (US)

(72) Inventors: Anthony C. Blackburn, San Diego, CA (US); Sangdon Han, San Diego, CA (US); Robert M. Jones, San Diego, CA (US); Antonio Garrido Montalban, San Diego, CA (US); Biman B. Pal, San Diego, CA (US); Jaimie Karyn Rueter, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 15/248,300

(22) Filed: Aug. 26, 2016

(65) Prior Publication Data

US 2017/0144993 A1 May 25, 2017

Related U.S. Application Data

(62) Division of application No. 14/001,133, filed as application No. PCT/US2012/026506 on Feb. 24, 2012, now Pat. No. 9,458,136.

(60) Provisional application No. 61/446,732, filed on Feb. 25, 2011, provisional application No. 61/448,542, filed on Mar. 2, 2011.

(51) Int. Cl.
 C07D 403/04 (2006.01)
 A61K 31/497 (2006.01)
 A61P 29/00 (2006.01)

(52) U.S. Cl.
 CPC .......... *C07D 403/04* (2013.01); *A61K 31/497* (2013.01); *A61P 29/00* (2018.01); *C07B 2200/13* (2013.01)

(58) Field of Classification Search
 CPC .................................................. C07D 403/04
 See application file for complete search history.

(56) References Cited

U.S. PATENT DOCUMENTS

| 5,977,108 | A | 11/1999 | Kikuchi et al. |
| 6,329,402 | B1 | 12/2001 | Kikuchi et al. |
| 6,541,474 | B2 | 4/2003 | Kikuchi et al. |
| 6,630,463 | B2 | 10/2003 | Kikuchi et al. |
| 6,884,808 | B2 | 4/2005 | Kikuchi et al. |
| 7,741,350 | B1 | 6/2010 | Luo |
| 9,458,136 | B2 | 10/2016 | Blackburn et al. |
| 2010/0160288 | A1 | 6/2010 | Kikuchi et al. |

FOREIGN PATENT DOCUMENTS

| DE | 102004054666 | 5/2006 |
| EP | 0838453 | 4/2005 |
| EP | 1177187 | 7/2007 |
| FR | 2 875 230 | 3/2006 |
| WO | WO 97/02244 | 1/1997 |
| WO | WO 2000/064888 | 11/2000 |
| WO | WO 04/060882 | 7/2004 |
| WO | WO 2005/123677 | 12/2005 |
| WO | WO 2006/025069 | 3/2006 |
| WO | WO 2006/030124 | 3/2006 |
| WO | WO 2006/069242 | 6/2006 |
| WO | WO 06/129178 | 12/2006 |
| WO | WO 2006/129178 | 12/2006 |
| WO | WO 08/003665 | 1/2008 |
| WO | WO 08/039645 | 4/2008 |
| WO | WO 08/048914 | 4/2008 |
| WO | WO 08/053341 | 5/2008 |
| WO | WO 08/063781 | 5/2008 |
| WO | WO 08/064054 | 5/2008 |
| WO | WO 08/079316 | 7/2008 |

(Continued)

OTHER PUBLICATIONS

"PI3K / Akt Cell Signaling," (2010) www.cellsignal.com.

(Continued)

*Primary Examiner* — Andrew D Kosar
*Assistant Examiner* — John S Kenyon
(74) *Attorney, Agent, or Firm* — Fish & Richardson P.C.; Lyle W. Spruce

(57) ABSTRACT

The present invention relates to crystalline forms of (1aS, 5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1) and pharmaceutical compositions thereof that modulate the activity of the cannabinoid $CB_2$ receptor and are therefore useful in the treatment of $CB_2$ receptor-mediated disorders, for example, osteoarthritis; pain; hyperalgesia; allodynia; inflammatory hyperalgesia; neuropathic hyperalgesia; acute nociception; osteoporosis; multiple sclerosis-associated spasticity; autoimmune disorders; allergic reactions; CNS inflammation for example; atherosclerosis; undesired immune cell activity, and inflammation associated with a disorder selected from: osteoarthritis, anaphylaxis, Behcet's disease, graft rejection, vasculitis, gout, spondylitis, viral disease, bacterial disease, lupus, inflammatory bowel disease, autoimmune hepatitis, and type 1 diabetes mellitus; age-related macular degeneration; cough; leukemia; lymphoma; CNS tumors; prostate cancer; Alzheimer's disease; stroke-induced damage; dementia; amyotrophic lateral sclerosis; and Parkinson's disease.

11 Claims, 19 Drawing Sheets

(56) References Cited

FOREIGN PATENT DOCUMENTS

| WO | WO 08/085302 | 7/2008 |
|---|---|---|
| WO | WO 08/109007 | 9/2008 |
| WO | WO 08/119694 | 10/2008 |
| WO | WO 08/157500 | 12/2008 |
| WO | WO 08/157751 | 12/2008 |
| WO | WO 09/009550 | 1/2009 |
| WO | WO 09/015169 | 1/2009 |
| WO | WO 09/025785 | 2/2009 |
| WO | WO 2010/088050 | 8/2010 |
| WO | WO 2012/116277 | 8/2010 |
| WO | WO 2011/025541 | 3/2011 |
| WO | WO 2012/116278 | 8/2012 |
| WO | WO 2012/116279 | 8/2012 |

OTHER PUBLICATIONS

Alexander et al., "Cannabinoids in the treatment of cancer," Cancer Letters, 2009, 285: 6-12.
Anand, et al., (2008) "Cannabinoid Receptor CB2 localisation and Agonist-Mediated Inhibition of Capsaicin Responses in Human Sensory Neurons" Pain doi:10.1016/j.pain.2008.06.007.
Belvisi, et al., (2008) "Inhibitory Activity of the Novel CB2 Receptor Agonist, GW833972A, On Guinea-Pig and Human Sensory Nerve Function in the Airways" British Journal of Pharmacology 1-11.
Bingham, et al., (2007) "Species-specific In Vitro Pharmacological Effects of the Cannabinoid Receptor 2 (CB2) Selective Ligand AM1241 and Its Resolved Enantiomers" British Journal of Pharmacology 151:1061-1070.
Boatman et al., "Potent tricyclic pyrazole tetrazole agonists of the nicotinic acid receptor (GPR109a)," Bioorganic & Medicinal Chemistry Letters, 2010, 20: 2797-2800.
Bouaboula, et al., (1996) "Signaling Pathway Associated With Stimulation of CB2 Peripheral Cannabinoid Receptor" Eur. J. Biochem. 237:704-711.
Caffarel, et al., (2010) "Cannabinoids Reduce ErbB2-Driven Breast Cancer Progression Through Akt Inhibition" Molecular Cancer2010, 9:196 and Supplement.
Carracedo, et al., (2006) "Cannabinoids Induce Apoptosis of Pancreatic Tumor Cells via Endoplasmic Reticulum Stress-Related Genes" Cancer Res 66:6748-6755.
Casanova, et al., (2003) "Inhibition of Skin Tumor Growth and Angiogenesis In Vivo by Activation of Cannabinoid Receptors" J. Clin. Invest. 111 :43--50 doi:10.1172/JC1200316116.
Cheng, et al., (2008) "Discovery and Optimization of a Novel Series of N-Arylamide Oxadiazoles as Potent, Highly Selective and Orally Bioavailable Cannabinoid Receptor 2 (CB2) Agonists" J. Med. Chem. 51 :5019-5034.
Compton, et al., (1992) "Aminoalkylindole Analogs: Cannabimimetic Activity of a Class of Compounds Structurally Distinct from A9-Tetrahydrocannabinols" JPET 263:1118-1126.
Di Marzo, et al., (2006) "Plant, Synthetic, and Endogenous Cannabinoids in Medicine" Annu. Rev. Med. 57:553-74.
Di Mauro, et al., (2008) "Structural Modifications of N-arylamide Oxadiazoles: Identification of N-Arylpiperidine Oxadiazoles as Potent and Selective Agonists of CB2" Bioorganic & Medicinal Chemistry Letters 18:4267-4274.
Diaz, et al., (2008) "Design and Synthesis of a Novel Series of N-Alkyl Isatin Acylhydrazone Derivatives that Act as Selective Cannabinoid Receptor 2 Agonists for the Treatment of Neuropathic Pain" J. Med. Chem., 51 :4932-4947.
Ermann, et al., (2008) "Arylsulfonamide CB2 receptor agonists: SAR and Optimization of CB2 selectivity" Bioorganic & Medicinal Chemistry Letters 18:1725-1729.
Galiegue, et al., (1995) "Expression of Central and Peripheral Cannabinoid Receptors in Human Immune Tissues and Leukocyte Subpopulations" Eur. J. Biochem. 232:54-61.
Giblin, et al., (2007) "Discovery of 2-[(2,4-Dichlorophenyl(amino]-N-[(tetrahydro- 2H-pyran-4yl)methyl]-4-(trifluoromethyl)-5-pyrimidinecarboxamide, a Selective CB2 Receptor Agonist for the Treatment of Inflammatory Pain" J. Med. Chem. 50:2597-2600.
Goodman, et al., (2009) "CB2 selective Sulfamoyl Benzamides: Optimization of the Amide Functionality" Bioorganic & Medicinal Chemistry Letters 19:309-313.
Graham, et al., (2009) "Cannabinoid Receptors: A Brief History and What's Hot" Frontiers in Bioscience 14:944-957.
Hanus, et al., (1999) "HU-308: A Specific Agonist for CB2, A Peripheral Cannabinoid Receptor" PNAS 96: 14228-14233.
Hosohata, et al., (1997) "AM630 Antagonism of Cannabinoid-Stimulated [35S]GTP yS Binding in the Mouse Brain" European Journal of Pharmacology 321: R1-R3.
Khan, Mohammad Najmul Ghani; Khazaain al Advia, 1911, p. 886. w/ English translation.
Khan, Mohammad Najmul Ghani; Khazaain al Advia, 1911, p. 887. w/ English translation.
Khan, Mohammad Najmul Ghani; Khazaain al Advia, 1911, p. 889. w/ English translation.
Kikuch, et al., (2008) "Pharmacological Evaluation of a Novel Cannabinoid 2 (CB2) Ligand, PF-03550096, In Vitro and In Vivo by Using a Rat Model of Visceral Hypersensitivity" J Phannacol Sci 1 06:219-224.
Ibn-e-Sina, Abu Ali; Al Qaanoon ti/ Tibb, 1987, p. 327. w/ English translation.
Lozano-Ondoua, et al., (2010) "A Cannabinoid 2 Receptor Agonist Attenuates Bone Cancer-Induced Pain and Bone Loss" Life Sciences 86:646-653.
Majoosi, Ali Ibn-e-Abbass, Kaamil-al-Sena'ah, 2005, p. 303 / English translation.
Maresz, et al., (2007) "Direct Suppression of CNS Autoimmune Inflammation Via The Cannabinoid Receptor CB1 on Neurons and CB2 on Autoreactive T Cells" Nature Medicine 13:492-497.
Markt, et al., (2009) "Discovery of Novel CB2 Receptor Ligands by a Pharmacophore-Based Virtual Screening Workflow" J. Med. Chem. 52:369-378.
Marx, et al., (2009) "Discovery of a.-Amidosulfones as Potent and Selective Agonists of CB2: Synthesis, SAR, and Pharmacokinetic Properties" Bioorganic & Medicinal Chemistry Letters 19:31-35.
McKallip, et al., (2002) "Targeting CB2 Cannabinoid Receptors as a Novel Therapy to Treat Malignant Lymphoblastic Disease" Blood 100:627-634.
Michalski, et al., (2008) "Cannabinoids in Pancreatic Cancer: Correlation With Survival and Pain" Int J Cancer. 122:742-750.
Mitchell, et al., (2009) "Pyridine-3-carboxamides as Novel CB2 Agonists for Analgesia" Bioorganic & Medicinal Chemistry Letters 19:259-263.
Munro, et al., (1993) "Molecular Characterization of a Peripheral Receptor for Cannabinoids" Nature • 365:61-65.
Naguib, et al., (2008) "MDA7: A Novel Selective Agonist for CB2 Receptors That Prevents Allodynia in Rat Neuropathic Pain Models" British Journal of Pharmacology 1-13.
Narayanan, et al., (2006) "GRC 10622: A Novel Orally Active CB2 Receptor Agonist With Potential Anti-Hyperalgesic Effects", poster submitted at Society for Neuroscience—Oct. 14-18, 2006, Atlanta, Georoia, USA.
Nunez, et al., (2004) "Cannabinoid CB2 Receptors Are Expressed by Perivascular Microglial Cells in the Human Brain: An Immunohistochemical Study" Synapse 53:208-213.
Ofek, et al., (2006) "Peripheral Cannabinoid Receptor, CB2, Regulates Bone Mass" PNAS 103:696-701.
Ohta, et al., (2007) "N-Alkylidenearylcarboxamides as New Potent and Selective CB2 Cannabinoid Receptor Agonists With Good Oral Bioavailability" Bioorganic & Medicinal Chemistry Letters 17:6299-6304.
Ohta, et al., (2008) "Imine Derivatives as New Potent and Selective CB2 Cannabinoid Receptor Agonists With an Analgesic Action" Bioorganic & Medicinal Chemistry 16:1111-1124.
Olea-Herrero, et al., (2009) "Inhibition of Human Tumour Prostate PC-3 cell growth by Cannabinoids R(+)-Methanandamide and JWH-015: Involvement of CB2" British Journal of Cancer 101 :940-950.

(56) References Cited

OTHER PUBLICATIONS

Omura, et al., (2008) "The SAR Studies of Novel CB2 Selective Agonists, Benzimidazolone Derivatives" Bioorganic & Medicinal Chemistry Letters doi: 10.1016/j.bmc1.2008.04.032.

Page, et al., (2007) "New 1,2,3,4-Tetrahydropyrrolo[3,4-b]indole Derivatives as Selective CB2 Receptor Agonists" Bioorganic & Medicinal Chemistry Letters 17:6183-6187.

Page, et al., (2008) "Novel Benzimidazole Derivatives as Selective CB2 Agonists" Bioorganic & Medicinal Chemistry Letters 18:3695-3700.

Palazuelos, et al, (2008) "The CB2 Cannabinoid Receptor Controls Myeloid Progenitor Trafficking" http://www.jbc.org/cgi/doi/10.1074/jbc. M707960200.

Pasquini, et al., (2008) "Investigations on the 4-Quinolone-3-carboxylic Acid Motif 2. Synthesis and Structure#Activity Relationship of Potent and Selective Cannabinoid-2 Receptor Agonists Endowed with Analgesic Activity in Vivo" J. Med. Chem. 51:5075-5084.

Pisanti, et al., (2009) "Use of Cannabinoid Receptor Agonists in Cancer Therapy as Palliative and Curative Agents" Best Practice & Research Clinical Endocrinology & Metabolism 23:117-131.

Preet, et al., (2010) "Cannabinoid Receptors, CB1 and CB2, as Novel Targets for Inhibition of Non-Small Cell Lung Cancer Growth and Metastasis" Published OnlineFirst on Nov. 19, 201 o as 10.1158/1940-6207.CAPR-10-0181.

Rinaldi-Carmona, et al, (1998) "SR 144528, the First Potent and Selective Antagonist of the CB2 Cannabinoid Receptor" JPET 284:644-650.

Sanchez, et al., (2001) "Inhibition of Glioma Growth in Vivo by Selective Activation of the CB2 Cannabinoid Receptor" Cancer Research 61:5784-5789.

Sharma, et al., (2010) "Cell Line-Based Platforms to Evaluate the Therapeutic Efficacy of Candidate Anticancer Agents" Nature Reviews I Cancer 10:241-253.

Shi et al., (2008) "Cannabinoid 2 Receptor Induction by IL-12 and Its Potential as a Therapeutic Target for the Treatment of Anaplastic Thyroid Carcinoma" Cancer Gene Therapy 15:101-107.

Slipetz, et al., (1995) "Activation of the Human Peripheral Cannabinoid Recepto Results in Inhibition of Adenylyl Cyclase" Molecular Pharmacology, 48:352-361.

Stansfield, et al., (2007) "Development of Carboxylic Acid Replacements in Indole-N-acetamide Inhibitors of Hepatitis C Virus NS5B Polymerase" Bioorganic & Medicinal Chemistry Letters 17:5143-5149.

Valenzano, et al, (2003) "Pharmacological and Pharmacokinetic Characterization of the Cannabinoid Receptor 2 Agonist, GW405833, Utilizing Rodent Models of Acute and Chronic Pain, Anxiety, Ataxia and Catalepsy" Neuropharmacology 48:658-672.

Van Sickle, et al., (2005) "Identification and Functional Characterization of Brainstem Cannabinoid CB2 Receptors" Science 310:329.

Verbist, et al., (2008) "5-Sulfonyl-benzimidazoles as Selective CB2 Agonists" Bioorganic & Medicinal Chemistry Letters 18:2574-2579.

Whiteside, et al., (2007) "The Role of the Cannabinoid CB2 Receptor in Pain Transmission and Therapeutic Potential of Small Molecule CB2 Receptor Agonists" Current Medicinal Chemistry, 14:917-936.

Worm, et al., (2008) "Sulfamoyl Benzamides as Novel CB2 Cannabinoid Receptor Ligands" Bioorganic & Medicinal Chemistry Letters 18:2830-2835.

Wotherspoon, et al., (2005) "Peripheral Nerve Injury Induces Cannabinoid Receptor 2 Protein Expression in Rat Sensory Neurons" Neuroscience 135:235-245.

Yao, et al., (2008) "Characterization of a Cannabinoid CB2 Receptor Selective Agonist, A-836339, in In Vitro Pharmacological assays and In Vivo Pain Models" JPET Fast Forward. Published on Oct. 17, 2008 as 001:10.1124/jpet.108.145011.

Yao, et al., (2008) "In Vitro and In Vivo Characterization of A-796260: A Selective Cannabinoid CB2 Receptor Agonist Exhibiting Analgesic Activity in Rodent Pain Models" British Journal of Pharmacology 1 53:390-401.

Zindell, et al., (2009) "Morpholine Containing CB2 Selective Agonists" Bioorganic & Medicinal Chemistry Letters doi: 10.1016/j.bmc1.2009.02.033.

DSC and TGA Thermograms of Compound 1 (Anhydrous Form)

CRYSTALLINE FORMS AND PROCESSES FOR THE PREPARATION OF CANNABINOID RECEPTOR MODULATORS

CROSS-REFERENCE TO RELATED APPLICATIONS

This is a divisional of U.S. patent application Ser. No. 14/001,133, filed Dec. 16, 2013, now U.S. Pat. No. 9,458,136, which is a 35 U.S.C. § 371 National Stage Application of International Application No. PCT/US2012/026506, filed Feb. 24, 2012, which claims priority to U.S. Provisional Application Nos. 61/448,542, filed Mar. 2, 2011, and 61/446,732, filed Feb. 25, 2011. The entire content of each of these applications is hereby incorporated herein by reference.

FIELD OF THE INVENTION

The present invention relates to crystalline forms of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1) and pharmaceutical compositions thereof that modulate the activity of the cannabinoid $CB_2$ receptor and are therefore useful in the treatment of $CB_2$ receptor-mediated disorders, for example, osteoarthritis; pain, for example bone and joint pain, muscle pain, dental pain, migraine and other headache pain, inflammatory pain, neuropathic pain, pain that occurs as an adverse effect of therapeutics, and pain associated with a disorder selected from: osteoarthritis, cancer, multiple sclerosis, allergic reactions, nephritic syndrome, scleroderma, thyroiditis, diabetic neuropathy, fibromyalgia, HIV related-neuropathy, sciatica, and autoimmune conditions; hyperalgesia; allodynia; inflammatory hyperalgesia; neuropathic hyperalgesia; acute nociception; osteoporosis; multiple sclerosis-associated spasticity; autoimmune disorders, for example an autoimmune disorder selected from the group consisting of: multiple sclerosis, Guillan-Barré syndrome, polyradiculoneuropathy, chronic inflammatory demyelination, rheumatoid arthritis, psoriatic arthritis, ankylosing spondylarthritis, and reactive arthritis; allergic reactions, for example, an allergic reaction associated with a disorder selected from: atopic dermatitis, pruritis, urticaria, asthma, conjunctivitis, allergic rhinitis, and anaphylaxis; CNS inflammation for example, CNS inflammation associated with a disorder selected from: Alzheimer's disease, stroke, dementia, amyotrophic lateral sclerosis, and human immunodeficiency virus; atherosclerosis; undesired immune cell activity, and inflammation associated with a disorder selected from: osteoarthritis, anaphylaxis, Behcet's disease, graft rejection, vasculitis, gout, spondylitis, viral disease, bacterial disease, lupus, inflammatory bowel disease, autoimmune hepatitis, and type 1 diabetes mellitus; age-related macular degeneration; cough; leukemia; lymphoma; CNS tumors; prostate cancer; Alzheimer's disease; stroke-induced damage; dementia; amyotrophic lateral sclerosis, and Parkinson's disease. The present invention further relates to processes and intermediates useful in the preparation crystalline forms and solvates of Compound 1 and pharmaceutical compositions thereof.

BACKGROUND OF THE INVENTION

Cannabinoids are a group of extracellular signaling molecules that are found in both plants and animals. Signals from these molecules are mediated in animals by two G-protein coupled receptors, Cannabinoid Receptor 1 ($CB_1$) and Cannabinoid Receptor 2 ($CB_2$). $CB_1$ is expressed most abundantly in the neurons of the CNS but is also present at lower concentrations in a variety of peripheral tissues and cells (Matsuda, L. A. et al. (1990) Nature 346:561-564). In contrast, $CB_2$ is expressed predominantly, although not exclusively, in non-neural tissues, e.g. in hematopoietic cells, endothelial cells, osteoblasts, osteoclasts, the endocrine pancreas, and cancerous cell lines (Munro, S. et al. (1993) Nature 365:61-65; and as reviewed in Pacher, P. et al. (2006) Pharmacol. Rev. 58(3): 389-462). As such, $CB_1$ is believed to be primarily responsible for mediating the psychotropic effects of cannabinoids on the body, whereas $CB_2$ is believed to be primarily responsible for most of their non-neural effects.

SUMMARY OF THE INVENTION

One aspect of the present invention relates to crystalline forms of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1):

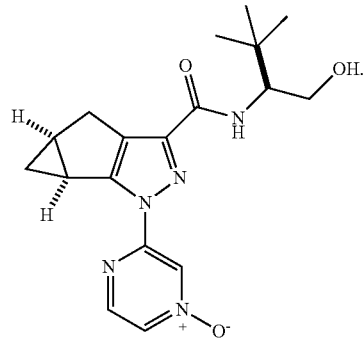

One aspect of the present invention relates to an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1).

One aspect of the present invention relates to processes for preparing an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide comprising the steps of:

1) crystallizing (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide from a crystallizing mixture to obtain a crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide in the crystallizing mixture, wherein the crystallizing mixture comprises acetonitrile and water; and
2) isolating the crystalline form of (1aS,5aS)-2-(4-oxypyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide from the crystallizing mixture to obtain the anhydrous crystalline form of (1aS,5aS)-2-(4-oxy-pyrazin-2-yl)-1a,2,5, 5a-tetrahydro-1H-2,3-diaza-cyclopropa[a]pentalene-4-carboxylic acid ((S)-1-hydroxymethyl-2,2-dimethyl-propyl)-amide.

One aspect of the present invention relates to an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide prepared by a process as described herein.

One aspect of the present invention relates to compositions comprising an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein.

One aspect of the present invention relates to compositions comprising an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein, and a pharmaceutically acceptable carrier.

One aspect of the present invention relates to processes of making a composition comprising mixing an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein, with a pharmaceutically acceptable carrier.

One aspect of the present invention relates to methods for the treatment of a cannabinoid receptor-mediated disorder in an individual, comprising administering to the individual in need thereof, a therapeutically effective amount of an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein or a pharmaceutical composition thereof.

One aspect of the present invention relates to methods for the treatment of a $CB_2$ receptor-mediated disorder in an individual, comprising administering to the individual in need thereof, a therapeutically effective amount of an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein or a pharmaceutical composition thereof.

One aspect of the present invention relates to the use of an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein, in the manufacture of a medicament for the treatment of a cannabinoid receptor-mediated disorder.

One aspect of the present invention relates to the use of an anhydrous crystalline form of (1 aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein, in the manufacture of a medicament for the treatment of a $CB_2$ receptor-mediated disorder.

One aspect of the present invention relates to an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein, for use in a method of treatment of the human or animal body by therapy.

One aspect of the present invention relates to an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-anide as described herein, for use in a method of treatment of a cannabinoid receptor-mediated disorder.

One aspect of the present invention relates to an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein, for use in a method of treatment of a $CB_2$ receptor-mediated disorder.

One aspect of the present invention relates to acetone solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

One aspect of the present invention relates to non-selective solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

One aspect of the present invention relates to ethyl acetate solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

Certain modulators of the cannabinoid receptor are described in PCT application PCT/US2010/002360, filed 27 Aug. 2010 (International Publication Number WO2011/025541), and in U.S. provisional applications 61/275,506, 61/396,588, and 61/400,146, each of which is incorporated herein by reference in its entirety.

These and other aspects of the invention disclosed herein will be set forth in greater detail as the patent disclosure proceeds.

DETAILED DESCRIPTION OF THE INVENTION

Definitions

Figure 1:
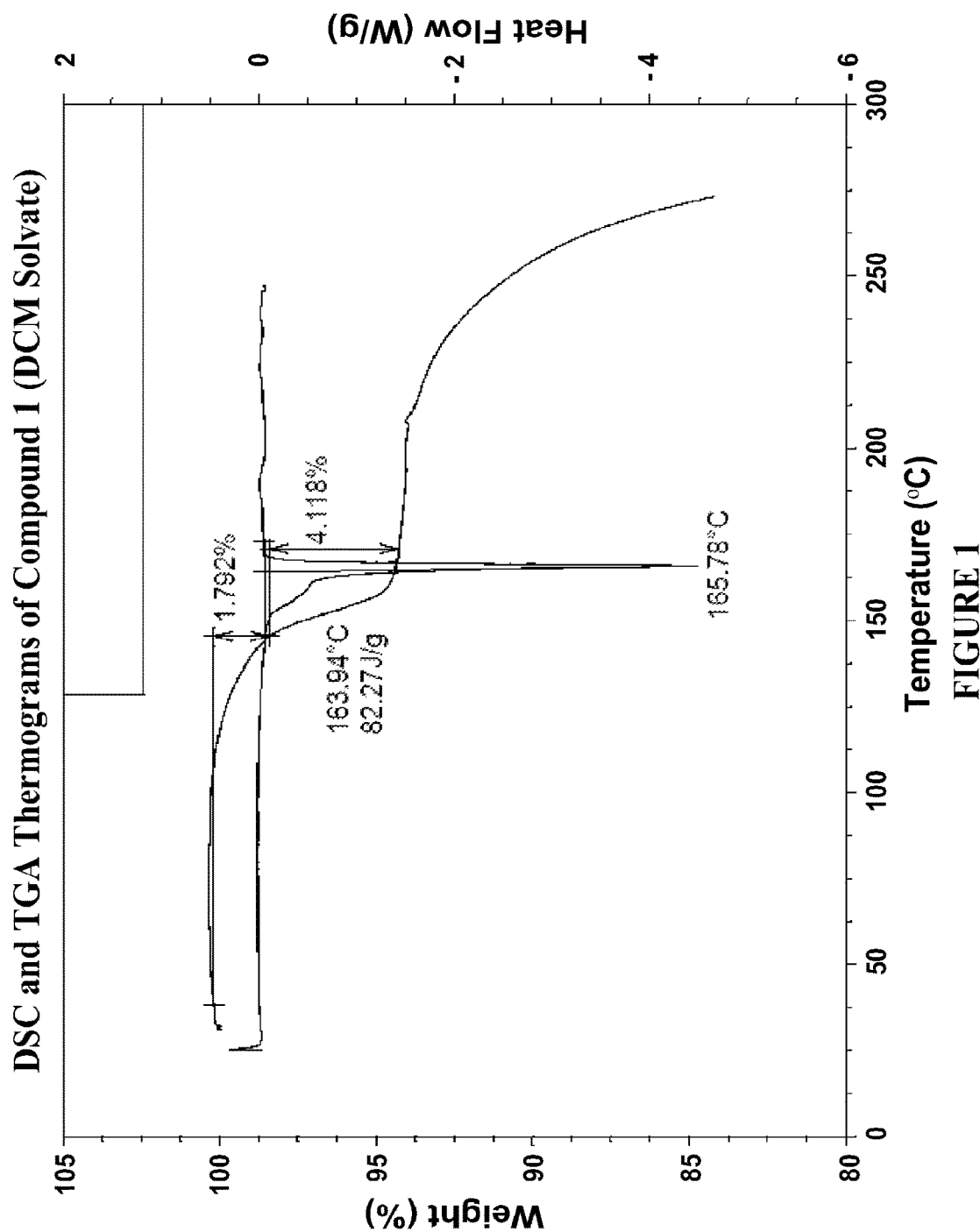
FIG. 1 shows a differential scanning calorimetry (DSC) thermogram for a sample containing a crystalline form of Compound 1 ($CH_2Cl_2$ solvate) and a thermogravimetric analysis (TGA) thermogram of a sample containing a crystalline form of Compound 1 ($CH_2Cl_2$ solvate).

For clarity and consistency, the following definitions will be used throughout this patent document.

The term "agonist" refers to a moiety that interacts with and activates a G-protein-coupled receptor, for instance a cannabinoid receptor, and can thereby initiate a physiological or pharmacological response characteristic of that receptor. For example, an agonist may activate an intracellular response upon binding to a receptor, or enhance GTP binding to a membrane.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" refers to any animal, including mammals, preferably mice, rats, other rodents, rabbits, dogs, cats, swine, cattle, sheep, horses, or primates, and most preferably humans.

The term "modulate or modulating" refers to an increase or decrease in the amount, quality, response or effect of a particular activity, function or molecule.

The term "composition" refers to a compound or crystalline form thereof, including but not limited to, salts, solvates, and hydrates of a compound of the present invention, in combination with at least one additional component, such as, a composition obtained/prepared during synthesis, pre-formulation, in-process testing (i.e., TLC, HPLC, NMR samples), and the like The term "pharmaceutical composition" refers to a specific composition comprising at least one active ingredient; including but not limited to, salts, solvates, and hydrates of compounds of the present invention, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "therapeutically effective amount" refers to the amount of active compound or pharmaceutical agent that elicits the biological or medicinal response in a tissue, system, animal, individual or human that is being sought by a researcher, veterinarian, medical doctor or other clinician or caregiver or by an individual, which includes one or more of the following:

(1) Preventing the disease, for example, preventing a disease, condition or disorder in an individual that may be predisposed to the disease, condition or disorder but does not yet experience or display the pathology or symptomatology of the disease;

(2) Inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease, for example, ameliorating a disease, condition or disorder in an individual that is experiencing or displaying the pathology or symptomatology of the disease, condition or disorder (i.e., reversing the pathology and/or symptomatology).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. In addition, subcombinations of uses and medical indications listed in the embodiments describing such uses and medical indications described herein, are also specifically embraced by the present invention just as if each and every subcombination of uses and medical indications was individually and explicitly recited herein.

Processes of the Invention

The present invention is directed to, inter alia, processes useful in the preparation of an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, a modulator of the cannabinoid $CB_2$ receptor.

One aspect of the present invention relates to processes for preparing an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide comprising the steps of:

1) crystallizing (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide from a crystallizing mixture to obtain a crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide in the crystallizing mixture, wherein the crystallizing mixture comprises acetonitrile and water; and 2) isolating the crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide from the crystallizing mixture to obtain the anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

In some embodiments, crystallizing is conducted at a temperature of about −10° C. to about 35° C. In some embodiments, crystallizing is conducted at a temperature of about −10° C. to about 25° C. In some embodiments, crystallizing is conducted at a temperature of about −10° C. to about 10° C. In some embodiments, crystallizing is conducted at a temperature of about −5° C. to about 5° C.

In some embodiments, the crystallizing mixture is prepared by the steps of:

1) dissolving (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide in acetonitrile and a first amount of water to form a first mixture; and 2) adding a second amount of water to the first mixture to obtain the crystallizing mixture. In some embodiments, dissolving is conducted at a temperature of about 25° C. to about 80° C. In some embodiments, dissolving is conducted at a temperature of about 40° C. to about 70° C. In some embodiments, dissolving is conducted at a temperature of about 55° C. to about 65° C. In some embodiments, dissolving is conducted at a temperature of about 58° C. to about 62° C. In some embodiments, dissolving is conducted at a temperature of about 60° C. In some embodiments, the molar ratio present in the first mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and first amount water is about 1.0:7.3:30.0 to about 1.0:12.1:49.6. In some embodiments, the molar ratio present in the first mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and first amount water is about 1.0:7.8:31.8 to about 1.0:11.6:47.6. In some embodiments, the molar ratio present in the first mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and first amount water is about 1.0:8.2:33.7 to about 1.0:11.2:45.7. In some embodiments, the molar ratio present in the first mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and first amount water is about 1.0:8.7:35.7 to about 1.0:10.7:43.7. In some embodiments, the molar ratio present in the first mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and first amount water is about 1.0:9.2:37.0 to about 1.0:10.2:41.7. In some embodiments, the molar ratio present in the first mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and first amount water is about 1.0:9.7:39.7. In some embodiments, adding of the second amount of water to the first mixture is conducted at a rate that the temperature of the mixture of the second amount of water together with the first mixture is at about 25° C. to about 80° C. In some embodiments, adding of the second amount of water to the first mixture is conducted at a rate that the temperature of the mixture of the second amount of water together with the first mixture is at about 40° C. to about 70° C. In some embodiments, adding of the second amount of water to the first mixture is conducted at a rate that the temperature of the mixture of the second amount of water together with the first mixture is at about 55° C. to about 65° C. In some embodiments, adding of the second amount of water to the first mixture is conducted at a rate that the temperature of the mixture of the second amount of water together with the first mixture is at about 58° C. to about 62° C. In some embodiments, adding of the second amount of water to the first mixture is conducted at a rate that the temperature of the mixture of the second amount of water together with the first mixture is at about 60° C.

In some embodiments, the molar ratio present in the crystallizing mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and water is about 1.0:7.3:327.4 to about 1.0:12.1:545.6. In some embodiments, the molar ratio present in the crystallizing mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and water in the crystallizing mixture is about 1.0:7.8:349.2 to about 1.0:11.6:523.8. In some embodiments, the molar ratio present in the crystallizing mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and water in the crystallizing mixture is about 1.0:8.2:371.0 to about 1.0:11.2:502.0. In some embodiments, the molar ratio present in the crystallizing mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and water in the crystallizing mixture is about 1.0:8.7:392.8 to about 1.0:10.7:480.1. In some embodiments, the molar ratio present in the crystallizing mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and water in the crystallizing mixture is about 1.0:9.2:414.7 to about 1.0:10.2:458.3. In some embodiments, the molar ratio present in the crystallizing mixture between (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, acetonitrile, and water in the crystallizing mixture is about 1.0:9.7:436.5.

In some embodiments, (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide in the crystallizing and dissolving steps is selected from the group consisting of:

1) a dichloromethane solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide;

2) an acetone solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide;

3) a non-selective solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; and 4) an ethyl acetate solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; and mixtures thereof.

In some embodiments, (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide prior to the dissolving step is selected from the group consisting of:

1) a dichloromethane solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide;

2) an acetone solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide;

3) a non-selective solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; and 4) an ethyl acetate solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; and mixtures thereof.

In some embodiments, isolating comprises filtering the crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide from the crystallizing mixture.

In some embodiments, isolating comprises removing the crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide from the crystallizing mixture.

One aspect of the present invention relates to processes for preparing an anhydrous crystalline form, the processes further comprise the step of drying the crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide to obtain the anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide. In some embodiments, drying is conducted at a temperature of about 15° C. to about 80° C. In some embodiments, drying is conducted at a temperature of about 25° C. to about 65° C. In some embodiments, drying is conducted at a temperature of about 35° C. to about 55° C. In some embodiments, drying is conducted at a temperature of about 50° C. In some embodiments, drying is conducted at a pressure of less than 760 mm Hg and a temperature of about 35° C. to about 55° C. In some embodiments, drying is conducted at a pressure of less than 760 mm Hg and a temperature of about 55° C. to about 65° C.

In some embodiments, after isolating, the anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide has a chemical purity of about 95% or greater. In some embodiments, after isolating, the anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide has a chemical purity of about 98% or greater. In some embodiments, after isolating, the anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide has a chemical purity of about 99% or greater. In some embodiments, after isolating, the anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide has an enantiomeric excess of about 95% or greater. In some embodiments, after isolating, the anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide has an enantiomeric excess of about 98% or greater. In some embodiments, after isolating, the anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide has an enantiomeric excess of about 99% or greater. In some embodiments, after isolating, the anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide has a chemical purity of about 99% or greater and an enantiomeric excess of about 99% or greater.

One aspect of the present invention relates to an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide prepared by a process described herein.

One aspect of the present invention relates to processes of making a composition comprising mixing an anhydrous crystalline form of (1aS,5aS)-2-(4-oxy-pyrazin-2-yl)-1a,2,5, 5a-tetrahydro-1H-2,3-diaza-cyclopropa[a]pentalene-4-carboxylic acid ((S)-1-hydroxymethyl-2,2-dimethyl-propyl)-amide as described herein with a pharmaceutically acceptable carrier.

One aspect of the present invention relates to processes of making a composition further comprising forming the composition into drug product, such as, a tablet, a pill, a powder, a lozenge, a sachet, a cachet, an elixir, a suspension, an emulsion, a solution, a syrup, a soft gelatin capsule, a hard gelatin capsule, a suppository, a sterile injectable solution, or a sterile packaged powder.

Crystalline Forms of Compound 1

One aspect of the present invention relates to anhydrous and solvate forms of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1).

One aspect of the present invention relates to DCM solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1).

One aspect of the present invention relates to an anhydrous form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1).

One aspect of the present invention relates to acetone solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-anide (Compound 1).

One aspect of the present invention relates to non-selective solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1).

One aspect of the present invention relates to ethyl acetate solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1).

Crystalline forms of the solvates and anhydrous forms described herein can be identified by their unique solid state signature with respect to, for example, differential scanning calorimetry (DSC), powder X-ray diffraction (PXRD), and other solid state methods.

Further characterization with respect to water or solvent content of crystalline forms can be gauged by any of the following methods for example, thermogravimetric analysis (TGA), DSC and the like.

For DSC, it is known that the temperatures observed will depend upon sample purity, the rate of temperature change, as well as sample preparation technique and the particular instrument employed. Thus, the values reported herein relating to DSC thermograms can vary by plus or minus about 4° C. (i.e., ±4° C.). The values reported herein relating to DSC thermograms can also vary by plus or minus about 20 joules per gram (i.e., ±20 joules/gram).

In some embodiments, the DSC thermogram values reported herein relate to desolvation events. When DSC thermogram values reported herein relate to desolvation events, the values reported herein are estimates. Scan rate and pan closure can influence DSC values for desolvation events, which can vary by plus or minus about 25° C. (i.e., ±25° C.). DSC values for desolvation events reported herein were recorded using a sample in an aluminum pan with an uncrimped lid and a scan rate of 10° C./min.

For PXRD, the relative intensities of the peaks can vary, depending upon the sample preparation technique, the sample mounting procedure and the particular instrument employed. Moreover, instrument variation and other factors can often affect the 2θ values. Therefore, the peak assignments of diffraction patterns can vary by plus or minus 0.2°2θ (i.e., ±0.2°2θ).

For TGA, the features reported herein can vary by plus or minus about 5° C. (i.e., ±5° C.). The TGA features reported herein can also vary by plus or minus about 2% (i.e., ±2%) weight change due to, for example, sample variation.

Further characterization with respect to hygroscopicity of the crystalline forms can be gauged by, for example, dynamic moisture sorption (DMS). The DMS features reported herein can vary by plus or minus about 5% (i.e., ±5%) relative humidity. The DMS features reported herein can also vary by plus or minus about 5% (i.e., ±5%) weight change.

1. Dichloromethane (DCM) Solvates of Compound 1.

A. Compound 1 (DCM Solvates)

One aspect of the present invention relates to DCM solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1). The DCM solvates of Compound 1 are characterized by PXRD. The physical properties for the DCM solvates as determined by PXRD are summarized in Table 1 below.

TABLE 1

Figure 2:
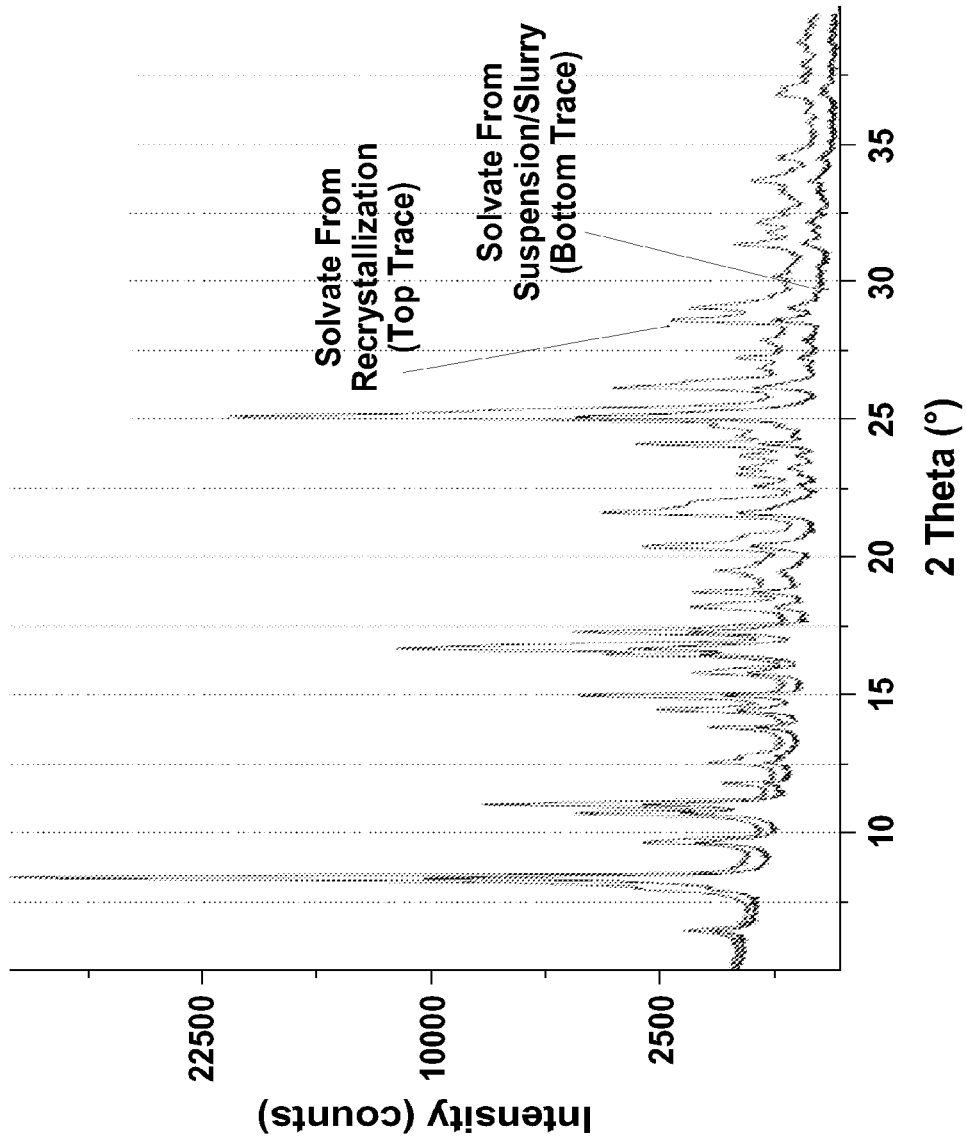
FIG. 2 shows an overlay of a powder X-ray diffraction (PXRD) pattern for a sample containing a crystalline form of Compound 1 ($CH_2Cl_2$ solvate) obtained from recrystallization using $CH_2Cl_2$/hexane (Top Trace) and a powder X-ray diffraction (PXRD) pattern for a sample containing a crystalline form of Compound 1 ($CH_2Cl_2$ solvate) obtained by slurrying non-solvated Compound 1 in $CH_2Cl_2$ (Bottom Trace). The PXRD showed the crystalline solvate obtained from the $CH_2Cl_2$ slurry is substantially indistinguishable from the crystalline solvate resulting from $CH_2Cl_2$/hexane recrystallization.

| Compound 1 (DCM solvates) | |
|---|---|
| PXRD | FIG. 2: Peaks of about ≥9.7% relative intensity at 8.3, 9.6, 10.7, 11.0, 15.0, 16.5, 16.7, 17.3, and 25.1 °2θ |

The amount of DCM present in these solvates can vary, and be up to about 10.6% by weight. The amount of DCM can readily be determined by TGA. The physical properties for a DCM solvate from Example 1, Method 1, Step F are summarized in Table 2 below.

TABLE 2

| Compound 1 (DCM solvates, Example 1, Method 1, Step F) | |
|---|---|
| TGA | FIG. 1: Decrease in weight of about 5.9% out to about 150° C. |
| DSC | FIG. 1: Endotherm extrapolated onset temperature: about 163° C. |

Certain powder X-ray diffraction peaks for the DCM solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1) are shown in Table 3 below.

TABLE 3

| Pos. [°2θ] | d-spacing [Å] | Rel. Int. [%] |
|---|---|---|
| 6.4 | 13.8 | 6.1 |
| 8.3 | 10.6 | 100.0 |
| 9.6 | 9.2 | 11.3 |
| 10.7 | 8.3 | 15.6 |
| 11.0 | 8.0 | 24.3 |
| 11.8 | 7.5 | 2.2 |
| 12.5 | 7.1 | 2.7 |

TABLE 3-continued

| Pos. [°2θ.] | d-spacing [Å] | Rel. Int. [%] |
|---|---|---|
| 13.8 | 6.4 | 4.5 |
| 14.4 | 6.1 | 7.3 |
| 15.0 | 5.9 | 9.7 |
| 15.8 | 5.6 | 6.0 |
| 16.5 | 5.4 | 13.9 |
| 16.7 | 5.3 | 30.2 |
| 17.3 | 5.1 | 16.5 |
| 18.2 | 4.9 | 2.6 |
| 18.7 | 4.7 | 5.6 |
| 19.5 | 4.6 | 2.3 |
| 20.4 | 4.4 | 6.1 |
| 21.6 | 4.1 | 7.7 |
| 24.1 | 3.7 | 5.3 |
| 25.1 | 3.5 | 46.0 |
| 26.1 | 3.4 | 6.3 |
| 28.6 | 3.1 | 4.3 |
| 29.1 | 3.1 | 2.6 |

B. Dichloromethane Hemi-Solvate of Compound 1

Figure 3:
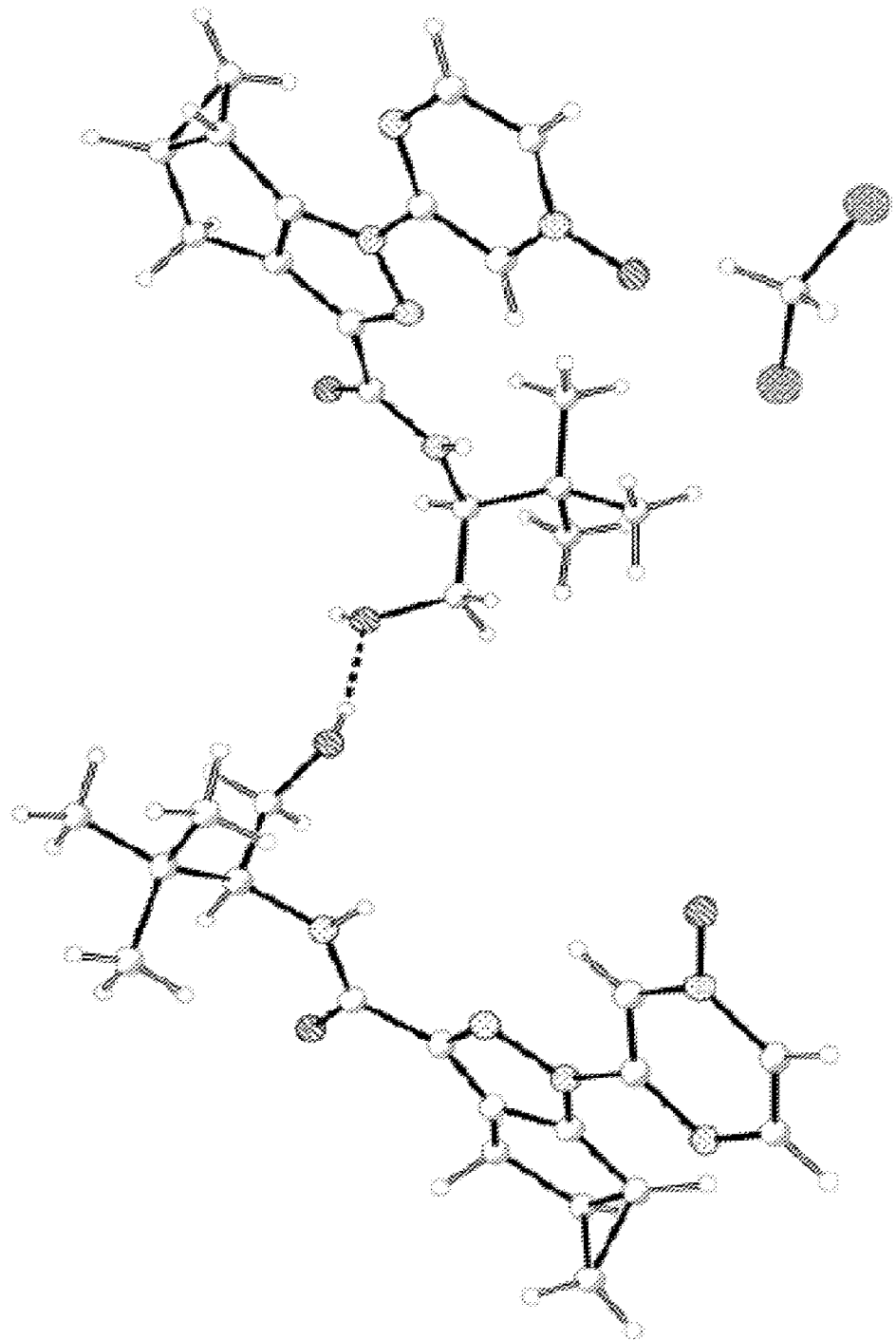
FIG. 3 shows the asymmetric unit for the hemi-$CH_2Cl_2$ solvate of Compound 1 based on single-crystal X-ray diffraction analysis.

One aspect of the present invention relates to the DCM hemi-solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1). The DCM hemi-solvate of Compound 1 was prepared by slow crystallization from CH$_2$Cl$_2$ and hexanes (Example 2). The crystal structure was solved and is shown in FIG. 3.

2. Compound 1 (Anhydrous Form).

One aspect of the present invention relates to an anhydrous form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1). The physical properties of the crystalline form of Compound 1 (anhydrous form) are summarized in Table 4 below.

TABLE 4

Figure 6:
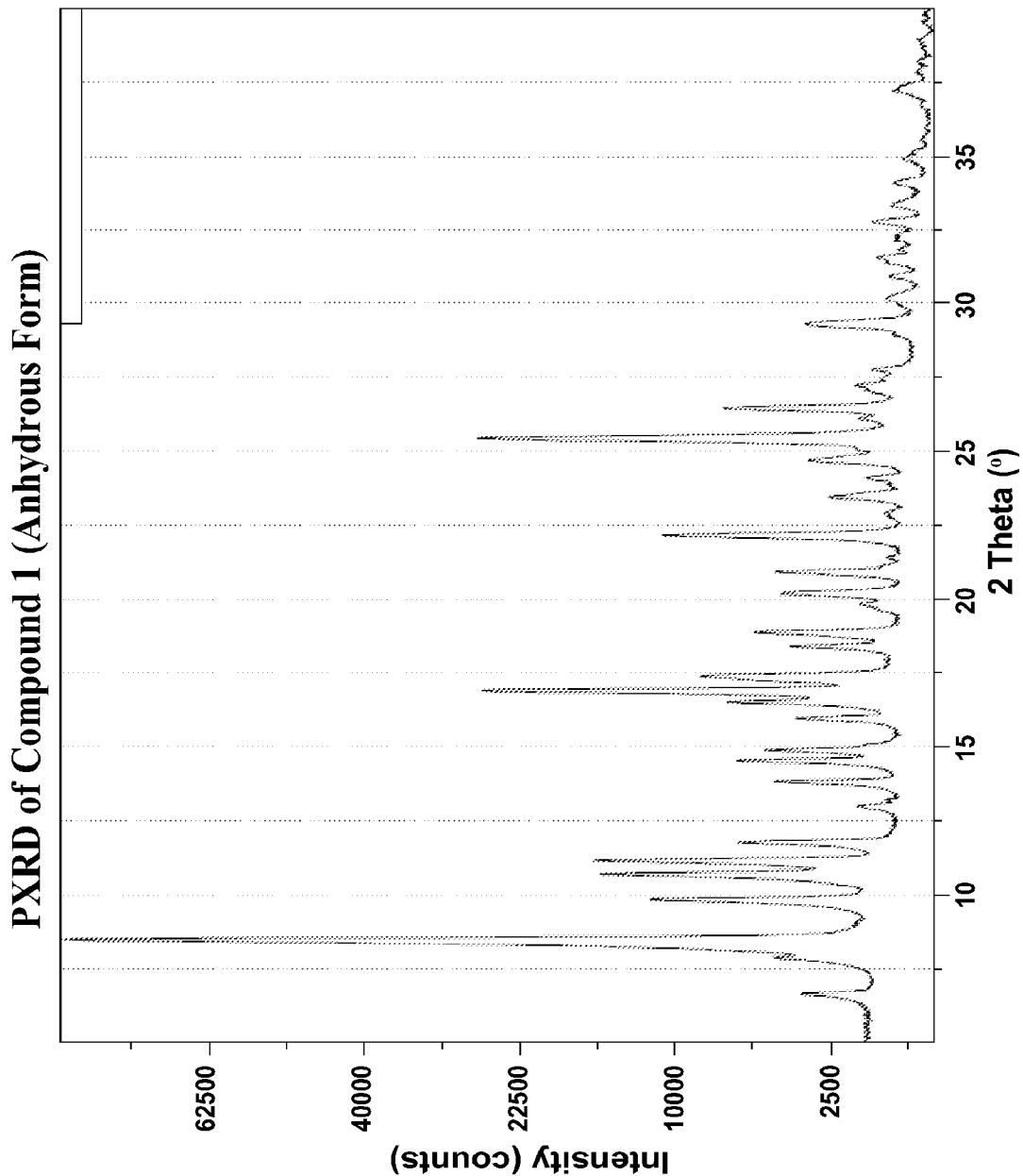
FIG. 6 shows a powder X-ray diffraction (PXRD) pattern for a sample containing an anhydrous crystalline form of Compound 1.

| Compound 1 (Anhydrous Form) | |
|---|---|
| PXRD | FIG. 6: Peaks of about ≥8.7% relative intensity at 8.5, 9.8, 10.7, 11.1, 11.8, 14.5, 16.5, 16.9, 17.4, 18.9, 22.1, and 25.4 °2θ |
| TGA | FIG. 7: Decrease in weight of about 0.24% out to about 150° C. |
| DSC | FIG. 7: Endotherm extrapolated onset temperature: about 162° C. |
| DMS | FIG. 7A: The adsorption/desorption isotherm shows about 1.0% or less weight change from about 10% relative humidity (RH) to about 90% RH; and about 0.1% or less weight change after a 10% RH to 90% RH back to 10% RH cycle, See Example 13. |

Certain powder X-ray diffraction peaks for the anhydrous form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1) are shown in Table 5 below.

TABLE 5

| Pos. [°2θ.] | d-spacing [Å] | Rel. Int. [%] |
|---|---|---|
| 6.6 | 13.4 | 4.4 |
| 7.9 | 11.3 | 5.5 |
| 8.5 | 10.5 | 100.0 |
| 9.8 | 9.0 | 21.5 |
| 10.7 | 8.3 | 28.3 |
| 11.1 | 7.9 | 26.1 |
| 11.8 | 7.5 | 10.0 |

TABLE 5-continued

| Pos. [°2θ.] | d-spacing [Å] | Rel. Int. [%] |
|---|---|---|
| 13.8 | 6.4 | 7.5 |
| 14.5 | 6.1 | 11.3 |
| 14.9 | 6.0 | 6.0 |
| 16.0 | 5.6 | 5.8 |
| 16.5 | 5.4 | 11.8 |
| 16.9 | 5.2 | 26.7 |
| 17.3 | 5.1 | 8.5 |
| 17.4 | 5.1 | 14.8 |
| 18.4 | 4.8 | 4.6 |
| 18.9 | 4.7 | 8.7 |
| 20.2 | 4.4 | 5.5 |
| 20.9 | 4.3 | 4.4 |
| 22.1 | 4.0 | 14.5 |
| 23.4 | 3.8 | 3.0 |
| 24.7 | 3.6 | 4.6 |
| 25.4 | 3.5 | 26.6 |
| 26.5 | 3.4 | 8.1 |
| 29.2 | 3.1 | 2.8 |
| 29.3 | 3.0 | 3.6 |

One aspect of the present invention relates to an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

One aspect of the present invention relates to an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide, wherein the anhydrous crystalline form has a powder X-ray diffraction pattern comprising a peak, in terms of 2θ, at 8.5°±0.2°. In some embodiments, the anhydrous crystalline form has a powder X-ray diffraction pattern comprising peaks, in terms of 2θ, at 8.5°±0.2°, and 10.7°±0.2°. In some embodiments, the anhydrous crystalline form has a powder X-ray diffraction pattern comprising peaks, in terms of 2θ, at 8.5°±0.2°, 10.7°±0.2°, and 16.9°±0.2°. In some embodiments, the anhydrous crystalline form has a powder X-ray diffraction pattern comprising peaks, in terms of 2θ, at 8.5°±0.2°, 10.7°±0.2°, 16.9°±0.2°, 25.4°±0.2°, and 11.1°±0.2°. In some embodiments, the anhydrous crystalline form has a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, and 17.4°±0.2°. In some embodiments, the anhydrous crystalline form has a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, 17.4°±0.2°, 22.1°±0.2°, and 16.5°±0.2°. In some embodiments, the anhydrous crystalline form has a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, 17.4°±0.2°, 22.1°±0.2°, 16.5°±0.2°, 14.5°±0.2°, 11.8°±0.2°, and 18.9°±0.2°. In some embodiments, the anhydrous crystalline form has a powder X-ray diffraction pattern substantially as shown in FIG. 6, wherein by "substantially" is meant that the reported peaks can vary by about ±0.2°2θ.

Figure 7:
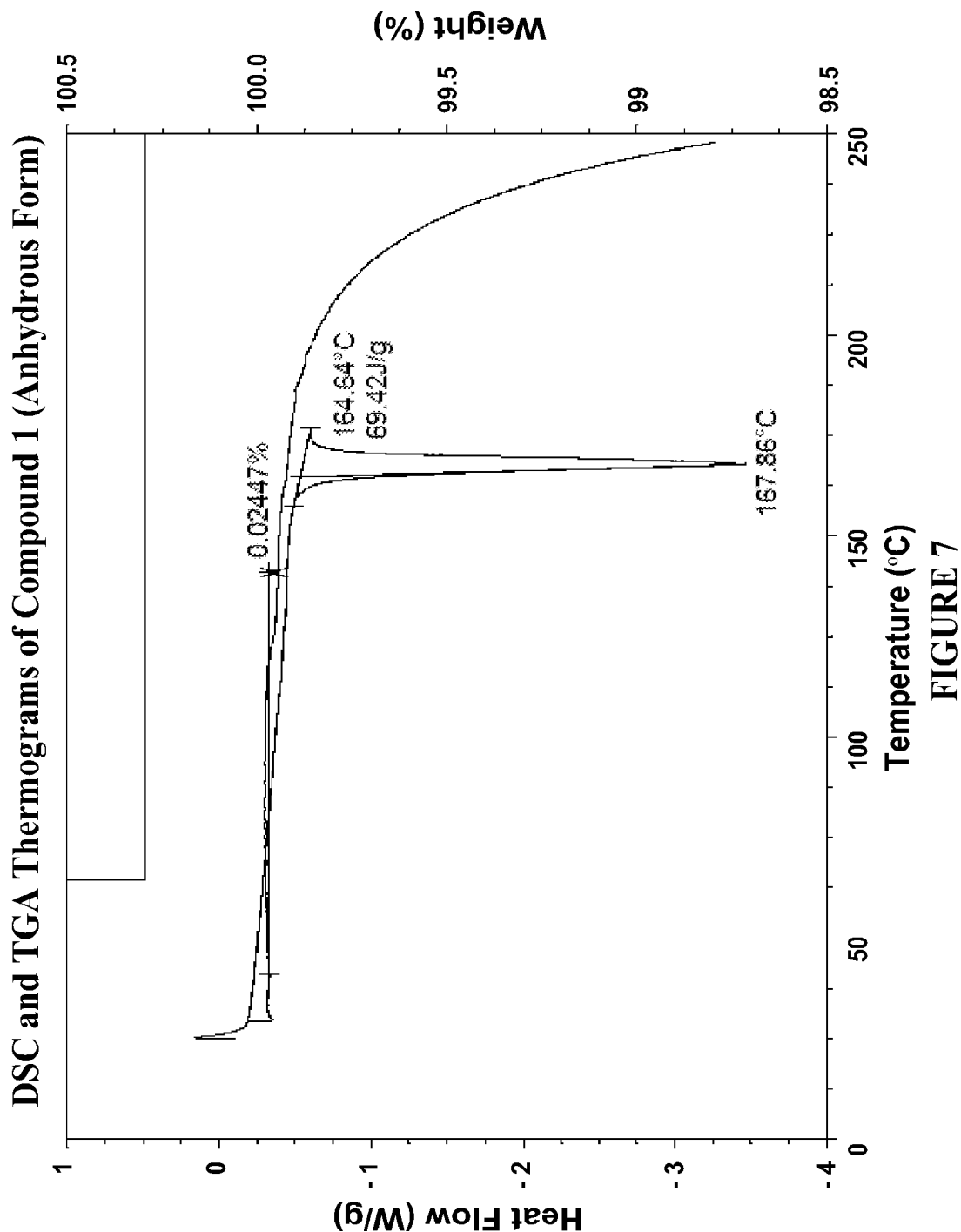
FIG. 7 shows a differential scanning calorimetry (DSC) thermogram for a sample containing anhydrous crystalline form of Compound 1 and a thermogravimetric analysis (TGA) thermogram of a sample containing anhydrous crystalline form of Compound 1.

In some embodiments, the anhydrous crystalline form has a differential scanning calorimetry thermogram comprising an endotherm with an extrapolated onset temperature between about 159.6° C. and about 169.6° C. In some embodiments, the anhydrous crystalline form has a differential scanning calorimetry thermogram comprising an endotherm with an extrapolated onset temperature between about 160.6° C. and about 168.6° C. In some embodiments, the anhydrous crystalline form has a differential scanning calorimetry thermogram comprising an endotherm with an extrapolated onset temperature between about 162.6° C. and about 166.6° C. In some embodiments, the anhydrous crystalline form has having a differential scanning calorimetry thermogram comprising an endotherm with an extrapolated onset temperature between about 163.6° C. and about 165.6° C. In some embodiments, the anhydrous crystalline form has a differential scanning calorimetry thermogram comprising an endotherm with an extrapolated onset temperature at about 164.6° C. In some embodiments, the anhydrous crystalline form has a differential scanning calorimetry thermogram substantially as shown in FIG. 7, wherein by "substantially" is meant that the reported DSC features can vary by about ±4° C. and that the reported DSC features can vary by about ±20 joules per gram.

In some embodiments, the anhydrous crystalline form has a thermogravimetric analysis profile showing about 0.5% weight loss below about 135° C. In some embodiments, the anhydrous crystalline form has a thermogravimetric analysis profile showing about 0.25% weight loss below about 135° C. In some embodiments, the anhydrous crystalline form has a thermogravimetric analysis profile showing about 0.05% weight loss below about 135° C. In some embodiments, the anhydrous crystalline form has a thermogravimetric analysis profile substantially as shown in FIG. 7, wherein by "substantially" is meant that the reported TGA features can vary by about ±5° C., and that that the reported TGA features can vary by about ±2% weight change.

One aspect of the present invention relates to the anhydrous crystalline form having:

1) a powder X-ray diffraction pattern comprising peaks, in terms of 2θ, at 8.5°±0.2°, and 10.7°±0.2°;

2) a differential scanning calorimetry thermogram comprising an endotherm with an extrapolated onset temperature between about 159.6° C. and about 169.6° C.; and/or 3) a thermogravimetric analysis profile showing about 0.5% weight loss below about 135° C.

One aspect of the present invention relates to the anhydrous crystalline form having:

1) a powder X-ray diffraction pattern comprising peaks, in terms of 2θ, at 8.5°±0.2°, 10.7°±0.2°, and 16.9°±0.2°;

2) a differential scanning calorimetry thermogram comprising an endotherm with an extrapolated onset temperature between about 160.6° C. and about 168.6° C.; and/or 3) a thermogravimetric analysis profile showing about 0.25% weight loss below about 135° C.

One aspect of the present invention relates to the anhydrous crystalline form having:

1) a powder X-ray diffraction pattern comprising peaks, in terms of 2θ, at 8.5°±0.2°, 10.7°±0.2°, 16.9°±0.2°, 25.4°±0.2°, and 11.1°±0.2°;

2) a differential scanning calorimetry thermogram comprising an endotherm with an extrapolated onset temperature between about 162.6° C. and about 166.6° C.; and/or 3) a thermogravimetric analysis profile showing about 0.05% weight loss below about 135° C.

One aspect of the present invention relates to the anhydrous crystalline form having:

1) a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, and 17.4°±0.2°;

2) a differential scanning calorimetry thermogram comprising an endotherm with an extrapolated onset temperature between about 163.6° C. and about 165.6° C.; and/or 3) a thermogravimetric analysis profile showing about 0.05% weight loss below about 135° C.

One aspect of the present invention relates to the anhydrous crystalline form having:

1) a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, 17.4°±0.2°, 22.1°±0.2°, and 16.5°±0.2°;

2) a differential scanning calorimetry thermogram comprising an endotherm with an extrapolated onset temperature at about 164.6° C.; and/or 3) a thermogravimetric analysis profile showing about 0.05% weight loss below about 135° C.

One aspect of the present invention relates to the anhydrous crystalline form having:

1) a powder X-ray diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, 17.4°±0.2°, 22.1°±0.2°, 16.5°±0.2°, 14.5°±0.2°, 11.8°±0.2°, and 18.9°±0.2°;

2) a differential scanning calorimetry thermogram comprising an endotherm with an extrapolated onset temperature at about 164.6° C.; and/or 3) a thermogravimetric analysis profile showing about 0.05% weight loss below about 135° C.

One aspect of the present invention relates to the anhydrous crystalline form having:

1) a powder X-ray diffraction pattern substantially as shown in FIG. 6;

2) a differential scanning calorimetry thermogram substantially as shown in FIG. 7; and/or 3) a thermogravimetric analysis profile substantially as shown in FIG. 7.

3. Compound 1 (Acetone Solvates).

One aspect of the present invention relates to acetone solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1). The acetone solvates of Compound 1 are characterized by PXRD. The physical properties for the acetone solvates as determined by PXRD are summarized in Table 6 below.

TABLE 6

Figure 8:
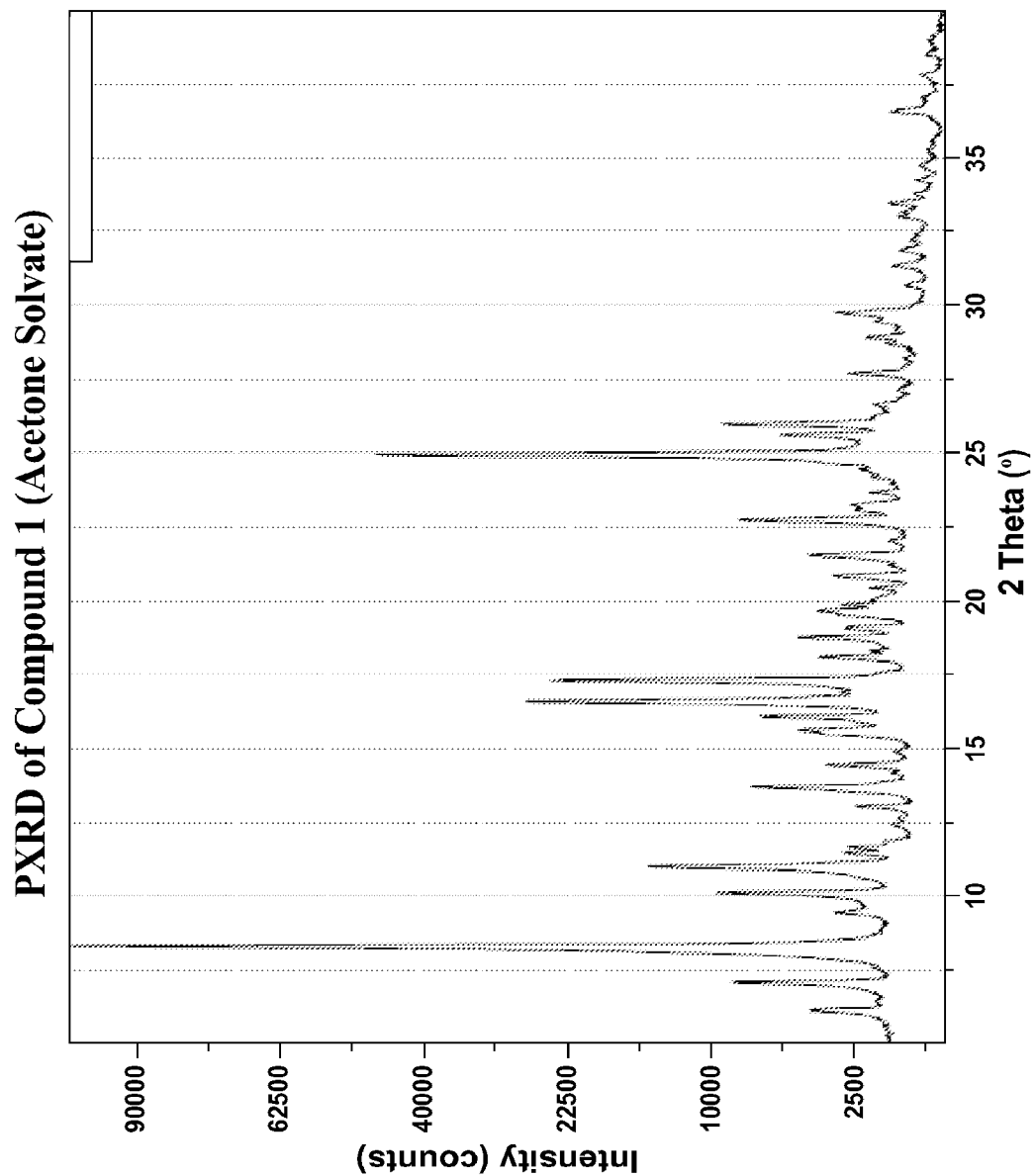
FIG. 8 shows a powder X-ray diffraction (PXRD) pattern for a sample containing a crystalline form of Compound 1 (acetone solvate).

| Compound 1 (Acetone Solvate) |
| --- |
| PXRD FIG. 8: Peaks of about ≥5.4% relative intensity at 7.1, 8.3, 10.1, 11.0, 13.7, 16.1, 16.6, 17.3, 22.7, 25.0, 25.6, and 26.0 °2θ |

The amount of acetone present in these solvates can vary and can readily be determined by TGA. The physical properties for a acetone solvate from Example 5 are summarized in Table 7 below.

TABLE 7

Figure 9:
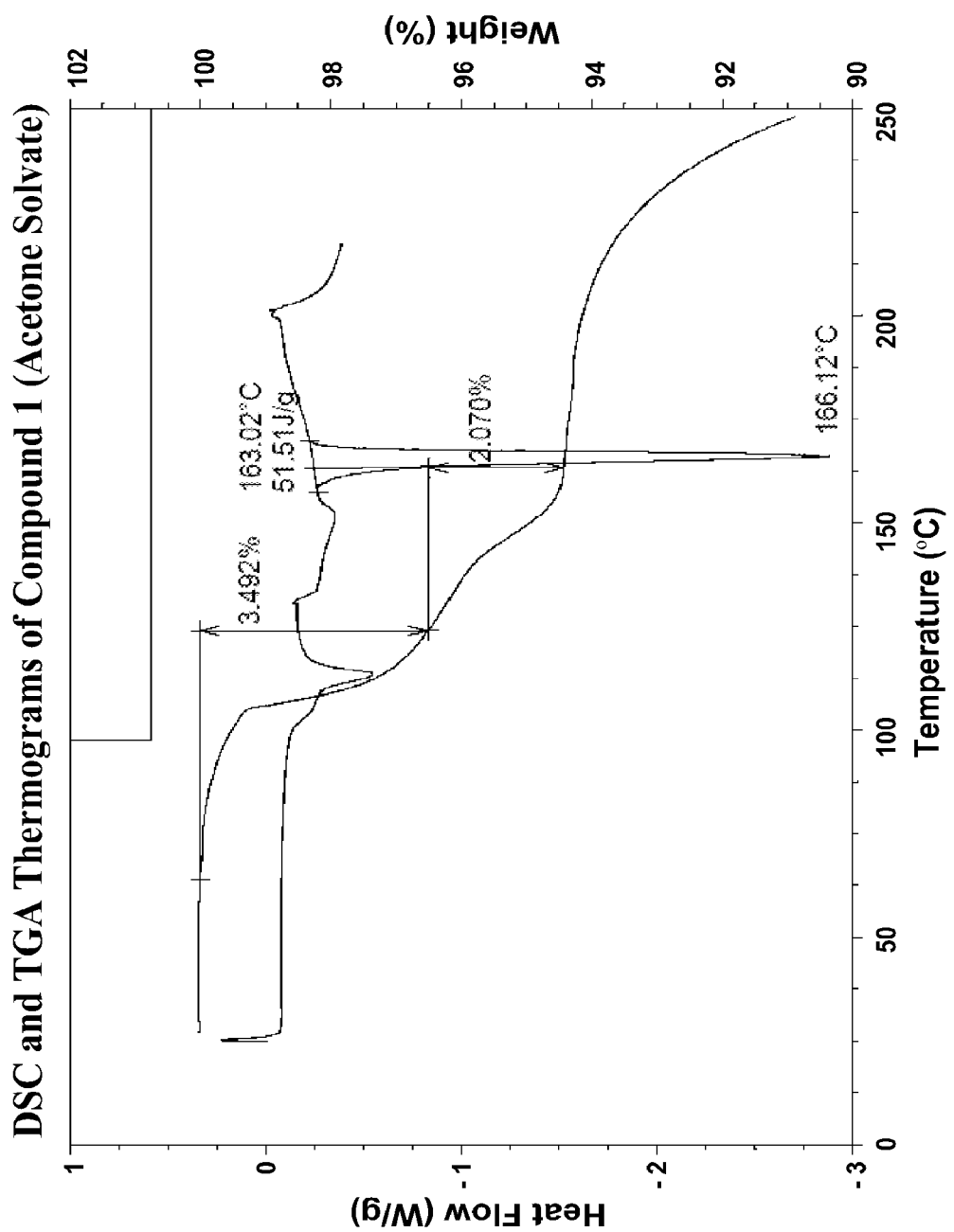
FIG. 9 shows a differential scanning calorimetry (DSC) thermogram for a sample containing a crystalline form of Compound 1 (acetone solvate) and a thermogravimetric analysis (TGA) thermogram of a sample containing a crystalline form of Compound 1 (acetone solvate).

| Compound 1 (Acetone Solvate, Example 5) |
| --- |
| TGA FIG. 9: Decrease in weight of about 5.5% out to about 150° C. |
| DSC FIG. 9: Endotherm extrapolated onset temperature: about 163° C. |

Certain powder X-ray diffraction peaks for the acetone solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1) are shown in Table 8 below.

TABLE 8

| Pos. [°2θ.] | d-spacing [Å] | Rel. Int. [%] |
|---|---|---|
| 8.3 | 10.6266 | 100.0 |
| 25.0 | 3.56844 | 45.0 |
| 16.6 | 5.34216 | 26.2 |
| 17.3 | 5.1231 | 23.5 |
| 11.0 | 8.04494 | 14.4 |
| 10.1 | 8.74974 | 9.2 |
| 26.0 | 3.4277 | 8.8 |
| 7.1 | 12.45547 | 8.3 |
| 22.7 | 3.91113 | 7.7 |
| 13.7 | 6.46525 | 6.9 |
| 16.1 | 5.51282 | 6.3 |
| 25.6 | 3.47777 | 5.4 |
| 18.8 | 4.72926 | 4.5 |
| 15.6 | 5.67632 | 4.4 |
| 21.5 | 4.12408 | 3.9 |
| 6.1 | 14.41073 | 3.8 |
| 18.1 | 4.90385 | 3.5 |
| 19.7 | 4.51452 | 3.5 |
| 15.5 | 5.72733 | 3.3 |
| 14.4 | 6.13613 | 3.2 |
| 24.7 | 3.61152 | 3.1 |
| 20.8 | 4.26245 | 2.9 |
| 9.5 | 9.35087 | 2.8 |
| 29.8 | 3.00222 | 2.8 |
| 19.5 | 4.54403 | 2.8 |
| 19.9 | 4.4696 | 2.6 |
| 16.9 | 5.24284 | 2.6 |
| 11.5 | 7.71311 | 2.5 |
| 19.1 | 4.65159 | 2.4 |
| 27.7 | 3.22211 | 2.3 |

One aspect of the present invention relates to an acetone solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

One aspect of the present invention relates to an acetone solvate having a powder X-ray diffraction pattern comprising a peak, in terms of 2θ, at 8.3°±0.2°. In some embodiments, the acetone solvate has a powder X-ray diffraction pattern comprising peaks, in terms of 2θ, at 8.3°±0.2° and 25.0°±0.2°. In some embodiments, the acetone solvate has a powder X-ray diffraction pattern comprising peaks, in terms of 2θ, at 8.3°±0.2°, 25.0°±0.2°, and 16.6°±0.2°. In some embodiments, the acetone solvate has a powder X-ray diffraction pattern comprising peaks, in terms of 2θ, at 8.3°±0.2°, 25.0°±0.2°, 16.6°±0.2°, 17.3°±0.2°, and 11.0°±0.2°. In some embodiments, the acetone solvate has a powder X-ray diffraction pattern comprising peaks, in terms of 2θ, at 8.3°±0.2°, 25.0°±0.2°, 16.6°±0.2°, 17.3°±0.2°, 11.0°±0.2°, 10.1°±0.2°, and 26.0°±0.2°. In some embodiments, the acetone solvate has a powder X-ray diffraction pattern comprising peaks, in terms of 2θ, at 8.3°±0.2°, 25.0°±0.2°, 16.6°±0.2°, 17.3°±0.2°, 11.0°±0.2°, 10.1°±0.2°, 26.0°±0.2°, 7.1°±0.2°, and 22.7°±0.2°. In some embodiments, the acetone solvate has a powder X-ray diffraction pattern comprising peaks, in terms of 2θ, at 8.3°±0.2°, 25.0°±0.2°, 16.6°±0.2°, 17.3°±0.2°, 11.0°±0.2°, 10.1°±0.2°, 26.0°±0.2°, 7.1°±0.2°, 22.7°±0.2°, 13.7°±0.2°, 16.1°±0.2°, and 25.6°±0.2°. In some embodiments, the acetone solvate has a powder X-ray diffraction pattern substantially as shown in FIG. 8, wherein by "substantially" is meant that the reported peaks can vary by about ±0.2°2θ.

In some embodiments, the acetone solvate has a differential scanning calorimetry thermogram comprising an endotherm with an extrapolated onset temperature between about 158.0° C. and about 168.0° C. In some embodiments, the acetone solvate has a differential scanning calorimetry thermogram comprising an endotherm with an extrapolated onset temperature between about 159.0° C. and about 167.0° C. In some embodiments, the acetone solvate has a differential scanning calorimetry thermogram comprising an endotherm with an extrapolated onset temperature between about 161.0° C. and about 165.0° C. In some embodiments, the acetone solvate has a differential scanning calorimetry thermogram comprising an endotherm with an extrapolated onset temperature between about 162.0° C. and about 163.0° C. In some embodiments, the acetone solvate has a differential scanning calorimetry thermogram comprising an endotherm with an extrapolated onset temperature at about 163.0° C. In some embodiments, the acetone solvate has a differential scanning calorimetry thermogram substantially as shown in FIG. 9, wherein by "substantially" is meant that the reported DSC features can vary by about ±4° C. and that the reported DSC features can vary by about ±20 joules per gram.

In some embodiments, the acetone solvate has a thermogravimetric analysis profile showing about 6.0% weight loss below about 150° C. In some embodiments, the acetone solvate has a thermogravimetric analysis profile showing about 5.75% weight loss below about 150° C. In some embodiments, the acetone solvate has a thermogravimetric analysis profile showing about 5.5% weight loss or less below about 150° C. In some embodiments, the acetone solvate has a thermogravimetric analysis profile substantially as shown in FIG. 9, wherein by "substantially" is meant that the reported TGA features can vary by about ±5° C., and that that the reported TGA features can vary by about ±2% weight change.

One aspect of the present invention relates to the acetone solvate having:
1) a powder X-ray diffraction pattern comprising peaks, in terms of 2θ, at 8.3°±0.2° and 25.0°±0.2°; and/or
2) a differential scanning calorimetry thermogram comprising an endotherm with an extrapolated onset temperature between about 158.0° C. and about 168.0° C.

One aspect of the present invention relates to the acetone solvate having:
1) a powder X-ray diffraction pattern comprising peaks, in terms of 2θ, at 8.3°±0.2°, 25.0°±0.2°, and 16.6°±0.2°; and/or
2) a differential scanning calorimetry thermogram comprising an endotherm with an extrapolated onset temperature between about 159.0° C. and about 167.0° C.

One aspect of the present invention relates to the acetone solvate having:
1) a powder X-ray diffraction pattern comprising peaks, in terms of 2θ, at 8.3°±0.2°, 25.0°±0.2°, 16.6°±0.2°, 17.3°±0.2°, and 11.0°±0.2°; and/or
2) a differential scanning calorimetry thermogram comprising an endotherm with an extrapolated onset temperature between about 161.0° C. and about 165.0° C.

One aspect of the present invention relates to the acetone solvate having:
1) a powder X-ray diffraction pattern comprising peaks, in terms of 2θ, at 8.3°±0.2°, 25.0°±0.2°, 16.6°±0.2°, 17.3°±0.2°, 11.0°±0.2°, 10.1°±0.2°, and 26.0°±0.2°;
2) a differential scanning calorimetry thermogram comprising an endotherm with an extrapolated onset temperature between about 162.0° C. and about 163.0° C.; and/or
3) a thermogravimetric analysis profile showing about 6.0% weight loss or less below about 150° C.

One aspect of the present invention relates to the acetone solvate having:

1) a powder X-ray diffraction pattern comprising peaks, in terms of 2θ, at 8.3±0.20, 25.0°±0.2°, 16.6°±0.2°, 17.3°±0.2°, 11.0°±0.2°, 10.1°±0.2°, 26.0°±0.2°, 7.1°±0.20, and 22.7°±0.2°;

2) a differential scanning calorimetry thermogram comprising an endotherm with an extrapolated onset temperature at about 163.0° C.; and/or 3) a thermogravimetric analysis profile showing about 5.75% weight loss below about 150° C.

One aspect of the present invention relates to the acetone solvate having:

1) a powder X-ray diffraction pattern comprising peaks, in terms of 2θ, at 8.3°±0.2°, 25.0°±0.2°, 16.6°±0.2°, 17.3°±0.2°, 11.0°±0.2°, 10.1°±0.2°, 26.0°±0.2°, 7.1°±0.2°, 22.7°±0.2°, 13.7°±0.2°, 16.1°±0.2°, and 25.6°±0.2°;

2) a differential scanning calorimetry thermogram comprising an endotherm with an extrapolated onset temperature at about 163.0° C.; and/or 3) a thermogravimetric analysis profile showing about 5.5% weight loss or less below about 150° C.

One aspect of the present invention relates to the acetone solvate having:

1) a powder X-ray diffraction pattern substantially as shown in FIG. 8;

2) a differential scanning calorimetry thermogram substantially as shown in FIG. 9; and/or 3) a thermogravimetric analysis profile substantially as shown in FIG. 9.

4. Compound 1 (Non-Selective Solvates).

One aspect of the present invention relates to non-selective solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1). Non-selective solvates refer to solvates that have substantially the same crystalline form as determined by PXRD, and depending on the purity, after de-solvation will have similar extrapolated onset temperature (+/−4.0° C.) as determined by DSC regardless what solvent or solvents were used to prepare the solvate. It is understood that the TGA trace will vary from one non-selective solvate to another and is primarily determined by the solvent used in the preparation, the solvate formed, and the amount of the solvnet present in the solvate.

The non-selective solvates of Compound 1 are characterized by PXRD. The physical properties for the non-selective solvates as determined by PXRD are summarized in Table 9 below.

TABLE 9

Compound 1 (Non-Selective Solvate)

Figure 10:
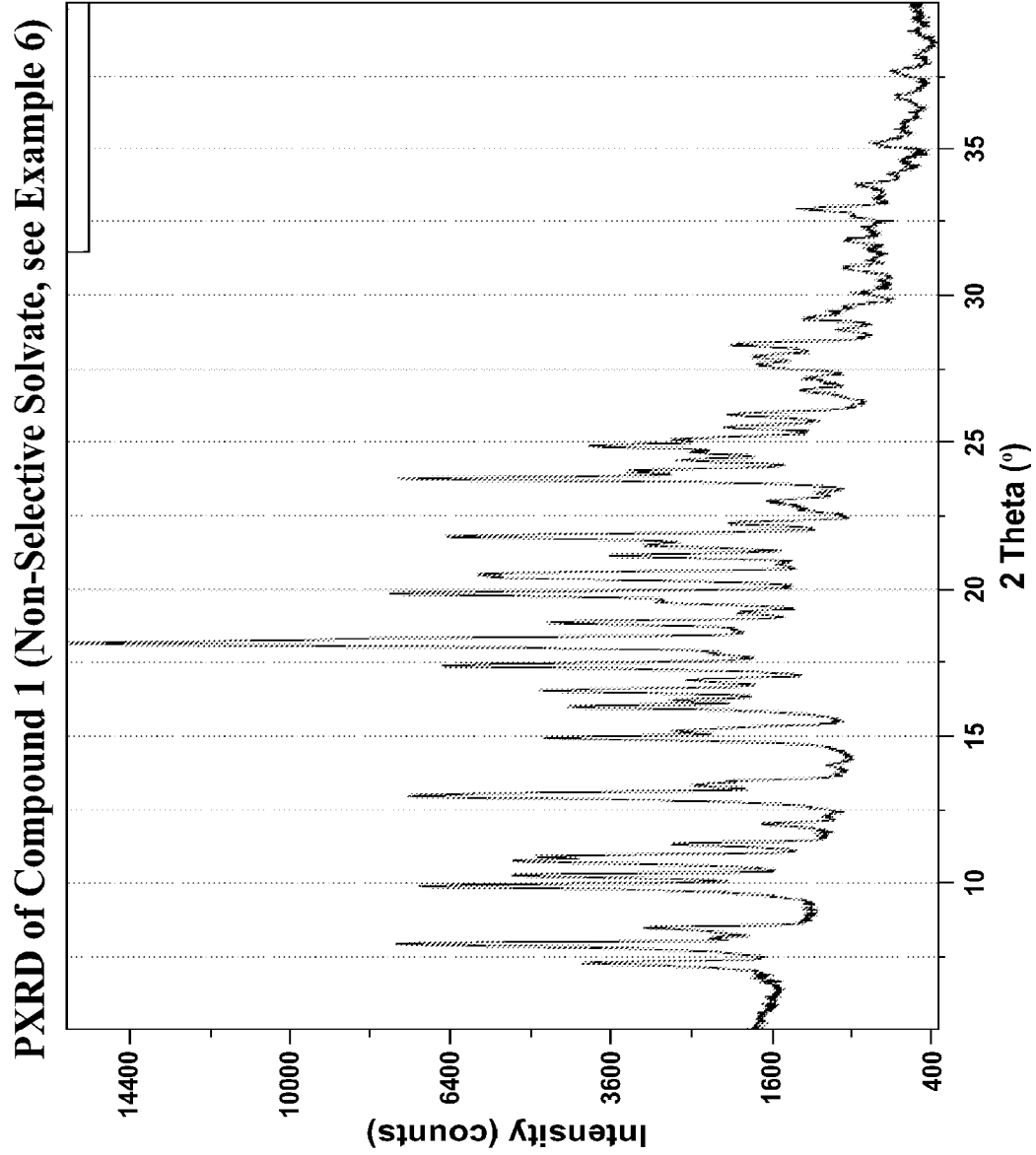
FIG. 10 shows a powder X-ray diffraction (PXRD) pattern for a sample containing a crystalline form of Compound 1 (non-selective solvate), see Example 6.

| | |
|---|---|
| PXRD | FIG. 10: Peaks of about ≥24% relative intensity at 7.9, 9.9, 10.3, 10.7, 10.9, 13.0, 14.9, 16.5, 17.4, 18.2, 18.3, 18.9, 19.9, 20.4, 20.5, 21.8, and 23.8 °2θ |

The amount of the respective solvent present in these solvates can vary and can readily be determined by TGA. One such non-selective solvate of Compound 1 is the ethyl acetate solvate as described in Example 6. The physical properties (i.e., TGA and DSC) for this ethyl acetate non-selective solvate are summarized in Table 10 below.

TABLE 10

Compound 1 (Non-Selective Solvate/Ethyl Acetate, Example 6)

Figure 13:
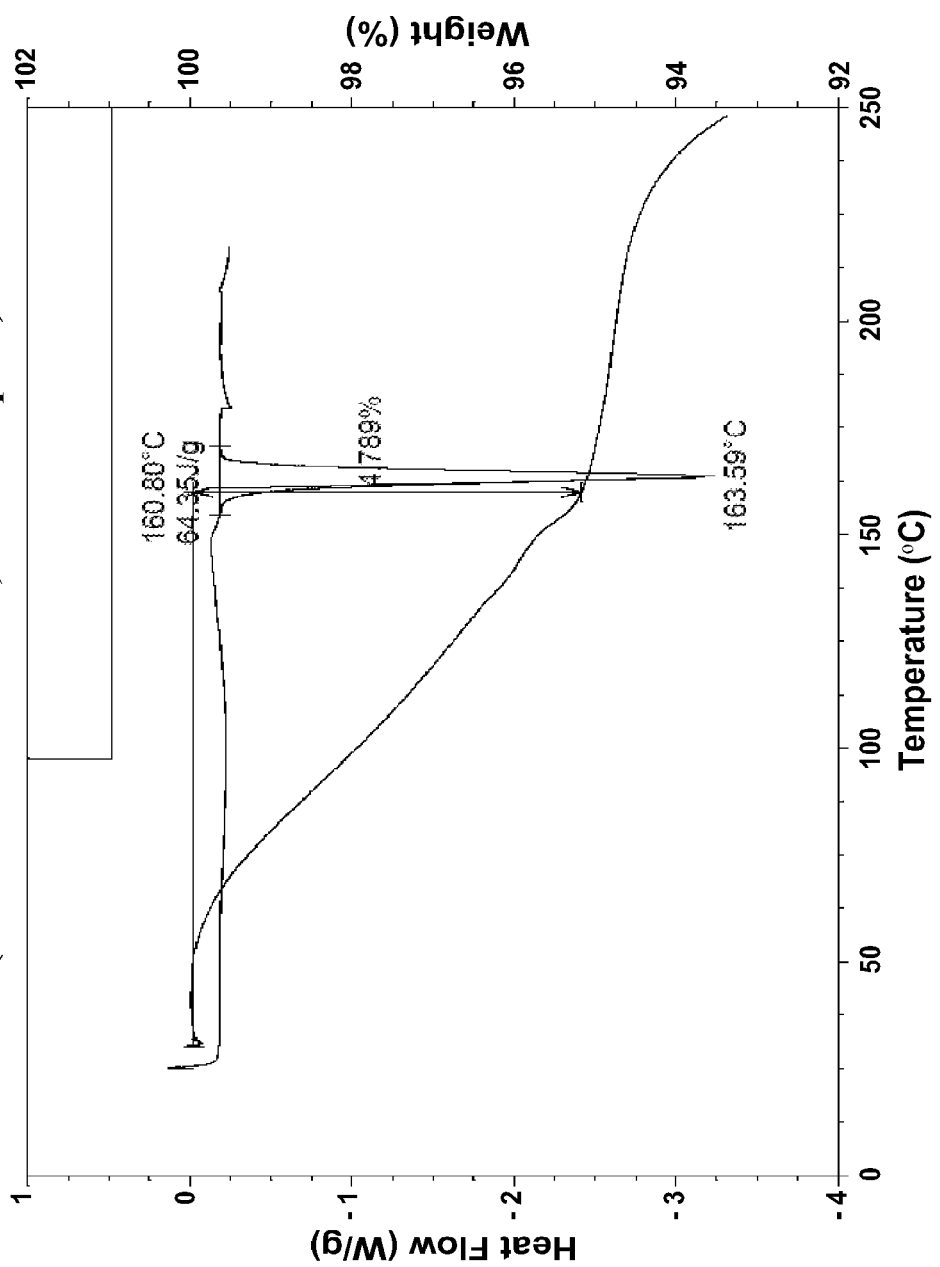
FIG. 13 shows a differential scanning calorimetry (DSC) thermogram for a sample containing a crystalline form of Compound 1 (non-selective solvate) and a thermogravimetric analysis (TGA) thermogram of a sample containing a crystalline form of Compound 1 (non-selective solvate), see Example 6.

| | |
|---|---|
| TGA | FIG. 13: Decrease in weight of about 4.8% out to about 150° C. |
| DSC | FIG. 13: Endotherm extrapolated onset temperature: about 161° C. |

Certain powder X-ray diffraction peaks for the non-selective solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1) are shown in Table 11 below.

TABLE 11

| Pos. [°2θ] | d-spacing [Å] | Rel. Int. [%] |
|---|---|---|
| 7.3 | 12.14275 | 16.7 |
| 7.9 | 11.16727 | 39.7 |
| 8.5 | 10.44535 | 11.7 |
| 9.9 | 8.93424 | 37.9 |
| 10.3 | 8.61737 | 26.3 |
| 10.7 | 8.23598 | 26.3 |
| 10.9 | 8.12357 | 24.0 |
| 11.3 | 7.81277 | 10.5 |
| 13.0 | 6.82221 | 40.8 |
| 13.3 | 6.64907 | 9.5 |
| 14.9 | 5.92853 | 24.0 |
| 15.2 | 5.84616 | 11.2 |
| 16.0 | 5.53769 | 21.1 |
| 16.2 | 5.46327 | 11.9 |
| 16.5 | 5.35726 | 24.5 |
| 16.9 | 5.24138 | 10.7 |
| 17.4 | 5.09682 | 36.7 |
| 18.2 | 4.88174 | 100.0 |
| 18.3 | 4.83505 | 44.3 |
| 18.9 | 4.70738 | 24.3 |
| 19.2 | 4.62061 | 7.0 |
| 19.6 | 4.53523 | 13.6 |
| 19.9 | 4.47005 | 44.2 |
| 20.4 | 4.35851 | 29.0 |
| 20.5 | 4.33052 | 32.8 |
| 21.2 | 4.1998 | 18.1 |
| 21.5 | 4.13161 | 14.7 |
| 21.8 | 4.07567 | 37.1 |
| 22.3 | 3.99444 | 8.1 |
| 23.8 | 3.74137 | 43.5 |
| 24.0 | 3.70405 | 16.7 |
| 24.4 | 3.64871 | 12.3 |
| 24.7 | 3.60844 | 11.6 |
| 24.9 | 3.57752 | 20.8 |
| 25.1 | 3.54559 | 13.0 |
| 25.5 | 3.49243 | 9.0 |
| 26.0 | 3.43338 | 8.8 |
| 27.7 | 3.22622 | 6.9 |
| 27.9 | 3.19367 | 7.1 |
| 28.3 | 3.14991 | 8.6 |

One aspect of the present invention relates to non-selective solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

One aspect of the present invention relates to a non-selective solvate having a powder X-ray diffraction pattern comprising a peak, in terms of 2θ, at 18.2°±0.2°. In some embodiments, the non-selective solvate has a powder X-ray diffraction pattern comprising peaks, in terms of 2θ, at 18.2°±0.2° and 18.3°±0.2°. In some embodiments, the non-selective solvate has a powder X-ray diffraction pattern comprising peaks, in terms of 2θ, at 18.2°±0.2°, 18.3°±0.2°, and 19.9°±0.2°. In some embodiments, the non-selective solvate has a powder X-ray diffraction pattern comprising peaks, in terms of 2θ, at 18.2°±0.2°, 18.3°±0.2°, 19.9°±0.2°, 23.8°±0.2°, and 13.0°±0.2°. In some embodiments, the non-selective solvate has a powder X-ray diffraction pattern comprising peaks, in terms of 2θ, at 18.2°±0.2°, 18.3°±0.2°, 19.9°±0.2°, 23.8°±0.2°, 13.0°±0.2°, 7.9°±0.2°, and 9.9°±0.2°. In some embodiments, the non-selective solvate has a powder X-ray diffraction pattern comprising peaks, in terms of 2θ, at 18.2°±0.2°, 18.3°±0.2°, 19.9°±0.2°, 23.8°±0.2°, 13.0°±0.2°, 7.9°±0.2°, 9.9°±0.2°, 21.8°±0.2°, and 17.4°±0.2°. In some embodiments, the non-selective solvate has a powder X-ray diffraction pattern comprising peaks, in terms of 2θ, at 18.2°±0.2°, 18.3°±0.2°, 19.9°±0.2°, 23.8°±0.2°, 13.0°±0.2°, 7.9°±0.2°, 9.9°±0.2°, 21.8°±0.2°, 17.4°±0.2°, 20.5°±0.2°, 20.4°±0.2°, 10.7°±0.2°, 10.3°±0.2°, 16.5°±0.2°, 18.9°±0.2°, 14.9°±0.2°, and 10.9°±0.2°. In some embodiments, the non-selective solvate has a powder X-ray diffraction pattern substantially as shown in FIG. 10, wherein by "substantially" is meant that the reported peaks can vary by about ±0.2°2θ.

In some embodiments, the non-selective solvate has a differential scanning calorimetry thermogram comprising an endotherm with an extrapolated onset temperature between about 159.8° C. and about 165.8° C. In some embodiments, the non-selective solvate has a differential scanning calorimetry thermogram comprising an endotherm with an extrapolated onset temperature between about 160.8° C. and about 164.8° C. In some embodiments, the non-selective solvate has a differential scanning calorimetry thermogram comprising an endotherm with an extrapolated onset temperature between about 158.8° C. and about 162.8° C. In some embodiments, the non-selective solvate has a differential scanning calorimetry thermogram comprising an endotherm with an extrapolated onset temperature between about 159.8° C. and about 161.8° C. In some embodiments, the non-selective solvate has a differential scanning calorimetry thermogram comprising an endotherm with an extrapolated onset temperature at about 160.8° C. In some embodiments, the non-selective solvate has a differential scanning calorimetry thermogram substantially as shown in FIG. 13, wherein by "substantially" is meant that the reported DSC features can vary by about ±4° C. and that the reported DSC features can vary by about ±20 joules per gram.

In some embodiments, the non-selective solvate has a thermogravimetric analysis profile showing about 5.0% weight loss below about 150° C. In some embodiments, the non-selective solvate has a thermogravimetric analysis profile showing about 4.9% weight loss below about 150° C. In some embodiments, the non-selective solvate has a thermogravimetric analysis profile showing about 4.8% weight loss below about 150° C. In some embodiments, the non-selective solvate has a thermogravimetric analysis profile substantially as shown in FIG. 13, wherein by "substantially" is meant that the reported TGA features can vary by about ±5° C., and that that the reported TGA features can vary by about ±2% weight change.

One aspect of the present invention relates to the non-selective solvate having:

1) a powder X-ray diffraction pattern comprising peaks, in terms of 2θ, at 18.2°±0.2° and 18.3°±0.2°; and/or 2) a differential scanning calorimetry thermogram comprising an endotherm with an extrapolated onset temperature between about 160.8° C. and about 165.8° C.

One aspect of the present invention relates to the non-selective solvate having:

1) a powder X-ray diffraction pattern comprising peaks, in terms of 2θ, at 18.2°±0.2°, 18.3°±0.2°, and 19.9°±0.2°; and/or 2) a differential scanning calorimetry thermogram comprising an endotherm with an extrapolated onset temperature between about 160.8° C. and about 164.8° C.

One aspect of the present invention relates to the non-selective solvate having:

1) a powder X-ray diffraction pattern comprising peaks, in terms of 2θ, at 18.2°±0.2°, 18.3°±0.2°, 19.9°±0.2°, 23.8°±0.2°, and 13.0°±0.2°; and/or 2) a differential scanning calorimetry thermogram comprising an endotherm with an extrapolated onset temperature between about 158.8° C. and about 162.8° C.

One aspect of the present invention relates to the non-selective solvate having:

1) a powder X-ray diffraction pattern comprising peaks, in terms of 2θ, at 18.2°±0.2°, 18.3°±0.2°, 19.9°±0.2°, 23.8°±0.2°, 13.0°±0.2°, 7.9°±0.2°, and 9.9°±0.2°;

2) a differential scanning calorimetry thermogram comprising an endotherm with an extrapolated onset temperature between about 159.8° C. and about 161.8° C.; and/or 3) a thermogravimetric analysis profile showing about 5.0% weight loss below about 150° C.

One aspect of the present invention relates to the non-selective solvate having:

1) a powder X-ray diffraction pattern comprising peaks, in terms of 2θ, at 18.2°±0.20, 18.3°±0.2°, 19.9°±0.2°, 23.8°±0.2°, 13.0°±0.2°, 7.9°±0.2°, 9.9°±0.2°, 21.8°±0.2°, and 17.4°±0.2°;

2) a differential scanning calorimetry thermogram comprising an endotherm with an extrapolated onset temperature at about 160.8° C.; and/or 3) a thermogravimetric analysis profile showing about 4.9% weight loss below about 150° C.

One aspect of the present invention relates to the non-selective solvate having:

1) a powder X-ray diffraction pattern comprising peaks, in terms of 2θ, at 18.2°±0.2°, 18.3°±0.2°, 19.9°±0.2°, 23.8°±0.2°, 13.0°±0.2°, 7.9°±0.2°, 9.9°±0.2°, 21.8°±0.2°, 17.4°±0.2°, 20.5°±0.2°, 20.4°±0.2°, 10.7°±0.2°, 10.3°±0.2°, 16.5°±0.2°, 18.9°±0.2°, 14.9°±0.2°, and 10.9°±0.2°;

2) a differential scanning calorimetry thermogram comprising an endotherm with an extrapolated onset temperature at about 160.8° C.; and/or 3) a thermogravimetric analysis profile showing about 4.8% weight loss below about 150° C.

One aspect of the present invention relates to the non-selective solvate having:

1) a powder X-ray diffraction pattern substantially as shown in FIG. 10;

2) a differential scanning calorimetry thermogram substantially as shown in FIG. 13; and/or 3) a thermogravimetric analysis profile substantially as shown in FIG. 13.

5. Compound 1 (Ethyl Acetate Solvate).

One aspect of the present invention relates to the ethyl acetate solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1). The ethyl acetate solvate of Compound 1 is characterized by PXRD. The physical properties for the ethyl acetate solvate as determined by PXRD are summarized in Table 12 below.

TABLE 12

Compound 1 (Ethyl Acetate Solvate)

Figure 16:
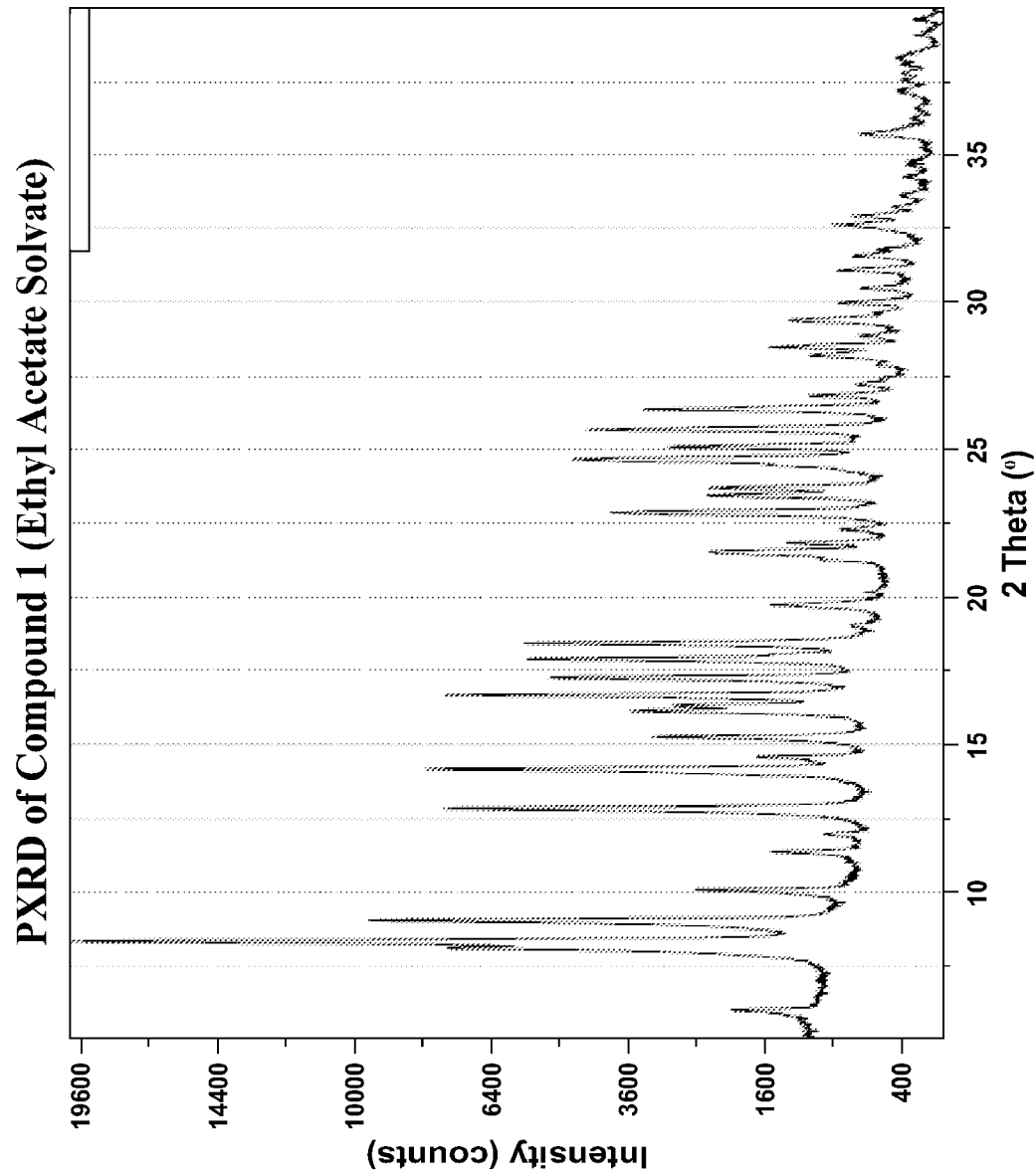
FIG. 16 shows a powder X-ray diffraction (PXRD) pattern for a sample containing a crystalline form of Compound 1 (ethyl acetate solvate).

| | |
|---|---|
| PXRD | FIG. 16: Peaks of about ≥16.0% relative intensity at 8.1, 8.3, 9.0, 12.8, 14.2, 16.1, 16.7, 17.3, 17.9, 18.4, 22.9, 24.7, and 25.7 °2θ |

The amount of ethyl acetate present in this solvate can vary but can readily be determined by TGA. The physical properties for a the non-selective solvate as the ethyl acetate solvate from Example 7 are summarized in Table 13 below.

TABLE 13

Compound 1 (Non-Selective Solvate/Ethyl Acetate, Example 7)

Figure 17:
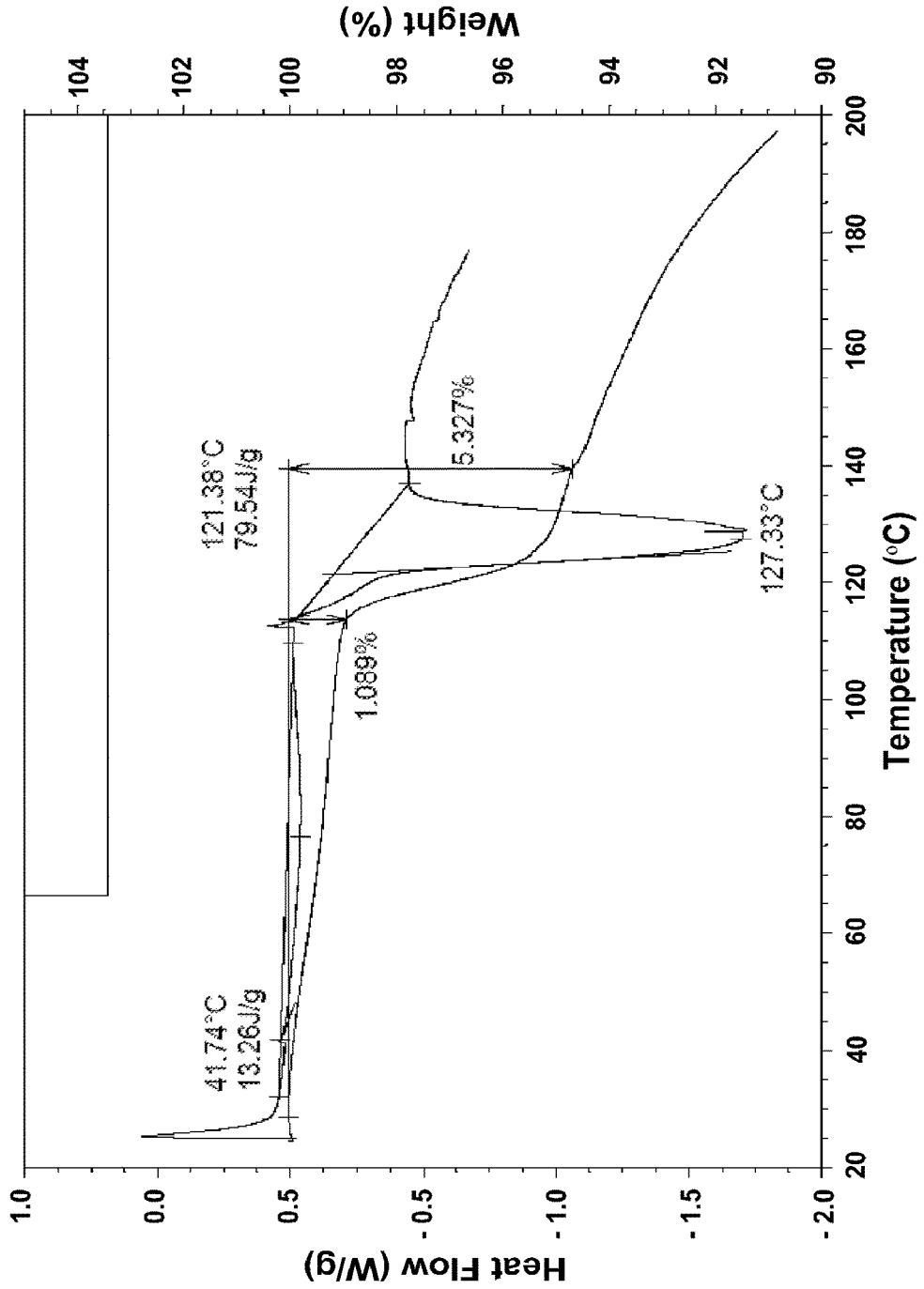
FIG. 17 shows a differential scanning calorimetry (DSC) thermogram for a sample containing a crystalline form of Compound 1 (ethyl acetate solvate) and a thermogravimetric analysis (TGA) therlmogram of a sample containing a crystalline form of Compound 1 (ethyl acetate solvate).

| | |
|---|---|
| TGA | FIG. 17: Decrease in weight of about 4.7% by weight out to about 120° C. |
| DSC | FIG. 17: Endotherm extrapolated onset temperature: about 121° C. |

Certain powder X-ray diffraction peaks for the crystalline form of ethyl acetate solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1) are shown in Table 14 below.

TABLE 14

| Pos. [°2θ.] | d-spacing [Å] | Rel. Int. [%] |
|---|---|---|
| 6.0 | 14.7 | 9.0 |
| 8.1 | 10.9 | 36.8 |
| 8.3 | 10.6 | 100.0 |
| 9.0 | 9.8 | 47.5 |
| 10.1 | 8.8 | 11.6 |
| 11.4 | 7.8 | 6.4 |
| 12.8 | 6.9 | 37.1 |
| 14.2 | 6.3 | 39.8 |
| 14.6 | 6.1 | 7.4 |
| 15.3 | 5.8 | 14.9 |
| 16.1 | 5.5 | 16.9 |
| 16.3 | 5.4 | 13.4 |
| 16.7 | 5.3 | 37.1 |
| 17.3 | 5.1 | 24.8 |
| 17.9 | 5.0 | 27.1 |
| 18.4 | 4.8 | 27.4 |
| 19.7 | 4.5 | 6.7 |
| 21.5 | 4.1 | 10.1 |
| 21.6 | 4.1 | 9.8 |
| 21.8 | 4.1 | 5.7 |
| 22.9 | 3.9 | 18.6 |
| 23.4 | 3.8 | 10.7 |
| 23.7 | 3.8 | 10.6 |
| 24.7 | 3.6 | 22.4 |
| 25.1 | 3.5 | 13.7 |
| 25.7 | 3.5 | 21.0 |
| 26.4 | 3.4 | 15.6 |
| 26.8 | 3.3 | 4.6 |
| 28.5 | 3.1 | 6.7 |
| 29.4 | 3.0 | 5.3 |

One aspect of the present invention relates to ethyl acetate solvates of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

One aspect of the present invention relates to an ethyl acetate solvate having a powder X-ray diffraction pattern comprising a peak, in terms of 2θ, at 8.3°±0.2°. In some embodiments, the ethyl acetate solvate has a powder X-ray diffraction pattern comprising peaks, in terms of 2θ, at 8.3°±0.2° and 9.0°±0.2°. In some embodiments, the ethyl acetate solvate has a powder X-ray diffraction pattern comprising peaks, in terms of 2θ, at 8.3°±0.2°, 9.0°±0.2°, and 14.2°±0.2°. In some embodiments, the ethyl acetate solvate has a powder X-ray diffraction pattern comprising peaks, in terms of 2θ, at 8.3°±0.2°, 9.0°±0.2°, 14.2°±0.2°, 16.7°±0.2°, and 12.8°±0.2°. In some embodiments, the ethyl acetate solvate has a powder X-ray diffraction pattern comprising peaks, in terms of 2θ, at 8.3°±0.2°, 9.0°±0.2°, 14.2°±0.2°, 16.7°±0.2°, 12.8°±0.2°, 8.1°±0.2°, and 18.4°±0.2°. In some embodiments, the ethyl acetate solvate has a powder X-ray diffraction pattern comprising peaks, in terms of 2θ, at 8.3°±0.2°, 9.0°±0.2°, 14.2°±0.2°, 16.7°±0.2°, 12.8°±0.2°, 8.1°±0.2°, 18.4°±0.2°, 17.9°±0.2°, and 17.3°±0.2°. In some embodiments, the ethyl acetate solvate has a powder X-ray diffraction pattern comprising peaks, in terms of 2θ, at 8.3°±0.2°, 9.0°±0.2°, 14.2°±0.2°, 16.7°±0.2°, 12.8°±0.2°, 8.1°±0.2°, 18.4°±0.2°, 17.9°±0.2°, 17.3°±0.2°, 24.7°±0.2°, 25.7°±0.2°, 22.9°±0.2°, and 16.1°±0.2°. In some embodiments, the ethyl acetate solvate has a powder X-ray diffraction pattern substantially as shown in FIG. 16, wherein by "substantially" is meant that the reported peaks can vary by about ±0.2°2θ.

In some embodiments, the ethyl acetate solvate has a differential scanning calorimetry thermogram comprising an endotherm with an extrapolated onset temperature between about 116.4° C. and about 126.4° C. In some embodiments, the ethyl acetate solvate has a differential scanning calorimetry thermogram comprising an endotherm with an extrapolated onset temperature between about 117.4° C. and about 125.4° C. In some embodiments, the ethyl acetate solvate has a differential scanning calorimetry thermogram comprising an endotherm with an extrapolated onset temperature between about 119.4° C. and about 123.4° C. In some embodiments, the ethyl acetate solvate has a differential scanning calorimetry thermogram comprising an endotherm with an extrapolated onset temperature between about 120.4° C. and about 122.4° C. In some embodiments, the ethyl acetate solvate has a differential scanning calorimetry thermogram comprising an endotherm with an extrapolated onset temperature at about 121.4° C. In some embodiments, the ethyl acetate solvate has a differential scanning calorimetry thermogram substantially as shown in FIG. 17, wherein by "substantially" is meant that the reported DSC features can vary by about ±4° C. and that the reported DSC features can vary by about ±20 joules per gram.

In some embodiments, the ethyl acetate solvate has a thermogravimetric analysis profile showing about 5.5% weight loss below about 135° C. In some embodiments, the ethyl acetate solvate has a thermogravimetric analysis profile showing about 5.4% weight loss below about 135° C. In some embodiments, the ethyl acetate solvate has a thermogravimetric analysis profile showing about 5.3% weight loss below about 135° C. In some embodiments, the ethyl acetate solvate has a thermogravimetric analysis profile substantially as shown in FIG. 17, wherein by "substantially" is meant that the reported TGA features can vary by about ±5° C., and that that the reported TGA features can vary by about ±2% weight change.

One aspect of the present invention relates to the ethyl acetate solvate having:

1) a powder X-ray diffraction pattern comprising peaks, in terms of 2θ, at 8.3°±0.2° and 9.0°±0.2°; and/or 2) a differential scanning calorimetry thermogram comprising an endotherm with an extrapolated onset temperature between about 116.4° C. and about 126.4° C.

One aspect of the present invention relates to the ethyl acetate solvate having:

1) a powder X-ray diffraction pattern comprising peaks, in terms of 2θ, at 8.3°±0.2°, 9.0°±0.2°, and 14.2°±0.2°; and/or 2) a differential scanning calorimetry thermogram comprising an endotherm with an extrapolated onset temperature between about 117.4° C. and about 125.4° C.

One aspect of the present invention relates to the ethyl acetate solvate having:

1) a powder X-ray diffraction pattern comprising peaks, in terms of 2θ, at 8.3°±0.2°, 9.0°±0.2°, 14.2°±0.2°, 16.7°±0.2°, and 12.8°±0.2°; and/or 2) a differential scanning calorimetry thermogram comprising an endotherm with an extrapolated onset temperature between about 119.4° C. and about 123.4° C.

One aspect of the present invention relates to the ethyl acetate solvate having:

1) a powder X-ray diffraction pattern comprising peaks, in terms of 2θ, at 8.3°±0.2°, 9.0°±0.2°, 14.2°±0.2°, 16.7°±0.2°, 12.8°±0.2°, 8.1°±0.2°, and 18.4°±0.2°;

2) a differential scanning calorimetry thermogram comprising an endotherm with an extrapolated onset temperature between about 120.4° C. and about 122.4° C.; and/or 3) a thermogravimetric analysis profile showing about 5.5% weight loss below about 135° C.

One aspect of the present invention relates to the ethyl acetate solvate having:

1) a powder X-ray diffraction pattern comprising peaks, in terms of 2θ, at 8.3°±0.2°, 9.0°±0.2°, 14.2°±0.2°, 16.7°±0.2°, 12.8°±0.2°, 8.1°±0.2°, 18.4°±0.2°, 17.9°±0.2°, and 17.3°±0.2°;

2) a differential scanning calorimetry thermogram comprising an endotherm with an extrapolated onset temperature at about 121.4° C.; and/or 3) a thermogravimetric analysis profile showing about 5.4% weight loss below about 135° C.

One aspect of the present invention relates to the ethyl acetate solvate having:

1) a powder X-ray diffraction pattern comprising peaks, in terms of 2θ, at 8.3°±0.2°, 9.0°±0.2°, 14.2°±0.2°, 16.7°±0.2°, 12.8°±0.2°, 8.1°±0.2°, 18.4°±0.2°, 17.9°±0.2°, 17.3°±0.2°, 24.7°±0.2°, 25.7°±0.2°, 22.9°±0.2°, and 16.1°±0.2°;

2) a differential scanning calorimetry thermogram comprising an endotherm with an extrapolated onset temperature at about 121.4° C.; and/or 3) a thermogravimetric analysis profile showing about 5.3% weight loss below about 135° C.

One aspect of the present invention relates to the ethyl acetate solvate having:

1) a powder X-ray diffraction pattern substantially as shown in FIG. 16;

2) a differential scanning calorimetry thermogram substantially as shown in FIG. 17; and/or 3) a thermogravimetric analysis profile substantially as shown in FIG. 17.

The crystalline forms described herein can be prepared by any of the suitable procedures known in the art for preparing crystalline polymorphs. In some embodiments the crystalline forms described herein are prepared according to the Examples. In some embodiments, the crystalline forms described herein can be prepared by heating crystalline forms other than the crystalline forms described herein. In some embodiments, the crystalline forms described herein can be prepared by recrystallizing crystalline forms other than the crystalline forms described herein.

Compound 1 of the present invention may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]).

It is understood that the present invention embraces each enantiomer and mixtures thereof. Separation of the individual isomers (such as, by chiral HPLC, recrystallization of diastereoisomeric mixtures and the like) or selective synthesis (such as, by enantiomeric selective syntheses and the like) of the individual isomers is accomplished by application of various methods which are well known to practitioners in the art.

Indications and Methods of Prophylaxis and/or Treatment

In addition to the foregoing beneficial uses for the modulators of cannabinoid receptor activity disclosed herein, the compounds disclosed herein are useful in the treatment of several additional diseases and disorders, and in the amelioration of symptoms thereof. Without limitation, these include the following:

1. Pain

The analgesic properties of cannabinoids have been recognized for many years. For example, animal studies have demonstrated that the $CB_1/CB_2$ agonists anandamide, THC, CP55,940 and WIN 55212-2 are effective against acute and chronic pain from chemical, mechanical, and thermal pain stimuli (reviewed in Walker and Huang (2002) *Pharmacol. Ther.* 95:127-135; reviewed in Pacher, P et al. (2006) *Pharmacol. Rev.* 58(3): 389-462). In humans, topical administration of the $CB_1/CB_2$ agonist HU-210 attenuates capsaicin-induced hyperalgesia and allodynia (Rukwied, R. et al. (2003) *Pain* 102:283-288), and co-administration of the $CB_1/CB_2$ agonist THC and cannabidiol (nabiximols, trademark Sativex®) provides relief from cancer-associated pain (GW Pharmaceuticals press release Jan. 19, 2005, Jun. 19, 2007) and multiple-sclerosis-associated pain and spasticity (GW Pharmaceuticals press release Sep. 27, 2005, Mar. 11, 2009).

The role of $CB_1$ in mediating these analgesic effects is well-documented (reviewed in Manzanares, J. et al. (2006) *Current Neuropharmacology* 4:239-57; reviewed in Pacher, P. et al. (2006) *Pharmacol. Rev.* 58(3): 389-462). For example, blockade of peripheral or central $CB_1$ leads to hyperalgesia (Richardson, J. D. et al. (1997) *Eur. J. Pharmacol.* 345:145-153; Calignano, A. et al. (1998) *Nature* 394:277-281), whereas $CB_1$ activation by exogenous administration of a $CB_1$ agonist arachidonyl-2-chloroethylamide reduces pain (Furuse, S. et al. (2009) *Anesthesiology* 111 (1):173-86).

Although less well-documented, $CB_2$ also plays a role in mediating analgesic effects of cannabinoids (reviewed in Guindon and Hohmann (2008) *Br. J. Pharmacol.* 153:319-334). For example, systemic delivery of the $CB_2$-selective agonist AM1241 suppresses hyperalgesia induced in the carrageenan, capsaicin, and formalin models of inflammatory pain in rodents (reviewed in Guindon and Hohmann (2008) *Br. J. Pharmacol.* 153:319-334). Local (subcutaneous) or systemic administration of AM1241 also reverses tactile and thermal hypersensitivity in rats following ligation of spinal nerves in the chronic constriction injury model of neuropathic pain (Malan, T. P. et al. (2001) *Pain* 93:239-245; Ibrahim, M. M. et al. (2003) *Proc. Natl. Acad. Sci.* 100(18): 10529-10533), an effect which is inhibited by treatment with the $CB_2$-selective antagonist AM630 (Ibrahim, M. M. et al.

(2005) *Proc. Natl. Acad. Sci.* 102(8):3093-8). The $CB_2$-selective agonist GW405833 administered systemmically significantly reverses hypersensitivity to mechanical stimuli in rats following ligation of spinal nerves (Hu, B. et al. (2009) *Pain* 143:206-212). Thus, $CB_2$-selective agonists have also been demonstrated to attenuate pain in experimental models of acute, inflammatory, and neuropathic pain, and hyperalgesia.

Accordingly, $CB_2$-specific agonists and/or $CB_1/CB_2$ agonists find use in the treatment and/or prophylaxis of acute nociception and inflammatory hyperalgesia, as well as the allodynia and hyperalgesia produced by neuropathic pain. For example, these agonists are useful as an analgesic to treat pain arising from autoimmune conditions; allergic reactions; bone and joint pain; muscle pain; dental pain; nephritic syndrome; scleroderma; thyroiditis; migraine and other headache pain; pain associated with diabetic neuropathy; fibromyalgia, HIV-related neuropathy, sciatica, and neuralgias; pain arising from cancer; and pain that occurs as an adverse affect of therapeutics for the treatment of disease.

Furthermore, although cannabinoids exert their antinociceptive effects by complex mechanisms involving effects on the central nervous system, spinal cord, and peripheral sensory nerves (reviewed in Pacher, P. et al. (2006) *Pharmacol. Rev.* 58(3): 389-462), an analysis of models of inflammatory and neuropathic pain in mice that are deficient for $CB_1$ only in nociceptive neurons localized in the peripheral nervous system demonstrates that the contribution of $CB_1$-type receptors expressed on the peripheral terminals of nociceptors to cannabinoid-induced analgesia is paramount (Agarwal, N. et al. (2007) *Nat. Neurosci.* 10(7): 870-879). Accordingly, $CB_1$ agonists that are unable to cross the blood brain barrier still find use in the treatment and/or prophylaxis of acute pain, inflanunatory pain, neuropathic pain, and hyperalgesia.

2. Disorders of the Immune System

Autoimmune Disorders.

Cannabinoid receptor agonists have been demonstrated to attenuate aberrant immune responses in autoimmune disorders, and in some cases, to provide protection to the tissue that is being inappropriately targeted by the immune system.

For example, Multiple Sclerosis (MS) is an autoimmune disorder that results in the demyelination of neurons in the CNS. The $CB_1/CB_2$ agonist THC significantly inhibits the severity of clinical disease in the Experimental Autoimmune Encephalomyelitis (EAE) mouse model of MS, an effect that is believed to be mediated by $CB_1$ on neurons and $CB_2$ on immune cell (Maresz, K. et al. (2007) *Nat. Med.* 13(4):492-497). Consistent with these results, $CB_1$-selective agonist WIN 55212-2 provides significant neuroprotection in the experimental allergic uveitis (EAU) model in mice (Pryce, G. et al. (2003) *Brain* 126:2191-2202), whereas $CB_2$-selective agonist HU-308 markedly reduces the recruitment of immature myeloid cells and T cells, microglial and infiltrating myeloid cell proliferation, and axonal loss in the EAE model (Palazuelos, J. et al. (2008). *J. Biol. Chem.* 283(19): 13320-9). Likewise, the $CB_1/CB_2$ agonist WIN 55212-2 significantly inhibits leukocyte rolling and adhesion in the brain in the EAE mouse model, an effect that is blocked by the $CB_2$-selective antagonist SR144528 but not the $CB_1$-selective antagonist SR141716A (Ni, X. et al. *Mult. Sclerosis* 10(2):158-64). Accordingly, $CB_2$-selective agonists and/or $CB_1/CB_2$ agonists find use in the treatment and/or prophylaxis of Multiple Sclerosis and related autoimmune demyelinating diseases, e.g. Guillan-Barré syndrome, polyradiculoneuropathy and chronic inflammatory demyelination.

As another example, the autoimmune disease Rheumatoid Arthritis (RA) is a chronic, systemic inflammatory disorder of the skeletal system that principally attacks the joints to produce an inflammatory synovitis and that often progresses to destruction of the articular cartilage and ankylosis of the joints. The $CB_1/CB_2$ agonists WIN 55212-2 and HU-210 significantly inhibit IL-1 alpha-stimulated proteoglycan and collagen degradation in bovine nasal cartilage explants in vitro (Mbvundula, E. et al. (2006) *J. Pharm. and Pharmacol.* 58:351-358). Accordingly, $CB_2$-selective agonists and/or $CB_1/CB_2$ agonists find use in the treatment and/or prophylaxis of autoimmune arthritic diseases, for example, rheumatoid arthritis, psoriatic arthritis, ankylosing spondylarthritis, and reactive arthritis.

Type 1 Hypersensitivity and Allergic Response.

Cannabinoid receptor agonists have been demonstrated to attenuate aberrant immune responses in allergic reactions as well. In type-1, or immediate, hypersensitivity, plasma cells that have been activated by an allergen secrete IgE antibodies, which bind to Fc receptors on the surface of tissue mast cells and blood basophils and eosinophils. Repeated exposure to the same allergen results in cross-linking of the bound IgE on sensitized cells, resulting in secretion of pharmacologically active mediators such as histamine, leukotriene and prostaglandin. These mediators are responsible for the symptoms associated with allergies, including vasodilation and increased permeability, smooth muscle spasms, and leukocyte extravasation. Topical administration of the $CB_1/CB_2$ agonist HU-210 reduces these histamine-induced responses in human skin (Dvorak, M. et al. (2003) *Inflamm. Res.* 52:238-245). Similarly, subcutaneous injection of $CB_1/CB_2$ agonist THC or increased levels of endogenous cannabinoids reduces cutaneous inflammation and the pruritis (itch) associated with it in a mouse model for allergic contact dermatitis. (Karsak et al. (2007) *Science,* 316(5830), 1494-1497). In contrast, injection of the $CB_1$ receptor antagonist S141716A or the $CB_2$ receptor antagonist SR144528 exacerbates this inflammation and pruritis. (Karsak et al. (2007) *Science,* 316(5830), 1494-1497). Accordingly, $CB_2$-selective agonists and/or $CB_1/CB_2$ agonists find use in the treatment of allergic reactions including atopic dermatitis (pruritis/itch), urticaria (hives), asthma, conjunctivitis, allergic rhinitis (hay fever), and anaphylaxis.

Conditions Associated with CNS Inflammation.

$CB_2$ agonists have been demonstrated to attenuate inflammation in the CNS. For example, administration of $CB_2$ agonists prevents the activation of microglia in rodent models of Alzheimer's Disease (Ashton J. C., et al. (2007) *Curr. Neuropharmacol.* 5(2):73-80). Likewise, administration of $CB_2$ agonists reduces the volume of infarcts by 30% in a rodent occlusion model of stroke (Zhang, M. et al. (2007) *J. Cereb. Blood Flow Metab.* 27:1387-96). Thus, $CB_2$ agonists find use in the treatment and/or prophylaxis of neuropathologies associated with CNS inflammation, e.g. Alzheimer's, stroke-induced damage, dementia, ALS, and HIV.

Conditions Associated with Vascular Inflammation.

$CB_2$ is expressed in macrophages and T cells in atherosclerotic plaques, and the $CB_1/CB_2$ agonist THC reduces the progression of atherosclerosis in ApoE knockout mice, a well studied mouse model of atherosclerosis. The $CB_2$-specific antagonist SR144528 completely blocks this effect in vitro and in vivo (Steffens, S. et al. (2005) Nature 434:782-786). Thus, $CB_2$ agonists find use in treating atherosclerosis.

Other Disorders Associated with Aberrant or Unwanted Immune Response.

Given the expression of $CB_2$ on a number of different types of immune cells and the attenuating effects that $CB_2$ agonists have been observed to have on the activities of these cells, $CB_2$ agonists are useful for the treatment and/or prophylaxis of other disorders wherein undesired immune cell activity and/or inflammation is observed. Such exemplary disorders include osteoarthritis, anaphylaxis, Behcet's disease, graft rejection, vasculitis, gout, spondylitis, viral and bacterial diseases, e.g. AIDS, and meningitis; and other autoimmune disorders such as lupus, e.g. systemic lupus erythematosus; inflammatory bowel disease, e.g. Crohn's disease, ulcerative colitis; psoriasis; autoimmune hepatitis; and type 1 diabetes mellitus.

3. Bone and Joint Diseases

Osteoporosis.

$CB_2$ is expressed in osteoblasts, osteocytes, and osteoclasts. Osteoblasts make new bone, whereas osteoclasts degrade it. The $CB_2$-specific agonist HU-308 enhances endocortical osteoblast numbers and activity while simultaneously inhibiting proliferation of osteoclast precursors in bone marrow-derived osteoblasts/stromal cells in vitro, and attenuates ovariectomy-induced bone loss and stimulates cortical thickness by stimulating endocortical bone formation and suppressing osteoclast number in vivo (Ofek, O. et al. (2006) Proc. Natl. Acad. Sci. 103(3):696-701). Thus, $CB_2$ agonists are useful for the treatment and/or prophylaxis of disease wherein bone density is decreased, such as osteoporosis.

Arthritis.

As discussed above, $CB_2$-selective agonists and $CB_1/CB_2$ agonists are useful for the treatment and/or prophylaxis of autoimmune arthritic diseases, for example, rheumatoid arthritis, psoriatic arthritis, ankylosing spondylarthritis, and reactive arthritis, and for the treatment and/or prophylaxis of inflammation associated with osteoarthritis. In addition, as discussed above, $CB_1$-selective agonists and $CB_1/CB_2$ agonists are useful for the treatment of pain associated with these arthritic disorders.

4. Eye Disease

Retinal pigment epithelial (RPE) cells provide trophic support to photoreceptor cells in the eye, and RPE cell death has been demonstrated to be a major contributor to Age-related Macular Degeneration (AMD). The $CB_1/CB_2$ agonist CP55940 significantly protects RPE cells from oxidative damage; the $CB_2$ receptor agonist, JWH015 provides comparable protection (Wei, Y. et al. (2009) Mol. Vis. 15:1243-51). Accordingly, $CB_2$-selective agonists find use in preventing the onset or progression of vision loss associated with AMD.

5. Cough

The cough reflex is predominantly under the control of two classes of sensory afferent nerve fibers, the myelinated A-delta fibers and the non-myelinated C-fibers, the activation of which (i.e. depolarization) elicits cough via the vagus nerve afferent pathway. The $CB_1/CB_2$ agonist CP55940 reduces capsaicin-, $PGE_2$- and hypertonic saline-induced depolarization of guinea pig and human vagus nerve preparations in vitro (Patel, H. J. et al. (2003) British J. Pharma. 140:261-8). The $CB_1/CB_2$ agonists WIN 55212-2 produced a dose-dependent inhibition of the number of capsaicin-induced coughs in mice (Morita, K. et al. (2003) Eur. J. Pharmacol. 474:269-272). The $CB_1/CB_2$ agonist anandamide produced a dose-dependent inhibition of the number of capsaicin-induced coughs in guinea pigs (Calignano, A. et al. (2000) Nature 408:96-101). $CB_1$-specific antagonist SR141716A attenuates the antitussive effects of WN 55212-2 and anandamide (Morita, K. et al. (2003) Eur. J. Pharmacol. 474:269-272; Calignano, A. et al. (2000) Nature 408:96-101). The $CB_2$-selective agonist JWH133 reduces capsaicin-, $PGE_2$- and hypertonic saline-induced depolarization of guinea pig and human vagus nerve preparations in vitro, and administration of $CB_2$-selective agonist JWH133 prior to exposure to the tussive agent citric acid significantly reduces cough in conscious guinea-pigs (Patel, H. J. et al. (2003) British J. Pharma. 140:261-8). Thus, both $CB_1$ and $CB_2$ play an important role in mediating the antitussive effect of cannabinoids, and $CB_1$-selective agonists and $CB_1/CB_2$ agonists are useful in the treatment and/or prophylaxis of cough.

6. Cancer

A number of human leukemia and lymphoma cell lines, including Jurkat, Molt-4 and Sup-T1, express $CB_2$ and not $CB_1$, and agonists of $CB_2$ induce apoptosis in these and primary acute lymphoblastic leukemia (ALL) cells (Nagarkatti, L. C. et al. US2004/0259936). Similarly, $CB_2$ is expressed on glioblastoma cell lines and treatment with agonists of $CB_2$ induces apoptosis of these cells in vitro (Widmer, M. (2008) J. Neurosci. Res. 86(14):3212-20). Accordingly, $CB_2$-selective agonists are useful in attenuating the growth of a malignancy of the immune system, for example, leukemias, lymphomas, and solid tumors of the glial lineage.

In addition, as discussed above, $CB_1$-selective agonists and $CB_1/CB_2$ agonists are useful in providing relief from pain associated with cancer (GW Pharmaceuticals press release Jan. 19, 2005, Jun. 19, 2007).

$CB_2$-mediated signaling is involved in the in vivo and in vitro growth inhibition of prostate cancer cells, which suggests that $CB_2$ agonists have potential therapeutic interest in the management of prostate cancer. (Inhibition of human tumour prostate PC-3 cell growth by cannabinoids R(+)-Methanandamide and JWH-015: Involvement of $CB_2$; Olea-Herrero, et al. British Journal of Cancer advance online publication 18 Aug. 2009; doi: 10.1038/sj.bjc. 6605248).

7. Regenerative Medicine

Agonists of $CB_2$ modulate the expansion of the progenitor pool of neurons in the CNS. $CB_2$ antagonists inhibit the proliferation of cultured neural stem cells and the proliferation of progenitor cells in the SVZ of young animals, whereas $CB_2$-selective agonists stimulate progenitor cell proliferation in vivo, with this effect being more pronounced in older animals (Goncalves, M. B. et al. (2008) Mol. Cell Neurosci. 38(4):526-36). Thus, agonists of $CB_2$ are useful in regenerative medicine, for example to promote the expansion of progenitor cells for the replacement of neurons lost during injury or disease, such as Alzheimer's Disease, stroke-induced damage, dementia, amyotrophic lateral sclerosis (ALS) and Parkinson's Disease.

8. Certain Embodiments

One aspect of the present invention relates to methods for the treatment of a cannabinoid receptor-mediated disorder in an individual, comprising administering to the individual in need thereof, a therapeutically effective amount of an anhydrous crystalline form as described herein or a pharmaceutical composition thereof.

One aspect of the present invention relates to methods for the treatment of a $CB_2$ receptor-mediated disorder in an individual, comprising administering to the individual in need thereof, a therapeutically effective amount of an anhydrous crystalline form as described herein or a pharmaceutical composition thereof.

One aspect of the present invention relates to methods for the treatment of pain in an individual, comprising administering to the individual in need thereof, a therapeutically effective amount of an anhydrous crystalline form as described herein or a pharmaceutical composition thereof.

One aspect of the present invention relates to methods for the treatment of bone pain in an individual, comprising administering to the individual in need thereof, a therapeutically effective amount of an anhydrous crystalline form as described herein or a pharmaceutical composition thereof.

One aspect of the present invention relates to methods for the treatment of joint pain in an individual, comprising administering to the individual in need thereof, a therapeutically effective amount of an anhydrous crystalline form as described herein or a pharmaceutical composition thereof.

One aspect of the present invention relates to methods for the treatment of pain associated with osteoarthritis in an individual, comprising administering to the individual in need thereof, a therapeutically effective amount of an anhydrous crystalline form as described herein or a pharmaceutical composition thereof.

One aspect of the present invention relates to methods for the treatment of osteoarthritis in an individual, comprising administering to the individual in need thereof, a therapeutically effective amount of an anhydrous crystalline form as described herein or a pharmaceutical composition thereof.

One aspect of the present invention relates to methods for the treatment of osteoporosis in an individual, comprising administering to the individual in need thereof, a therapeutically effective amount of an anhydrous crystalline form as described herein or a pharmaceutical composition thereof.

One aspect of the present invention relates to methods for the treatment of hyperalgesia in an individual, comprising administering to the individual in need thereof, a therapeutically effective amount of an anhydrous crystalline form as described herein or a pharmaceutical composition thereof.

One aspect of the present invention relates to methods for the treatment of allodynia in an individual, comprising administering to the individual in need thereof, a therapeutically effective amount of an anhydrous crystalline form as described herein or a pharmaceutical composition thereof.

One aspect of the present invention relates to methods for the treatment of inflammatory pain in an individual, comprising administering to the individual in need thereof, a therapeutically effective amount of an anhydrous crystalline form as described herein or a pharmaceutical composition thereof.

One aspect of the present invention relates to methods for the treatment of inflammatory hyperalgesia in an individual, comprising administering to the individual in need thereof, a therapeutically effective amount of an anhydrous crystalline form as described herein or a pharmaceutical composition thereof.

One aspect of the present invention relates to methods for the treatment of neuropathic pain in an individual, comprising administering to the individual in need thereof, a therapeutically effective amount of an anhydrous crystalline form as described herein or a pharmaceutical composition thereof.

One aspect of the present invention relates to methods for the treatment of neuropathic hyperalgesia in an individual, comprising administering to the individual in need thereof, a therapeutically effective amount of an anhydrous crystalline form as described herein or a pharmaceutical composition thereof.

One aspect of the present invention relates to methods for the treatment of acute nociception in an individual, comprising administering to the individual in need thereof, a therapeutically effective amount of an anhydrous crystalline form as described herein or a pharmaceutical composition thereof.

One aspect of the present invention relates to methods for the treatment of muscle pain in an individual, comprising administering to the individual in need thereof, a therapeutically effective amount of an anhydrous crystalline form as described herein or a pharmaceutical composition thereof.

One aspect of the present invention relates to methods for the treatment of dental pain in an individual, comprising administering to the individual in need thereof, a therapeutically effective amount of an anhydrous crystalline form as described herein or a pharmaceutical composition thereof.

One aspect of the present invention relates to methods for the treatment of migraine and other headache pain in an individual, comprising administering to the individual in need thereof, a therapeutically effective amount of an anhydrous crystalline form as described herein or a pharmaceutical composition thereof.

One aspect of the present invention relates to methods for the treatment of pain that occurs as an adverse effect of therapeutics in an individual, comprising administering to the individual in need thereof, a therapeutically effective amount of an anhydrous crystalline form as described herein or a pharmaceutical composition thereof.

One aspect of the present invention relates to methods for the treatment of pain associated with a disorder selected from: cancer, multiple sclerosis, allergic reactions, nephritic syndrome, scleroderma, thyroiditis, diabetic neuropathy, fibromyalgia, HIV related-neuropathy, sciatica, and autoimmune conditions, in an individual, comprising administering to the individual in need thereof, a therapeutically effective amount of an anhydrous crystalline form as described herein or a pharmaceutical composition thereof.

One aspect of the present invention relates to methods for the treatment of multiple sclerosis-associated spasticity in an individual, comprising administering to the individual in need thereof, a therapeutically effective amount of an anhydrous crystalline form as described herein or a pharmaceutical composition thereof.

One aspect of the present invention relates to methods for the treatment of autoimmune disorders in an individual, comprising administering to the individual in need thereof, a therapeutically effective amount of an anhydrous crystalline form as described herein or a pharmaceutical composition thereof.

One aspect of the present invention relates to methods for the treatment of an autoimmune disorder selected from the group consisting of: multiple sclerosis, Guillan-Barré syndrome, polyradiculoneuropathy, chronic inflammatory demyelination, rheumatoid arthritis, psoriatic arthritis, ankylosing spondylarthritis, and reactive arthritis, in an individual, comprising administering to the individual in need thereof, a therapeutically effective amount of an anhydrous crystalline form as described herein or a pharmaceutical composition thereof.

One aspect of the present invention relates to methods for the treatment of allergic reactions in an individual, comprising administering to the individual in need thereof, a therapeutically effective amount of an anhydrous crystalline form as described herein or a pharmaceutical composition thereof.

One aspect of the present invention relates to methods for the treatment of an allergic reaction associated with a disorder selected from: atopic dermatitis, pruritis, urticaria, asthma, conjunctivitis, allergic rhinitis, and anaphylaxis in an individual, comprising administering to the individual in need thereof, a therapeutically effective amount of an anhydrous crystalline form as described herein or a pharmaceutical composition thereof.

One aspect of the present invention relates to methods for the treatment of CNS inflammation in an individual, comprising administering to the individual in need thereof, a therapeutically effective amount of an anhydrous crystalline form as described herein or a pharmaceutical composition thereof.

One aspect of the present invention relates to methods for the treatment of CNS inflammation associated with a disorder selected from: Alzheimer's disease, stroke, dementia, amyotrophic lateral sclerosis, and human immnunodeficiency virus, in an individual, comprising administering to the individual in need thereof, a therapeutically effective amount of an anhydrous crystalline form as described herein or a pharmaceutical composition thereof.

One aspect of the present invention relates to methods for the treatment of atherosclerosis in an individual, comprising administering to the individual in need thereof, a therapeutically effective amount of an anhydrous crystalline form as described herein or a pharmaceutical composition thereof.

One aspect of the present invention relates to methods for the treatment of undesired immune cell activity and inflammation associated with a disorder selected from: osteoarthritis, anaphylaxis, Behcet's disease, graft rejection, vasculitis, gout, spondylitis, viral disease, bacterial disease, lupus, inflammatory bowel disease, autoimmune hepatitis, and type 1 diabetes mellitus, in an individual, comprising administering to the individual in need thereof, a therapeutically effective amount of an anhydrous crystalline form as described herein or a pharmaceutical composition thereof.

One aspect of the present invention relates to methods for the treatment of age-related macular degeneration in an individual, comprising administering to the individual in need thereof, a therapeutically effective amount of an anhydrous crystalline form as described herein or a pharmaceutical composition thereof.

One aspect of the present invention relates to methods for the treatment of cough in an individual, comprising administering to the individual in need thereof, a therapeutically effective amount of an anhydrous crystalline form as described herein or a pharmaceutical composition thereof.

One aspect of the present invention relates to methods for the treatment of leukemia in an individual, comprising administering to the individual in need thereof, a therapeutically effective amount of an anhydrous crystalline form as described herein or a pharmaceutical composition thereof.

One aspect of the present invention relates to methods for the treatment of lymphoma in an individual, comprising administering to the individual in need thereof, a therapeutically effective amount of an anhydrous crystalline form as described herein or a pharmaceutical composition thereof.

One aspect of the present invention relates to methods for the treatment of CNS tumors in an individual, comprising administering to the individual in need thereof, a therapeutically effective amount of an anhydrous crystalline form as described herein or a pharmaceutical composition thereof.

One aspect of the present invention relates to methods for the treatment of prostate cancer in an individual, comprising administering to the individual in need thereof, a therapeutically effective amount of an anhydrous crystalline form as described herein or a pharmaceutical composition thereof.

One aspect of the present invention relates to methods for the treatment of Alzheimer's disease in an individual, comprising administering to the individual in need thereof, a therapeutically effective amount of an anhydrous crystalline form as described herein or a pharmaceutical composition thereof.

One aspect of the present invention relates to methods for the treatment of stroke-induced damage in an individual, comprising administering to the individual in need thereof, a therapeutically effective amount of an anhydrous crystalline form as described herein or a pharmaceutical composition thereof.

One aspect of the present invention relates to methods for the treatment of dementia in an individual, comprising administering to the individual in need thereof, a therapeutically effective amount of an anhydrous crystalline form as described herein or a pharmaceutical composition thereof.

One aspect of the present invention relates to methods for the treatment of amyotrophic lateral sclerosis in an individual, comprising administering to the individual in need thereof, a therapeutically effective amount of an anhydrous crystalline form as described herein or a pharmaceutical composition thereof.

One aspect of the present invention relates to methods for the treatment of Parkinson's disease in an individual, comprising administering to the individual in need thereof, a therapeutically effective amount of an anhydrous crystalline form as described herein or a pharmaceutical composition thereof.

One aspect of the present invention relates to the use of an anhydrous crystalline form as described herein, in the manufacture of a medicament for the treatment of a cannabinoid receptor-mediated disorder.

One aspect of the present invention relates to the use of an anhydrous crystalline form as described herein, in the manufacture of a medicament for the treatment of a $CR_2$ receptor-mediated disorder.

One aspect of the present invention relates to the use of an anhydrous crystalline form as described herein, in the manufacture of a medicament for the treatment of pain.

One aspect of the present invention relates to the use of an anhydrous crystalline form as described herein, in the manufacture of a medicament for the treatment of bone pain.

One aspect of the present invention relates to the use of an anhydrous crystalline form as described herein, in the manufacture of a medicament for the treatment of joint pain.

One aspect of the present invention relates to the use of an anhydrous crystalline form as described herein, in the manufacture of a medicament for the treatment of pain associated with osteoarthritis.

One aspect of the present invention relates to the use of an anhydrous crystalline form as described herein, in the manufacture of a medicament for the treatment of osteoarthritis.

One aspect of the present invention relates to the use of an anhydrous crystalline form as described herein, in the manufacture of a medicament for the treatment of osteoporosis.

One aspect of the present invention relates to the use of an anhydrous crystalline form as described herein, in the manufacture of a medicament for the treatment of hyperalgesia.

One aspect of the present invention relates to the use of an anhydrous crystalline form as described herein, in the manufacture of a medicament for the treatment of allodynia.

One aspect of the present invention relates to the use of an anhydrous crystalline form as described herein, in the manufacture of a medicament for the treatment of inflammatory pain.

One aspect of the present invention relates to the use of an anhydrous crystalline form as described herein, in the manufacture of a medicament for the treatment of inflammatory hyperalgesia.

One aspect of the present invention relates to the use of an anhydrous crystalline form as described herein, in the manufacture of a medicament for the treatment of neuropathic pain.

One aspect of the present invention relates to the use of an anhydrous crystalline form as described herein, in the manufacture of a medicament for the treatment of neuropathic hyperalgesia.

One aspect of the present invention relates to the use of an anhydrous crystalline form as described herein, in the manufacture of a medicament for the treatment of acute nociception.

One aspect of the present invention relates to the use of an anhydrous crystalline form as described herein, in the manufacture of a medicament for the treatment of muscle pain.

One aspect of the present invention relates to the use of an anhydrous crystalline form as described herein, in the manufacture of a medicament for the treatment of dental pain.

One aspect of the present invention relates to the use of an anhydrous crystalline form as described herein, in the manufacture of a medicament for the treatment of migraine and other headache pain.

One aspect of the present invention relates to the use of an anhydrous crystalline form as described herein, in the manufacture of a medicament for the treatment of pain that occurs as an adverse effect of therapeutics.

One aspect of the present invention relates to the use of an anhydrous crystalline form as described herein, in the manufacture of a medicament for the treatment of pain associated with a disorder selected from: cancer, multiple sclerosis, allergic reactions, nephritic syndrome, scleroderma, thyroiditis, diabetic neuropathy, fibromyalgia, HIV related-neuropathy, sciatica, and autoimmune conditions.

One aspect of the present invention relates to the use of an anhydrous crystalline form as described herein, in the manufacture of a medicament for the treatment of multiple sclerosis-associated spasticity.

One aspect of the present invention relates to the use of an anhydrous crystalline form as described herein, in the manufacture of a medicament for the treatment of autoimmune disorders.

One aspect of the present invention relates to the use of an anhydrous crystalline form as described herein, in the manufacture of a medicament for the treatment of an autoimmune disorder selected from the group consisting of: multiple sclerosis, Guillan-Barré syndrome, polyradiculoneuropathy, chronic inflammatory demyelination, rheumatoid arthritis, psoriatic arthritis, ankylosing spondylarthritis, and reactive arthritis.

One aspect of the present invention relates to the use of an anhydrous crystalline form as described herein, in the manufacture of a medicament for the treatment of allergic reactions.

One aspect of the present invention relates to the use of an anhydrous crystalline form as described herein, in the manufacture of a medicament for the treatment of an allergic reaction associated with a disorder selected from: atopic dermatitis, pruritis, urticaria, asthma, conjunctivitis, allergic rhinitis, and anaphylaxis.

One aspect of the present invention relates to the use of an anhydrous crystalline form as described herein, in the manufacture of a medicament for the treatment of CNS inflammation.

One aspect of the present invention relates to the use of an anhydrous crystalline form as described herein, in the manufacture of a medicament for the treatment of CNS inflammation associated with a disorder selected from: Alzheimer's disease, stroke, dementia, amyotrophic lateral sclerosis, and human immunodeficiency virus.

One aspect of the present invention relates to the use of an anhydrous crystalline form as described herein, in the manufacture of a medicament for the treatment of atherosclerosis.

One aspect of the present invention relates to the use of an anhydrous crystalline form as described herein, in the manufacture of a medicament for the treatment of undesired immune cell activity and inflammation associated with a disorder selected from: osteoarthritis, anaphylaxis, Behcet's disease, graft rejection, vasculitis, gout, spondylitis, viral disease, bacterial disease, lupus, inflammatory bowel disease, autoimmune hepatitis, and type 1 diabetes mellitus.

One aspect of the present invention relates to the use of an anhydrous crystalline form as described herein, in the manufacture of a medicament for the treatment of age-related macular degeneration.

One aspect of the present invention relates to the use of an anhydrous crystalline form as described herein, in the manufacture of a medicament for the treatment of cough.

One aspect of the present invention relates to the use of an anhydrous crystalline form as described herein, in the manufacture of a medicament for the treatment of leukemia.

One aspect of the present invention relates to the use of an anhydrous crystalline form as described herein, in the manufacture of a medicament for the treatment of lymphoma.

One aspect of the present invention relates to the use of an anhydrous crystalline form as described herein, in the manufacture of a medicament for the treatment of CNS tumors.

One aspect of the present invention relates to the use of an anhydrous crystalline form as described herein, in the manufacture of a medicament for the treatment of prostate cancer.

One aspect of the present invention relates to the use of an anhydrous crystalline form as described herein, in the manufacture of a medicament for the treatment of Alzheimer's disease.

One aspect of the present invention relates to the use of an anhydrous crystalline form as described herein, in the manufacture of a medicament for the treatment of stroke-induced damage.

One aspect of the present invention relates to the use of an anhydrous crystalline form as described herein, in the manufacture of a medicament for the treatment of dementia.

One aspect of the present invention relates to the use of an anhydrous crystalline form as described herein, in the manufacture of a medicament for the treatment of amyotrophic lateral sclerosis.

One aspect of the present invention relates to the use of an anhydrous crystalline form as described herein, in the manufacture of a medicament for the treatment of Parkinson's disease.

One aspect of the present invention relates to an anhydrous crystalline form as described herein, for use in a method of treatment of the human or animal body by therapy.

One aspect of the present invention relates to an anhydrous crystalline form as described herein, for use in a method of treatment of a cannabinoid receptor-mediated disorder.

One aspect of the present invention relates to an anhydrous crystalline form as described herein, for use in a method of treatment of a $CB_2$ receptor-mediated disorder.

One aspect of the present invention relates to an anhydrous crystalline form as described herein, for use in a method of treatment of pain.

One aspect of the present invention relates to an anhydrous crystalline form as described herein, for use in a method of treatment of bone pain.

One aspect of the present invention relates to an anhydrous crystalline form as described herein, for use in a method of treatment of joint pain.

One aspect of the present invention relates to an anhydrous crystalline form as described herein, for use in a method of treatment of pain associated with osteoarthritis.

One aspect of the present invention relates to an anhydrous crystalline form as described herein, for use in a method of treatment of osteoarthritis.

One aspect of the present invention relates to an anhydrous crystalline form as described herein, for use in a method of treatment of osteoporosis.

One aspect of the present invention relates to an anhydrous crystalline form as described herein, for use in a method of treatment of hyperalgesia.

One aspect of the present invention relates to an anhydrous crystalline form as described herein, for use in a method of treatment of allodynia.

One aspect of the present invention relates to an anhydrous crystalline form as described herein, for use in a method of treatment of inflammatory pain.

One aspect of the present invention relates to an anhydrous crystalline form as described herein, for use in a method of treatment of inflammatory hyperalgesia.

One aspect of the present invention relates to an anhydrous crystalline form as described herein, for use in a method of treatment of neuropathic pain.

One aspect of the present invention relates to an anhydrous crystalline form as described herein, for use in a method of treatment of neuropathic hyperalgesia.

One aspect of the present invention relates to an anhydrous crystalline form as described herein, for use in a method of treatment of acute nociception.

One aspect of the present invention relates to an anhydrous crystalline form as described herein, for use in a method of treatment of muscle pain.

One aspect of the present invention relates to an anhydrous crystalline form as described herein, for use in a method of treatment of dental pain.

One aspect of the present invention relates to an anhydrous crystalline form as described herein, for use in a method of treatment of migraine and other headache pain.

One aspect of the present invention relates to an anhydrous crystalline form as described herein, for use in a method of treatment of pain that occurs as an adverse effect of therapeutics.

One aspect of the present invention relates to an anhydrous crystalline form as described herein, for use in a method of treatment of pain associated with a disorder selected from: cancer, multiple sclerosis, allergic reactions, nephritic syndrome, scleroderma, thyroiditis, diabetic neuropathy, fibromyalgia, HIV related-neuropathy, sciatica, and autoimmune conditions.

One aspect of the present invention relates to an anhydrous crystalline form as described herein, for use in a method of treatment of multiple sclerosis-associated spasticity.

One aspect of the present invention relates to an anhydrous crystalline form as described herein, for use in a method of treatment of autoimmune disorders.

One aspect of the present invention relates to an anhydrous crystalline form as described herein, for use in a method of treatment of an autoimmune disorder selected from the group consisting of: multiple sclerosis, Guillan-Barré syndrome, polyradiculoneuropathy, chronic inflammatory demyelination, rheumatoid arthritis, psoriatic arthritis, ankylosing spondylarthritis, and reactive arthritis.

One aspect of the present invention relates to an anhydrous crystalline form as described herein, for use in a method of treatment of allergic reactions.

One aspect of the present invention relates to an anhydrous crystalline form as described herein, for use in a method of treatment of an allergic reaction associated with a disorder selected from: atopic dermatitis, pruritis, urticaria, asthma, conjunctivitis, allergic rhinitis, and anaphylaxis.

One aspect of the present invention relates to an anhydrous crystalline form as described herein, for use in a method of treatment of CNS inflammation.

One aspect of the present invention relates to an anhydrous crystalline form as described herein, for use in a method of treatment of CNS inflammation associated with a disorder selected from: Alzheimer's disease, stroke, dementia, amyotrophic lateral sclerosis, and human immunodeficiency virus.

One aspect of the present invention relates to an anhydrous crystalline form as described herein, for use in a method of treatment of atherosclerosis.

One aspect of the present invention relates to an anhydrous crystalline form as described herein, for use in a method of treatment of undesired immune cell activity and inflammation associated with a disorder selected from: osteoarthritis, anaphylaxis, Behcet's disease, graft rejection, vasculitis, gout, spondylitis, viral disease, bacterial disease, lupus, inflammatory bowel disease, autoimmune hepatitis, and type 1 diabetes mellitus.

One aspect of the present invention relates to an anhydrous crystalline form as described herein, for use in a method of treatment of age-related macular degeneration.

One aspect of the present invention relates to an anhydrous crystalline form as described herein, for use in a method of treatment of cough.

One aspect of the present invention relates to an anhydrous crystalline form as described herein, for use in a method of treatment of leukemia.

One aspect of the present invention relates to an anhydrous crystalline form as described herein, for use in a method of treatment of lymphoma.

One aspect of the present invention relates to an anhydrous crystalline form as described herein, for use in a method of treatment of CNS tumors.

One aspect of the present invention relates to an anhydrous crystalline form as described herein, for use in a method of treatment of prostate cancer.

One aspect of the present invention relates to an anhydrous crystalline form as described herein, for use in a method of treatment of Alzheimer's disease.

One aspect of the present invention relates to an anhydrous crystalline form as described herein, for use in a method of treatment of stroke-induced damage.

One aspect of the present invention relates to an anhydrous crystalline form as described herein, for use in a method of treatment of dementia.

One aspect of the present invention relates to an anhydrous crystalline form as described herein, for use in a method of treatment of amyotrophic lateral sclerosis.

One aspect of the present invention relates to an anhydrous crystalline form as described herein, for use in a method of treatment of Parkinson's disease.

Pharmaceutical Compositions and Dosage Forms

One aspect of the present invention relates to compositions comprising an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein.

One aspect of the present invention relates to compositions comprising an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein, and a pharmaceutically acceptable carrier.

One aspect of the present invention relates to pharmaceutical compositions comprising an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein, and a pharmaceutically acceptable carrier.

One aspect of the present invention relates to dosage forms comprising an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide as described herein, and a pharmaceutically acceptable carrier.

One aspect of the present invention relates to processes for preparing pharmaceutical compositions comprising the steps of:

1) preparing an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide according to any of the processes described herein; and 2) admixing said anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide with a pharmaceutically acceptable carrier.

One aspect of the present invention relates to processes for preparing a dosage form comprising the steps of:

1) preparing an anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide according to any of the processes described herein; and 2) admixing said anhydrous crystalline form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide with a pharmaceutically acceptable carrier.

One aspect of the present invention relates to compositions comprising a solvate as described herein.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape or dispensing into a desired vial or ampule.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosage forms thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate, hydrate or physiologically functional derivative thereof can be used as active ingredients in pharmaceutical compositions, specifically as cannabinoid receptor modulators. By the term "active ingredient" is defined in the context of a "pharmaceutical composition" and refers to a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis conducted or on whether further active compounds are administered in addition to the compounds of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt, solvate or hydrate of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" includes the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dosage form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which can be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dosage form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like. Certain compounds of the present invention which contain a carboxylic acid functional group may optionally exist as pharmaceutically acceptable salts containing non-toxic, pharmaceutically acceptable metal cations and cations derived from organic bases. Representative metals include, but are not limited to, aluminium, calcium, lithium, magnesium, potassium, sodium, zinc and the like. In some embodiments the pharmaceutically acceptable metal is sodium. Representative organic bases include, but are not limited to, benzathine ($N^1,N^2$-dibenzylethane-1,2-diamine), chloroprocaine (2-(diethylamino)ethyl 4-(chloroamino)benzoate), choline, diethanolamine, ethylenediamine, meglumine ((2R,3R,4R,5S)-6-(methylamino)hexane-1,2,3,4,5-pentaol), procaine (2-(diethylalmino)ethyl 4-aminobenzoate), and the like. Certain pharmaceutically acceptable salts are listed in Berge, et al., *Journal of Pharmaceutical Sciences*, 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the cannabinoid receptor modulators are utilized as active ingredients in a pharmaceutical composition, these are not intended for use only in humans, but in other non-human mammals as well. Indeed, recent advances in the area of animal health-care mandate that consideration be given for the use of active agents, such as cannabinoid receptor modulators, for the treatment of a cannabinoid receptor-associated disease or disorder in companionship animals (e.g., cats, dogs, etc.) and in livestock animals (e.g., cows, chickens, etc.) Those of ordinary skill in the art are readily credited with understanding the utility of such compounds in such settings.

Hydrates and Solvates

It is understood that when the phrase "pharmaceutically acceptable salts, solvates, and hydrates" or the phrase "pharmaceutically acceptable salt, solvate, or hydrate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate or hydrate" is used when referring to salts described herein, it embraces pharmaceutically acceptable solvates and/or hydrates of such salts.

It will be apparent to those skilled in the art that the dosage forms described herein may comprise, as the active component, either a compound described herein or a pharmaceutically acceptable salt or as a pharmaceutically acceptable solvate or hydrate thereof. Moreover, various hydrates and solvates of the compounds described herein and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Accordingly, one aspect of the present invention pertains to methods of administering hydrates and solvates of compounds described herein and/or their pharmaceutical acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Polymorphs and Pseudopolymorphs

Polymorphism is the ability of a substance to exist as two or more crystalline phases that have different arrangements and/or conformations of the molecules in the crystal lattice. Polymorphs show the same properties in the liquid or gaseous state but they behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates.

Because water is a constituent of the atmosphere, hydrates of drugs may be formed rather easily.

By way of example, Stahly recently published a polymorph screens of 245 compounds consisting of a "wide variety of structural types" revealed that about 90% of them exhibited multiple solid forms. Overall, approximately half the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7(6), 1007-1026).

Other Utilities

Another object of the present invention relates to radio-labeled compounds of the present invention that would be useful not only in radio-imaging but also in assays, both in vitro and in vivo, for localizing and quantitating cannabinoid receptors in tissue samples, including human and for identifying cannabinoid receptor ligands by inhibition binding of a radio-labeled compound. It is a further object of this invention to develop novel cannabinoid receptor assays of which comprise such radio-labeled compounds.

The present invention embraces isotopically-labeled crystalline forms of the present invention. Isotopically or radio-labeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present invention include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{75}$Br, $^{76}$Br, $^{77}$Br, $^{82}$Br, $^{123}$I, $^{124}$I, $^{125}$I and $^{131}$I. The radionuclide that is incorporated in the instant radio-labeled compounds will depend on the specific application of that radio-labeled compound. For example, for in vitro cannabinoid receptor labeling and competition assays, compounds that incorporate $^{3}$H, $^{14}$C, $^{82}$Br, $^{125}$I, $^{131}$I or $^{35}$S will generally be most useful. For radio-imaging applications $^{11}$C, $^{18}$F, $^{12}$I, $^{123}$I, $^{124}$I, $^{131}$I, $^{75}$Br, $^{76}$Br or $^{77}$Br will generally be most useful.

It is understood that a "radio-labeled" or "labeled compound" is a crystalline form of Compound 1 that has incorporated at least one radionuclide; in some embodiments the radionuclide is selected from the group consisting of $^{3}$H, and $^{14}$C.

Certain isotopically-labeled crystalline forms of the present invention are useful in compound and/or substrate tissue distribution assays. In some embodiments the radionuclide $^{3}$H and/or $^{14}$C isotopes are useful in these studies. Further, substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Isotopically labeled crystalline forms of the present invention can generally be prepared by following procedures analogous to those disclosed in the and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^{3}$H]: This procedure is rather inexpensive and requires precursors containing reducible functional groups such as aldehydes, ketones, lactones, esters and the like.

C. Reduction with Lithium Aluminum Hydride [$^{3}$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^{3}$H]: This procedure is usually employed to prepare O-methyl or N-methyl (3H) products by treating appropriate precursors with high specific activity methyl iodide (3H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A represented procedure was reported by Zhu, G-D. and co-workers in J. Org. Chem., 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_{3}$P)$_{4}$] or through an aryl or heteroaryl lithium, in the presence of a tri-alkyltinhalide or hexaalkylditin [e.g., (CH$_{3}$)$_{3}$SnSn(CH$_{3}$)$_{3}$]. A representative procedure was reported by Le Bas, M.-D. and co-workers in *J. Labelled Compd. Radiopharm.* 2001, 44, S280-S282.

A radiolabeled cannabinoid receptor compound can be used in a screening assay to identify/evaluate compounds. In general terms, a newly synthesized or identified compound (i.e., test compound) can be evaluated for its ability to reduce binding of the "radio-labeled Compound 1" to a cannabinoid receptor. Accordingly, the ability of a test compound to compete with the "radio-labeled Compound 1" for the binding to a cannabinoid receptor directly correlates to its binding affinity.

Certain labeled compounds of the present invention bind to certain cannabinoid receptors. In one embodiment the labeled compound has an IC$_{50}$ less than about 500 μM, in another embodiment the labeled compound has an IC$_{50}$ less than about 100 μM, in yet another embodiment the labeled compound has an IC$_{50}$ less than about 10 μM, in yet another embodiment the labeled compound has an IC$_{50}$ less than about 1 μM and in still yet another embodiment the labeled inhibitor has an IC$_{50}$ less than about 0.1 μM.

Other uses of the disclosed receptors and methods will become apparent to those skilled in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are illustrative and not limiting.

EXAMPLES

Example 1: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 1)

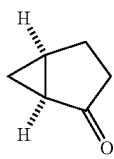

Step A: Preparation of (1S,5R)-bicyclo[3.1.0]hexan-2-one

A 2.5 M hexane solution of n-BuLi (489 mL, 1223 mmol) was added dropwise to a stirred solution of (S)-2-(but-3-enyl)oxirane (100 g, 1019 mmol) and 2,2,6,6-tetramethylpiperidine (86 mL, 509 mmol) in MTBE (1000 mL) cooled in a dry ice/acetone bath, at a rate to maintain the internal temperature at −12 to −5° C. (time of addition=1 h). After addition was complete, the reaction was stirred another hour at −5 to 0° C.

While still at 0° C., 3 M aqueous HCl (545 mL) was added (dropwise at first) with stirring (internal temperature rose to 3° C.). The layers were separated and the organic layer washed with another 200 mL 3 M HCl. The combined aqueous washings were extracted with MTBE (2×500 mL). The combined organic layers were washed with brine (3×300 mL) then concentrated (at 350 mbar and 29° C. water bath) to ca 1000 mL of pale yellow solution. This solution was carried on without further purification.

To 407 mL water was added dibasic potassium phosphate (216 g, 1240 mmol), monobasic potassium phosphate (12.8 g, 94 mmol), and potassium bromide (18.19 g, 153 mmol). pH paper indicated a pH of ~9. This aqueous solution was added to the MTBE solution of (1S,2S,5R)-bicyclo[3.1.0]hexan-2-ol in a 5 L 3-neck round bottom flask equipped with an overhead stirrer. The mixture was cooled to −20° C. in a dry-ice/isopropanol bath. TEMPO (4.30 g, 27.5 mmol) was added. The temperature was allowed to warm to 0° C. and aqueous 10-13% sodium hypochlorite (1059 mL, 1630 mmol) was added dropwise while maintaining the internal temperature between −10 and 0° C. (time of addition=70 min). Stirring was continued at 0° C. for another hour. 50 g sodium sulfite was added to quench excess sodium hypochlorite (temperature rose to 12° C.). The layers were separated and the aqueous layer was extracted twice more with MTBE (500 mL then 250 mL). The combined organic layers (total volume ca 1600 mL) were dried (MgSO$_4$) then filtered. The solution was concentrated to ca 300 mL at 300 mbar and 35° C. water bath. The product was distilled—first with house vacuum and a 50° C. water bath which distilled off most of the remaining MTBE. The vacuum pump was connected giving a vacuum of ~2 torr and the product distilled (2 torr/36° C.) to give the title compound (65.8 g) as a light orange oil (note: receiving flask was cooled in dry ice/acetone bath). $^1$H NMR (400 MHz, CDCl$_3$) δ 0.93 (td, J=4.6, 3.3 Hz, 1H), 1.20 (td, J=8.0, 4.8 Hz, 1H), 1.74-1.79 (m, 1H), 1.98-2.19 (m, 5H).

Step B: Preparation of 2-Hydrazinylpyrazine

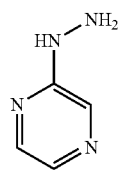

The reaction was run under nitrogen atmosphere. 2-chloropyrazine (96 mL, 1073 mmol) was added dropwise to 35 wt % aqueous hydrazine (544 mL, 6009 mmol) at 65° C. over 1 h. After the addition, stirring was continued at 63-67° C. for 16 h then let stand at room temperature for two days. The mixture was filtered to remove a small amount of precipitate, then extracted with 10% iPrOH/dichloromethane (5×250 mL). The combined organic extracts were dried (MgSO$_4$), filtered, then concentrated under reduced pressure. The resulting solid was triturated with isopropyl acetate (600 mL). The solid was collected by filtration, rinsed with isopropyl acetate and dried under vacuum to give 2-hydrazinylpyrazine (60 g, 51%) as a pale yellow solid. LCMS m/z=111.2 [M+H]$^+$. $^1$H NMR (400 MHz, DMSO-d$_6$) δ 4.21 (s, 2H), 7.70 (d, J=2.8 Hz, 1H), 7.89 (s, 1H), 7.93 (dd, J=2.8, 1.5 Hz, 1H), 8.10 (d, J=1.5 Hz, 1H).

Step C: Preparation of (1aS,5aS)-2-(Pyrazin-2-yl)-1a,2,5,5a-tetrahydro-1H-2,3-diaza-cyclopropa[a]pentalene-4-carboxylic Acid Ethyl Ester

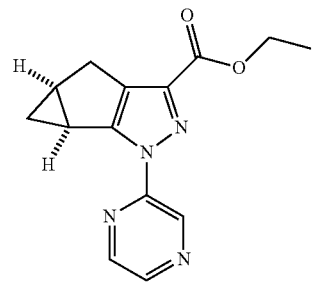 [SMILES: CCOC(=O)c1nn(-c2cnccn2)c2c1C[C@@H]1C[C@H]21]

To a solution of (1S,5R)-bicyclo[3.1.0]hexan-2-one (52.9 g, 539 mmol) and diethyl oxalate (0.073 L, 539 mmol) in absolute ethanol (0.9 L) (not denatured with methanol) was added a 1.0 M THF solution of potassium tert-butoxide (0.539 L, 539 mmol) over 15 min (maintaining the temperature below 43° C.). The resulting yellow solution was stirred at 40° C. for 3.5 h (a precipitate appeared within 10 min and the reaction eventually became a thick suspension). 2-hydrazinylpyrazine (59.4 g, 539 mmol) was added followed by a 6.0 M aqueous solution of hydrogen chloride (0.270 L, 1618 mmol). The reaction was stirred at 50° C. for 1.5 h. The mixture was poured into ice-water (5 L). A precipitate appeared immediately. After standing for 30 minutes in an ice bath, the solid was collected by filtration, rinsed with water (5×1 L), then dried, affording the title product (106 g, 73%) as an off-white solid. LCMS m/z=271.2 (M+H⁺). $^1$H NMR (400 MHz, CDCl$_3$) δ 0.47 (td, J=4.7, 3.3 Hz, 1H), 1.27 (td, J=8.0, 4.9 Hz, 1H), 1.41 (t, J=7.1 Hz, 3H), 2.26-2.32 (m, 1H), 2.77-2.82 (m, 1H), 2.88 (dd, J=16.7, 1.4 Hz, 1H), 2.99 (dd, J=16.6, 6.4 Hz, 1H), 4.40 (q, J=7.1 Hz, 2H), 8.41 (dd, J=2.5, 1.5 Hz, 1H), 8.52 (d, J=2.5 Hz, 1H), 9.40 (d, J=1.5 Hz, 1H).

Step D: Preparation of (1aS,5aS)-2-(Pyrazin-2-yl)-1a,2,5,5a-tetrahydro-1H-2,3-diaza-cyclopropa[a]pentalene-4-carboxylic Acid

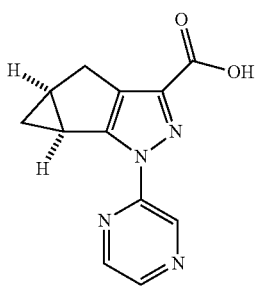 [SMILES: O=C(O)c1nn(-c2cnccn2)c2c1C[C@@H]1C[C@H]21]

To a suspension of (1aS,5aS)-2-(pyrazin-2-yl)-1a,2,5,5a-tetrahydro-1H-2,3-diaza-cyclopropa[a]pentalene-4-carboxylic acid ethyl ester (106 g, 392 mmol) in MeOH (300 mL) and THF (300 mL) was added a 2.0 M aqueous solution of NaOH (235 mL, 471 mmol). The mixture was stirred at 23° C. for 20 h. The organic solvents were removed by distillation. The remaining aqueous solution was diluted with water to ca 1.5 L then acidified to pH ~2 with 6 M HCl (ca 95 mL). The resulting fine precipitate was collected by filtration, rinsed with water, then dried, to give the title compound (95 g, 100%) as a white solid. LCMS m/z=243.1 (M+H⁺). $^1$H NMR (400 MHz, DMSO-d6) δ 0.43 (td, J=4.6, 3.2 Hz, 1H), 1.26 (td, J=8.0, 4.4 Hz, 1H), 2.27-2.33 (m, 1H), 2.71-2.75 (m, 1H), 2.76 (d, J=16.8 Hz, 1H), 2.89 (dd, J=16.4, 6.4 Hz, 1H), 8.61 (dd, J=2.7, 1.5 Hz, 1H), 8.67 (d, J=2.5 Hz, 1H), 9.17 (d, J=1.5 Hz, 1H), 13.02 (s, 1H).

Two separate methods were used to prepare Compound 1, one method oxidized the pyrazinyl ring nitrogen as the last reaction step while the second method oxidized the pyrazinyl ring nitrogen of the carboxylic acid intermediate (i.e., title compound in of Step D) prior to the coupling with (S)-2-amino-3,3-dimethylbutan-1-ol. Steps E and F are shown below.

Method 1

Step E: Preparation of (1aS,5aS)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide

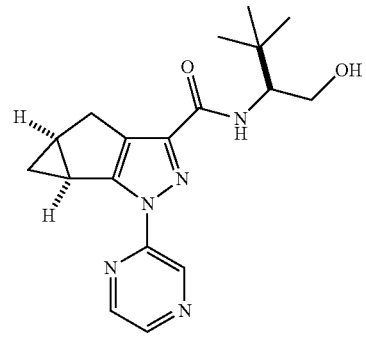 [SMILES: CC(C)(C)[C@@H](CO)NC(=O)c1nn(-c2cnccn2)c2c1C[C@@H]1C[C@H]21]

To a solution of (1aS,5aS)-2-(pyrazin-2-yl)-1a,2,5,5a-tetrahydro-1H-2,3-diaza-cyclopropa[a]pentalene-4-carboxylic acid (1.4 g, 5.78 mmol) and triethylamine (1.611 mL, 11.56 mmol) in DMF (15 mL) was added HATU (2.242 g, 5.90 mmol). The reaction was stirred at 23° C. for 5 min, then was added (S)-2-amino-3,3-dimethylbutan-1-ol (0.711 g, 6.07 mmol). The reaction was stirred at 23° C. for 15 min then concentrated. The residue was purified by silica gel flash chromatography (35 to 100% EtOAc/hexanes) to give the title product (1.97 g, 100%) as a white solid. LCMS m/z=342.2 [M+H]+. $^1$H NMR (400 MHz, CDCl$_3$) δ 0.48 (td, J=4.6, 3.4 Hz, 1H), 1.05 (s, 9H), 1.24 (td, J=8.0, 4.7 Hz, 1H), 2.26-2.32 (m, 1H), 2.74-2.78 (m, 1H), 2.94 (d, J=16.8 Hz, 1H), 3.01 (dd, J=16.7, 6.1 Hz, 1H), 3.67-3.72 (m, 1H), 3.93-3.98 (m, 2H), 7.08 (d, J=8.5 Hz, 1H), 8.42 (dd, J=1.4, 0.9 Hz, 1H), 8.51 (d, J=2.7 Hz, 1H), 9.26 (d, J=1.1 Hz, 1H).

Step F: Preparation of (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1)

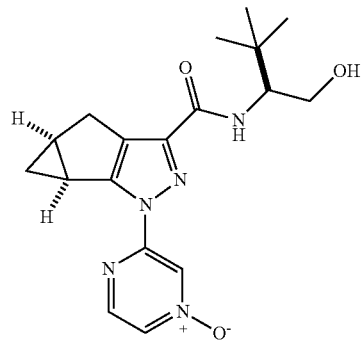

To a solution of (1aS,5aS)-2-pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide (900 mg, 2.64 mmol) in chloroform (10 mL) was added 3-chlorobenzoperoxoic acid (1772 mg, 7.91 mmol). The reaction was stirred at 23° C. for 3 h. Additional MCPBA (1.2 g) was added and stirring was continued at room temperature for 18 h. The mixture was purified by silica gel column chromatography to give the title compound (550 mg) as a white solid. LCMS m/z=358.3 [M+H]$^+$; $^1$H NMR (400 MHz, CDCl$_3$) δ ppm 0.49 (td, J=4.6, 3.3 Hz, 1H), 1.03 (s, 9H), 1.27 (td, J=8.0, 4.9 Hz, 1H), 2.08 (bs, 1H), 2.27-2.33 (m, 1H), 2.71-2.76 (m, 1H), 2.93 (d, J=16.8 Hz, 1H), 3.00 (dd, J=16.7, 6.1 Hz, 1H), 3.65-3.71 (m, 1H), 3.92-3.97 (m, 2H), 6.97 (d, J=8.5 Hz, 1H), 7.99 (dd, J=4.0, 1.4 Hz, 1H), 8.28 (d, J=4.2 Hz, 1H), 8.78 (dd, J=1.4, 0.8 Hz, 1H).

A sample was recrystallized from CH$_2$Cl$_2$/hexane to give a crystalline solvate. A thermogravimetric analysis (TGA) thermogram for this solvate showed a loss of ~5% weight occurring with a melting endotherm at 164° C.

A non-solvated form of Compound 1 was slurried in CH$_2$Cl$_2$ and stirred at ~28° C. overnight. The suspension was filtered using a centrifuge filter and air dried prior to powder X-ray diffraction (PXRD) pattern analysis. The PXRD pattern showed that the material following the CH$_2$Cl$_2$ slurry was indistinguishable from the original solvate form that resulted from recrystallization with CH$_2$Cl$_2$/hexane. The differential scanning calorimetry (DSC) thermogram and thermogravimetric analysis (TGA) thermogram for the crystalline CH$_2$Cl$_2$ solvate obtained from recrystallization using CH$_2$Cl$_2$/hexane is shown in FIG. 1; and the PXRD pattern for each of the crystalline CH$_2$Cl$_2$ solvates obtained from the two different methods (i.e., recrystallization using CH$_2$Cl$_2$/hexane; and non-solvated Compound 1 slurried in CH$_2$Cl$_2$) is shown as an overlay in FIG. 2.

Method 2

Step E: Preparation of (1aS,5aS)-2-(Pyrazin-2-yl)-1a,2,5,5a-tetrahydro-1H-2,3-diaza-cyclopropa[a]pentalene-4-carboxylic Acid N-oxide

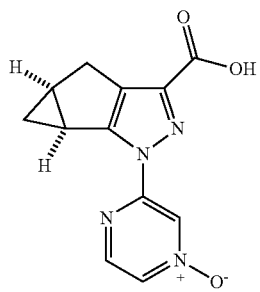

To a suspension of (1aS,5aS)-2-(pyrazin-2-yl)-1a,2,5,5a-tetrahydro-1H-2,3-diaza-cyclopropa[a]pentalene-4-carboxylic acid (68.8 g, 284 mmol) in formic acid (688 mL) was added a 50 wt % aq solution of hydrogen peroxide (82 mL, 1420 mmol) at room temperature. The mixture was heated to 64° C. The reaction was stirred at 58 to 64° C. for 3 h. Another 8 mL 50% H$_2$O$_2$ was added and stirring was continued another hour at 60° C. The mixture was let cool to room temperature and diluted with 1 L water. After storing in an ice bath for 1 h, the precipitate was collected by filtration, rinsed with water and dried under vacuum to give the title compound (56.7 g) as a pale yellow solid which contains 2% starting material by $^1$H NMR. The material was re-subjected to reaction conditions aforementioned to give the title compound (45 g). LCMS m/z=259.2 [M+H]$^+$; $^1$H NMR (400 MHz, DMSO-d$_6$) δ 0.42 (td, J=4.4, 3.3 Hz, 1H), 1.27 (td, J=7.8, 4.7 Hz, 1H), 2.27-2.33 (m, 1H), 2.68-2.73 (m, 1H), 2.75 (dd, J=16.9, 1.5 Hz, 1H), 2.88 (dd, J=16.4, 6.4 Hz, 1H), 8.33 (dd, J=4.2, 1.5 Hz, 1H), 8.50 (dd, J=4.2, 0.6 Hz, 1H), 8.54 (dd, J=1.5, 0.6 Hz, 1H), 13.08 (s, 1H).

Step F: Preparation of (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1)

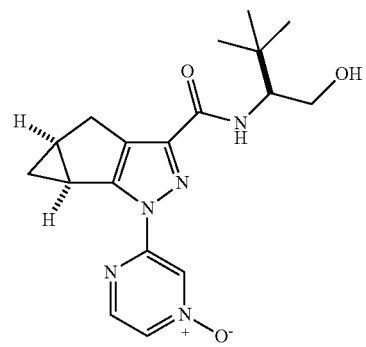

To a suspension of (1aS,5aS)-2-(pyrazin-2-yl)-1a,2,5,5a-tetrahydro-1H-2,3-diaza-cyclopropa[a]pentalene-4-carboxylic acid N-oxide (46.82 g, 181 mmol), (S)-2-amino-3,3-dimethylbutan-1-ol (23.37 g, 199 mmol) and triethylamine (76 mL, 544 mmol) in DMF (400 mL) was added HATU (76 g, 199 mmol). The reaction was stirred at 23° C. for 60 min and concentrated. 0.5 M HCl (500 mL) was added. The mixture was extracted with dichloromethane (3×400 mL). The combined organic extracts were washed with saturated NaHCO$_3$ (2×250 mL), dried (MgSO$_4$), filtered, then concentrated to ~250 mL. To the resulting slurry was added 500 mL of hexanes. The mixture was let stand at room temperature for several hours and the solid was collected by filtration to give the title compound (55 g) as an off-white solid. This material was recrystallized from DCM/hexanes to give the title compound (43.5 g) as a white solid (after drying in vacuum oven at ~65° C. for 10 days). LCMS m/z=358.3 [M+H]$^+$; $^1$H NMR (400 MHz, CDCl$_3$) δ ppm 0.49 (td, J=4.6, 3.3 Hz, 1H), 1.03 (s, 9H), 1.27 (td, J=8.0, 4.9 Hz, 1H), 2.08 (bs, 1H), 2.27-2.33 (m, 1H), 2.71-2.76 (m, 1H), 2.93 (d, J=16.8 Hz, 1H), 3.00 (dd, J=16.7, 6.1 Hz, 1H), 3.65-3.71 (m, 1H), 3.92-3.97 (m, 2H), 6.97 (d, J=8.5 Hz, 1H), 7.99 (dd, J=4.0, 1.4 Hz, 1H), 8.28 (d, J=4.2 Hz, 1H), 8.78 (dd, J=1.4, 0.8 Hz, 1H).

Example 2: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 1, DCM Solvate)

The DCM hemi-solvate (10.6% by weight) was obtained by slow crystallization from CH$_2$Cl$_2$ and hexanes and the crystal structure of this material was solved, see FIG. 3. Further attempts to isolate the hemi-DCM solvate by forming a slurry of Compound 1 with DCM resulted in substantially the same DCM Solvates as disclosed in International Publication Number WO2011/025541, an overlay of the PXRDs of the previous disclosed DCM solvate is shown in FIG. 2.

Example 3: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 1, Anhydrous Form)

Figure 4:
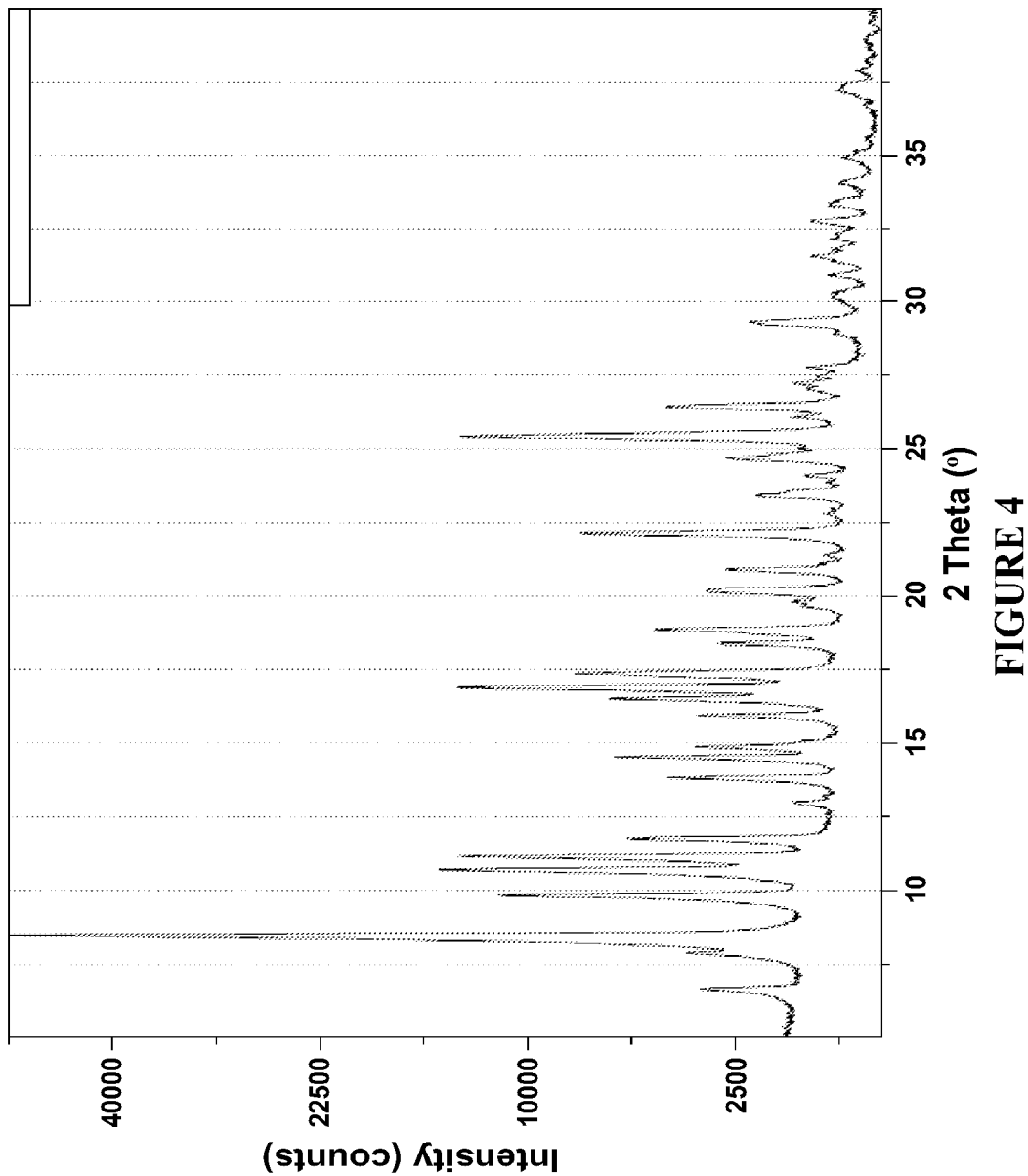
FIG. 4 shows a powder X-ray diffraction (PXRD) pattern for a sample containing an anhydrous crystalline form of Compound 1.
Figure 5:
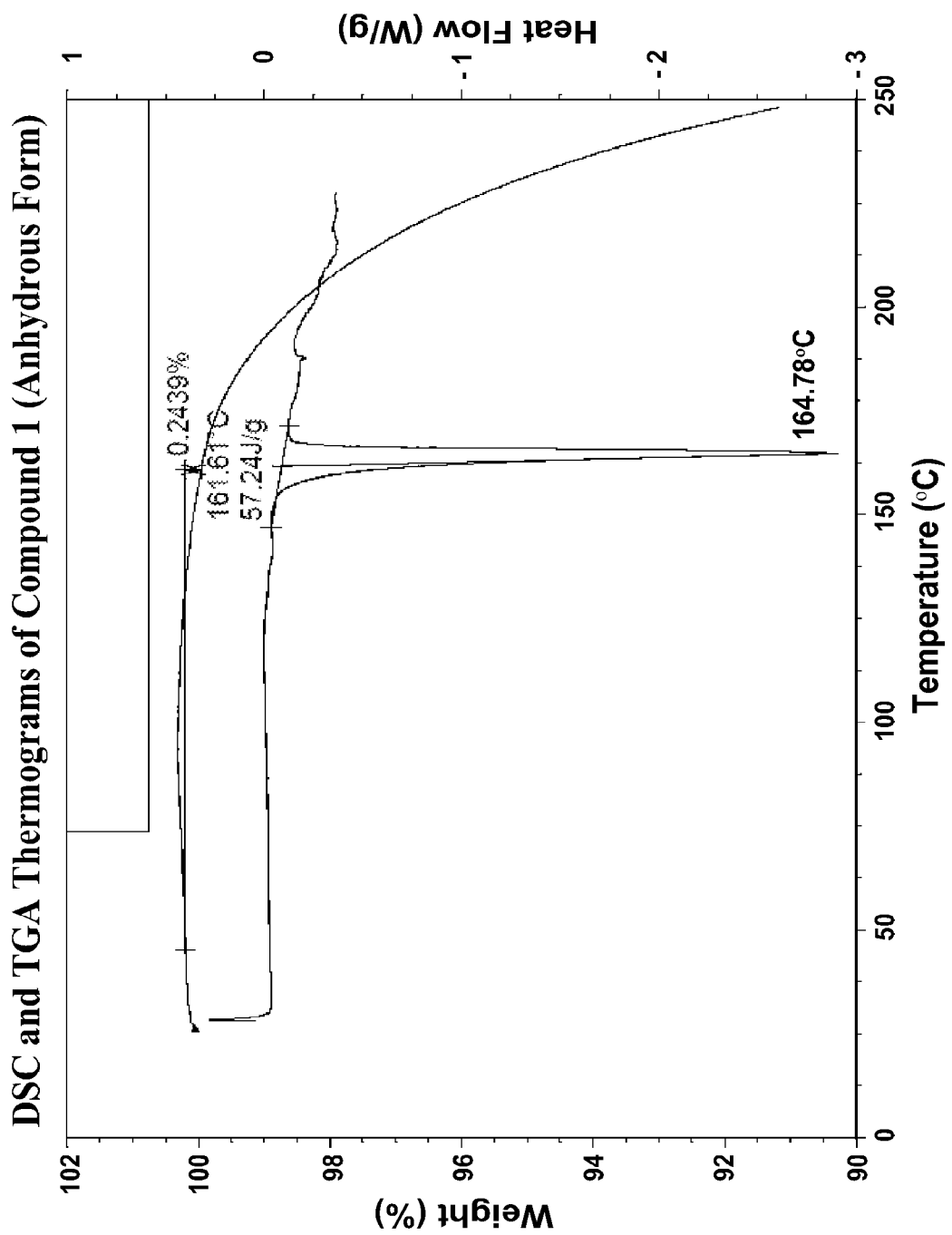
FIG. 5 shows a differential scanning calorimetry (DSC) thermogram for a sample containing anhydrous crystalline form of Compound 1 and a thermogravimetric analysis (TGA) thermogram of a sample containing anhydrous crystalline form of Compound 1.

The anhydrous form of Compound 1 was prepared by recrystallization in DCM and hexanes. The PXRD pattern was characterized, see FIG. 4. This material melts at ~162° C. and is a non-solvated form based on TGA FIG. 5.

It should be noted that the use of mixtures of DCM/hexanes as recrystallizing solvents have been observed at different times to provide different crystal forms.

Example 4: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 1, Anhydrous Form)

Method 1

To a 4 L reactor equipped with an overhead stirrer, chiller/heater, and a dropping funnel was added (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1, 145 g, 406 mmol), acetonitrile (205 mL, 3925 mmol), and water (290 mL). The mixture was heated to 60° C. and then stirred for 60 min. To the resulting reaction was added an additional amount of water (2900 mL), cooled to 0° C., and allowed to stir for 4 h. The mixture was filtered, the solids washed with water and dried under vacuum at 50° C. to provide Compound 1 as the anhydrous form, the material was characterized by PXRD (FIG. 6), and DSC/TGA (FIG. 7).

Method 2

The anhydrous form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1) was prepared in a similar manner as described in Method 1 except that after isolating crystalline (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide from the acetonitrile/water crystallizing mixture the material was dried under vacuum at 60° C.±5° C. to provide Compound 1 as the anhydrous form. The anhydrous form prepared according to Method 2 was characterized by PXRD, DSC, and TGA and was found to be substantially similar to the material prepared according to Method 1.

Example 5: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 1, Acetone Solvate)

The Acetone Solvate of Compound 1 was prepared from a slurry of Compound 1 in acetone. The PXRD pattern was characterized, see FIG. 8. This material showed a loss of weight by TGA of about 5.5%, a desolvation endotherm began at about 100° C. and subsequent melting onset endotherm temperate at about 163° C., see FIG. 9. The acetone solvate was reproduced from a different lot of anhydrous Compound 1, the PXRD is substantially identical to that seen in FIG. 8 but with a different loss of acetone as shown by TGA, and thus the stoichiometry of this solvate can be characterized as a variable or non-stoichiometric acetone solvate of Compound 1.

Example 6: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 1, Non-Selective Solvates)

Figure 14:
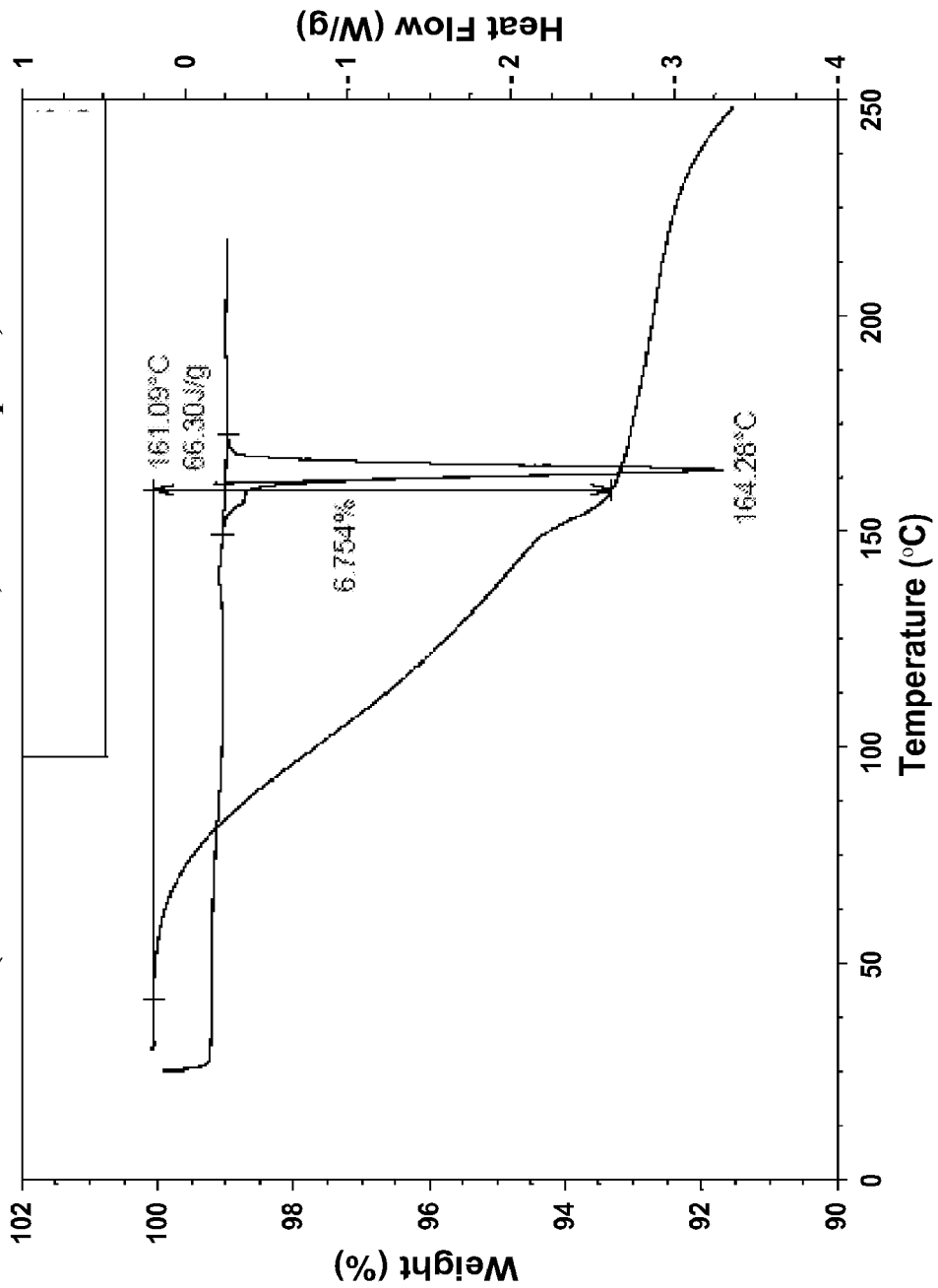
FIG. 14 shows a differential scanning calorimetry (DSC) thermogram for a sample containing a crystalline form of Compound 1 (non-selective solvate) and a thermogravimetric analysis (TGA) thermogram of a sample containing a crystalline form of Compound 1 (non-selective solvate), see Example 6.

The solvate of Compound 1 was prepared from a slurry of Compound 1 in ethyl acetate. The PXRD pattern was characterized, see FIG. 10. The substantially identical PXRD pattern was twice generated from material prepared by slurring Compound 1 in THF, see FIG. 11. Further, the substantially identical PXRD pattern was twice generated from material prepared by slurring Compound 1 in methyl ethyl ketone (MEK), see FIG. 12. Further, the non-selective solvate of Compound 1 prepared using ethyl acetate showed a weight loss of weight of about 4.8% up to about 150° C. with an extrapolated onset temperature of 160.8° C.; see TGA and DSC (FIG. 13). The non-selective solvate of Compound 1 prepared using THF showed a weight loss of about 6.8% up to about 150° C. with an extrapolated onset temperature of 161.0° C.; see TGA and DSC (FIG. 14). The non-selective solvate of Compound 1 prepared using MEK showed a weight loss of about 4.5% up to about 150° C. with an extrapolated onset temperature of 160.5° C.; see TGA and DSC (FIG. 15).

Figure 11:
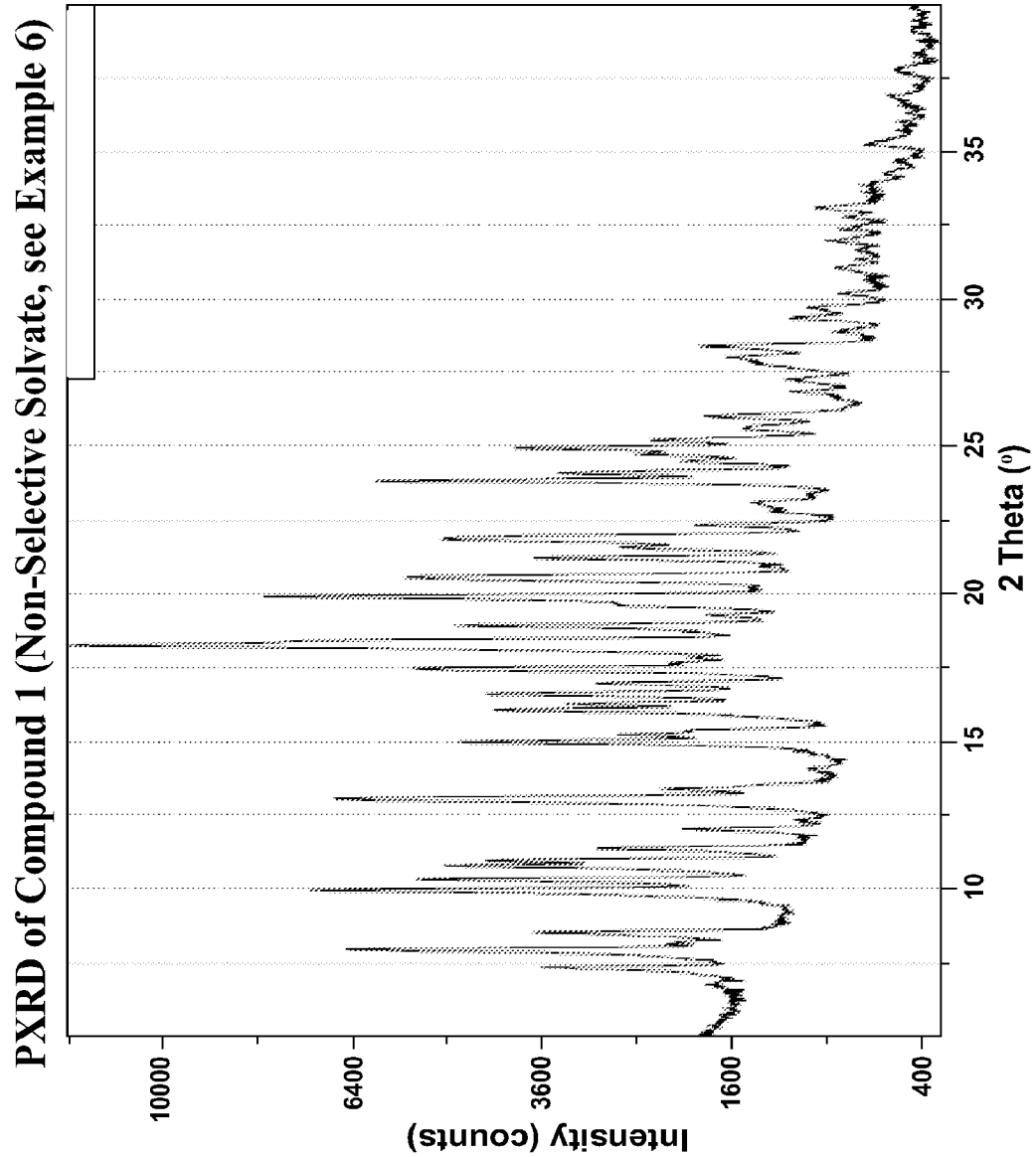
FIG. 11 shows a powder X-ray diffraction (PXRD) pattern for a sample containing a crystalline form of Compound 1 (non-selective solvate), see Example 6.
Figure 12:
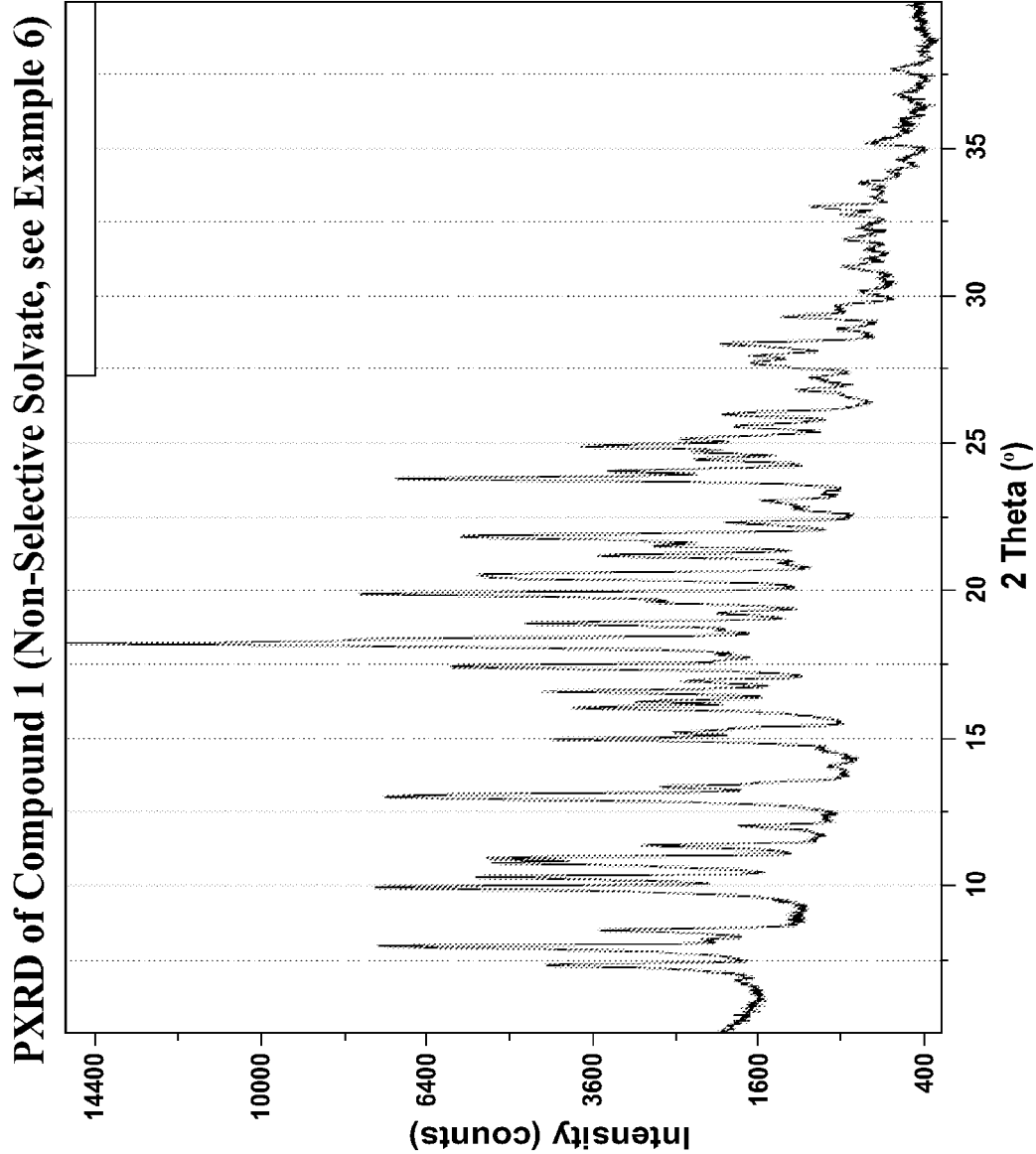
FIG. 12 shows a powder X-ray diffraction (PXRD) pattern for a sample containing a crystalline form of Compound 1 (non-selective solvate), see Example 6.
Figure 15:
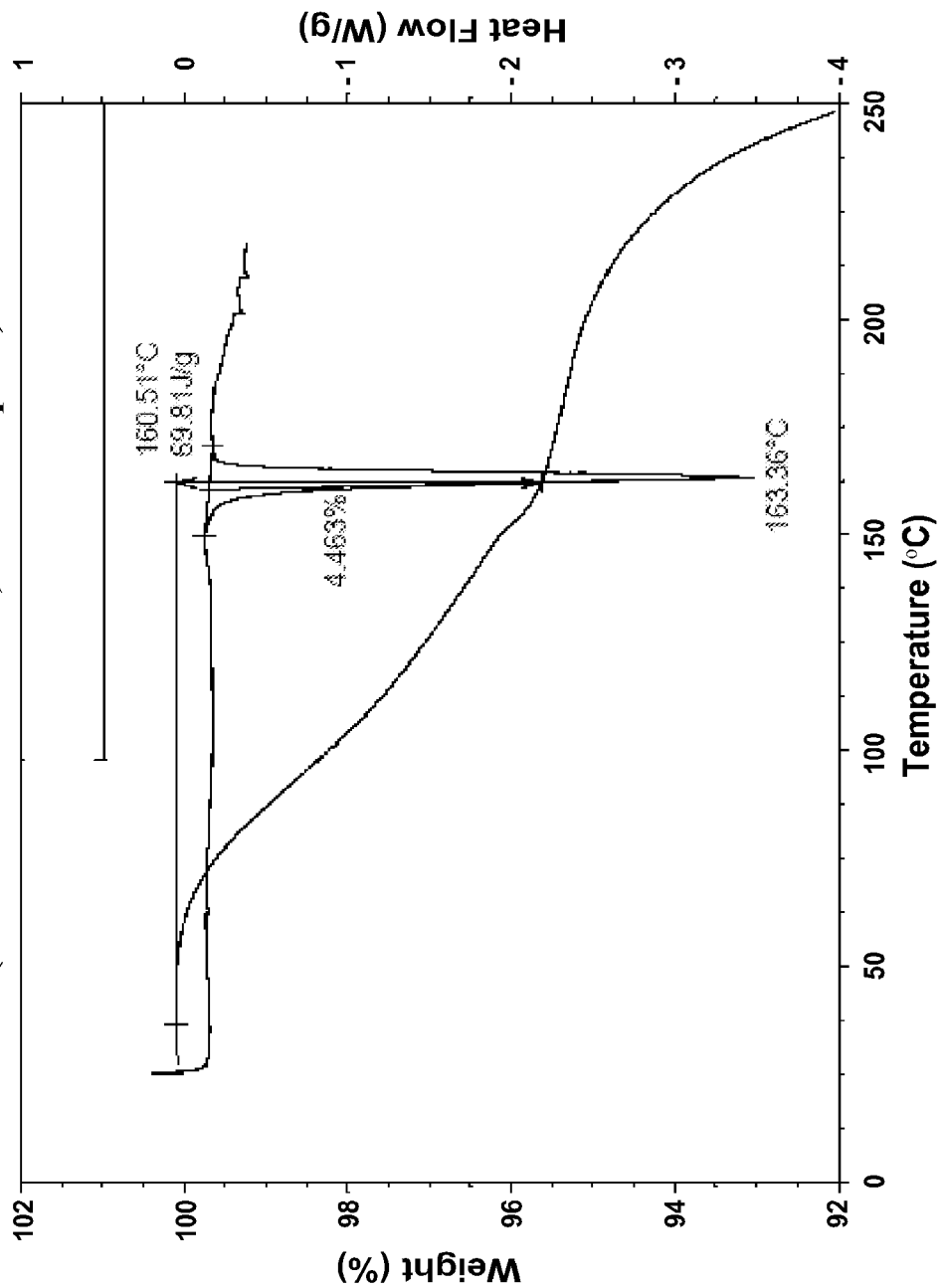
FIG. 15 shows a differential scanning calorimetry (DSC) thermogram for a sample containing a crystalline form of Compound 1 (non-selective solvate) and a thermogravimetric analysis (TGA) thermogram of a sample containing a crystalline form of Compound 1 (non-selective solvate), see Example 6.

The non-selective solvates of Compound 1, independent of the solvent used to prepare the solvate, showed substantially the same PXRD as seen in FIGS. 10, 11, and 12 and after desolvation of the solvate each melts with an extrapolated onset temperature of about 161° C., see FIGS. 13, 14, and 15. These solvates appear to be a non-stoichiometric, non-selective solvate crystalline forms of Compound 1 based on TGA.

Example 7: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 1, Ethyl Acetate Solvate)

A ethyl acetate solvate of Compound 1 was prepared by recrystallization from ethyl acetate and heptane. (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 1, 430-580 mmol) was dissolved in ethyl acetate (450 mL) at 45° C. The mixture was then cooled to 25° C. and 100 mL of heptane was added to the reactor. The mixture was allowed to stir for 20 min at 22° C. Heptane (2250 mL) was then charged and heated to 55° C. The mixture was allowed to stir overnight at 25° C. The reaction was then cooled to 20° C. and then filtered and washed with 500 mL heptane. The filter cake was dried under vacuum at 45° C. The PXRD pattern was characterized, see FIG. 16. The ethyl acetate solvate showed a broad desolvation endotherm from about 30-110° C., corresponding to a 1% weight loss on the TGA, see FIG. 17. There is a second, larger desolvation/melting endotherm at about 115-135° C., corresponding to a TGA weight loss of about 4%. The combined weight loss is consistent with the NMR, which showed approximately 17 mole percent of ethyl acetate, which is equivalent to about 4.7% by weight. This solvate can contain a trace amount of heptane.

Example 8: PathHunter β-Arrestin Assay

A: $CB_2$ Assay

Compound 1 was screened for agonist activity against the human $CB_2$ receptor using the DiscoveRx PathHunter β-arrestin assay which measures the β-arrestin binding to the $CB_2$ receptor upon its activation. $CB_2$ was cloned into the pCMV-PK vector (DiscoveRx, Fremont, Calif.; catalog #93-0167) and transfected into the CHO-K1 EA-Arrestin parental cell line (DiscoveRx, Fremont, Calif.; catalog #93-0164). CHO-K1 positive clones stably expressing the $CB_2$—ProLink fusion protein were identified by their responses to the $CB_2$ agonist CP55,940. Clone #61 was chosen for its big agonist window and homogenous expression as detected by anti-HA flow cytometry Principle of the Assay:

The PathHunter β-arrestin assay measures the interaction of β-arrestin with activated GPCRs using Enzyme Fragment Complementation (Yan et al., *J. Biomol. Screen.* 7: 451-459, 2002). A small, 42 amino acid β-galactosidase fragment, Prolink, is fused to the c-terminus of a GPCR, and β-arrestin is fused to the larger β-galactosidase fragment, EA (Enzyme Acceptor). Binding of β-arrestin to the activated GPCR causes the complementation of the two enzyme fragments, forming an active β-galactosidase enzyme which can be measured using the chemiluminiescent PathHunter Flash Detection Kit (DiscoveRx, Fremont, Calif.: catalog #93-0001).

The Assay:

The stable CHO-K1 cells expressing $CB_2$-Prolink fusion protein were plated over night in 384-well plates (Optiplate 384-Plus, PerkinElmer, Fremont Calif.; catalog #6007299) at 5000 cells/5 μL/well in the Opti-MEM medium (Invitrogen, Carlsbad, Calif.; catalog #31985088) with 1% FBS. 5 uL of test compound diluted in Opti-MEM supplemented with 1% BSA was transferred to each well of the Optiplate. The plates were then incubated at 37° C./5% $CO_2$ for two hours. 12 μL of substrate prepared from the PathHunter Flash Detection Kit (DiscoveRx, Fremont, Calif.: catalog #93-0001) was transferred to each well of the Optiplate. The plate was then incubated in the dark at room temperature for 2 h, after which the assay plate was read.

Assay Readout:

β-Arrestin assay readout was accomplished using a PHERAstar (BMG Labtech Inc., Durham, N.C.) or an EnVision™ (PerkinElmer, Fremont Calif.) microplate reader.

B: $CB_1$ Assay

Compound 1 was screened for agonist activity against the human $CB_1$ receptor using the DiscoveRx PathHunter β-arrestin assay which measures the β-arrestin binding to the $CB_1$ receptor upon its activation. $CB_1$ was cloned into the pCMV-PK vector (DiscoveRx, Fremont, Calif.; catalog #93-0167) and transfected into the CHO-K1 EA-Arrestin parental cell line (DiscoveRx, Fremont, Calif.; catalog #93-0164). CHO-K1 positive clones stably expressing the $CB_1$-ProLink fusion protein were identified by their responses to the $CB_1$ agonist CP55,940. Clone #3 was chosen for its big agonist window and homogenous expression as detected by anti-HA flow cytometry Principle of the Assay:

The PathHunter β-arrestin assay measures the interaction of β-arrestin with activated GPCRs using Enzyme Fragment Complementation (Yan et al., *J. Biomol. Screen.* 7: 451-459, 2002). A small, 42 amino acid β-galactosidase fragment, Prolink, is fused to the c-terminus of a GPCR, and β-arrestin is fused to the larger β-galactosidase fragment, EA (Enzyme Acceptor). Binding of β-arrestin to the activated GPCR causes the complementation of the two enzyme fragments, forming an active β-galactosidase enzyme which can be measured using the chemiluminiescent PathHunter Flash Detection Kit (DiscoveRx, Fremont, Calif.: catalog #93-0001).

The Assay:

The stable CHO-K1 cells expressing $CB_1$—Prolink fusion protein were plated over night in 384-well plates (Optiplate 384-Plus, PerkinElmer, Fremont Calif.; catalog #6007299) at 5000 cells/5 μL/well in the Opti-MEM medium (Invitrogen, Carlsbad, Calif.; catalog #31985088) with 1% FBS. 5 uL of test compound diluted in Opti-MEM supplemented with 1% BSA was transferred to each well of the Optiplate. The plates were then incubated at 37° C./5% $CO_2$ for two h. 12 μL of substrate prepared from the PathHunter Flash Detection Kit (DiscoveRx, Fremont, Calif.: catalog #93-0001) was transferred to each well of the Optiplate. The plate was then incubated in the dark at room temperature for 2 h, after which the assay plate was read.

Assay Readout:

β-Arrestin assay readout was accomplished using a PHERAstar (BMG LABTECII Inc., Durham, N.C.) or EnVision™ (PerkinElmer, Fremont Calif.) microplate reader.

The $EC_{50}$ value for $hCB_1$ was observed to be substantially inactive and the $EC_{50}$ value observed for $hCB_2$ for Compound 1 is shown in the following Table. Compound 1 is a selective agonist for $CR_2$.

| | $EC_{50}$ $hCB_2$ (nM) |
|---|---|
| Compound 1 | 5.4 |

Example 9: Effect of Compound 1 on Osteoarthritis Pain

Injection of monosodium iodoacetate (MIA) into a joint (Kalbhen D. A., *J. Rheumatol.*, 1987, May; 14 Spec No:130-1; Combe, R., et. al., *Neuroscience Letters*, 2004, 370, 236-240) inhibits the activity of glyceraldehyde-3-phosphate dehydrogenase in chondrocytes, resulting in disruption of glycolysis and eventually in cell death. The progressive loss of chondrocytes results in histological and morphological changes of the articular cartilage, closely resembling those seen in osteoarthritis patients.

The osteoarthritis was induced in 200 g male Sprague Dawley rats. After brief anaesthesia by isoflurane rats received a single intra-articular injection of MIA (2 mg) (Sigma Aldrich, Saint Louis, Mo., USA; Cat #19148) dissolved in 0.9% sterile saline in a 50 μL volume administered through the patella ligament into the joint space of the left knee with a 30 G needle. Following the injection, animals were allowed to recover from anaesthesia before being returned to the main housing vivarium.

Typically during disease progression, there was an inflammation period of 0-7 days post-intra-articular injection followed by progressive degeneration of the cartilage and subchondral bone from days 14-55. Efficacy studies with a compound of the present invention for pain development took place from day 14 onwards and were performed twice a week with at least 3 days' wash-out in between each assay. Three different assays were used to measure pain. Tactile allodynia was measured via von Frey assay, hind limb paw weight distribution was monitored using an incapacitence tester (Columbus Instruments, Columbus, Ohio, USA) and hind limb grip strength was measured using a grip strength meter (Columbus Instruments, Columbus, Ohio, USA). Briefly, the von Frey assay was performed using the standard up down method with von-Frey filaments. Hind paw weight distribution was determined by placing rats in a chamber so that each hind paw rests on a separate force plate of the incapacitence tester. The force exerted by each hind limb (measured in grams) is averaged over a 3 second period. Three measurements were taken for each rat, and the change in hind paw weight distribution calculated. Peak hind limb grip force was conducted by recoding the maximum compressive force exerted on the hind limb mesh gauge set on the grip strength meter. During the testing, each rat was restrained and the paw of the injected knee was allowed to grip the mesh. The animal was then pulled in an upward motion until their grip was broken. Each rat is tested 3 times, with the contralateral paw used as a control.

Figure 18:
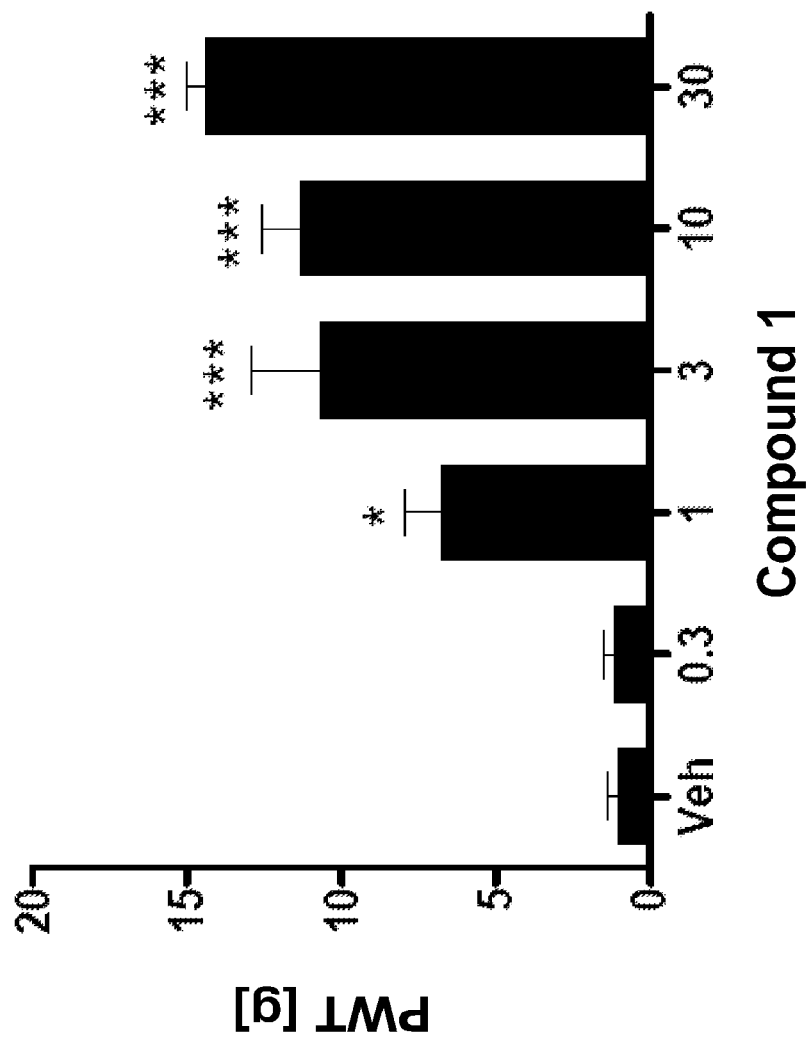
FIG. 18 shows the effect of Compound 1 in the monosodium iodoacetate (MIA) model of osteoarthritis in rats, see Example 9.

Animals were base-lined prior to treatment of the test compound. The MIA treated groups of rats (6 per group) were then dosed with either vehicle (0.5% methylcellulose, orally), Compound 1 (at 3 mg/kg, 10 mg/kg, and 30 mg/kg, orally). Dosing volume was 500 µL. One hour after dosing, von Frey assay, hind limb weight distribution and/or hind limb grip analysis was performed to measure the efficacy of the test compound. Increase in paw withdrawal threshold (PWT) by Compound 1 in comparison with vehicle shown in FIG. 18 was indicative of the test compound exhibiting therapeutic efficacy in the MIA model of osteoarthritis.

Example 10: Powder X-ray Diffraction

Powder X-ray Diffraction (PXRD) data were collected on an X'Pert PRO MPD powder diffractometer (PANalytical, Inc.) with a Cu source set at 45 kV and 40 mA, Cu(Kα) radiation and an X'Celerator detector. Samples were added to the sample holder and smoothed flat with a spatula and weigh paper. With the samples spinning, X-ray diffractograms were obtained by a 12-min scan over the 2-theta range 5-40°2θ. Diffraction data were viewed and analyzed with the X'Pert Data Viewer Software, version 1.0a and X'Pert HighScore Software, version 1.0b.

Example 11: Differential Scanning Calorimetry

Differential scanning calorimetry (DSC) studies were conducted using a TA Instruments, Q2000 at a heating rate 10° C./min. The instruments were calibrated for temperature and energy using the melting point and enthalpy of fusion of an indium standard. Thermal events (desolvation, melting, etc.) were evaluated using Universal Analysis 2000 software, version 4.1D, Build 4.1.0.16.

Example 12: Thermal Gravimetric Analysis

Thermogravimetric analyses (TGA) were conducted using a TA Instruments TGA Q500 or Q5000 at a heating rate 10° C./min. The instruments were calibrated using a standard weight for the balance, and Alumel and Nickel standards for the furnace (Curie point measurements). Thermal events such as weight-loss are calculated using the Universal Analysis 2000 software, version 4.1D, Build 4.1.0.16.

Example 13: Dynamic Moisture-Sorption Analysis

A dynamic moisture-sorption (DMS) study was conducted using a dynamic moisture-sorption analyzer, VTI Corporation, SGA-100. The instrument was calibrated using polyvinyl pyrrolidone (PVP) and NaCl. Samples were prepared for DMS analysis by placing 5 mg to 20 mg of a sample in a tared sample holder. The sample was placed on the hang-down wire of the VTI balance. A drying step was run, typically at 40° C. and 0.5-1% RH for 1 h. The isotherm temperature is 25° C. Defined % RH holds typically ranged from 10% RH to 90% RH, with intervals of 10 to 20% RH. A Δ % weight change smaller than 0.010% over 10 min, or up to 2 h, whichever occurred first, was required before continuing to the next % RH hold. The water content of the sample equilibrated as described above was determined at each % RH hold.

Figure 7A:
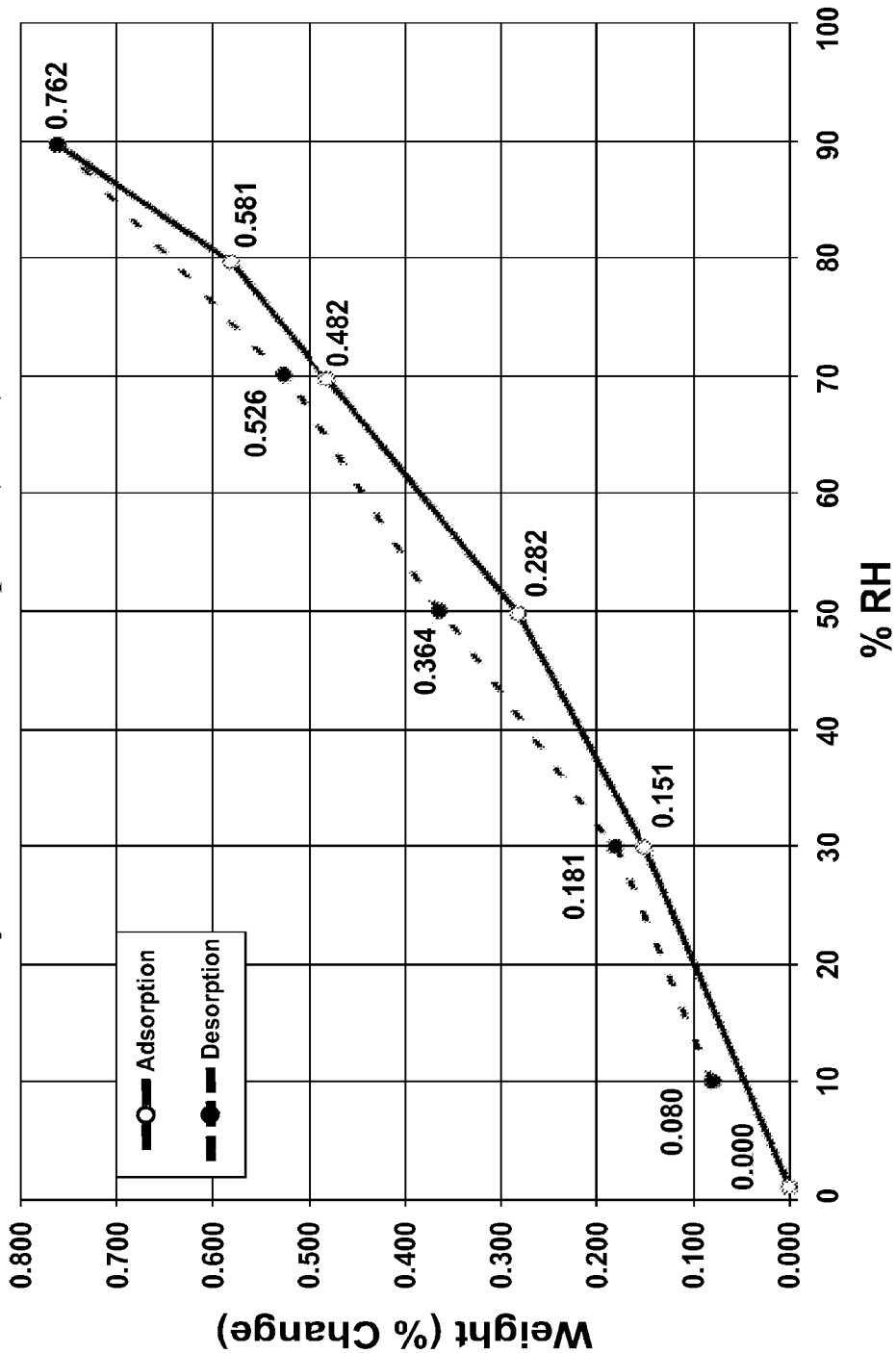
FIG. 7A shows an adsorption and desorption isotherm, Dyanmic Moisture Sorption (DMS), for a sample containing anhydrous crystalline form of Compound 1.

The DMS profile (adsorption/desorption isotherm) for the anhydrous crystalline form of Compound 1 is shown in FIG. 7A. The corresponding data in tabular form is provided below:

| Elapsed Time (min) | Weight (mg) | Weight (% Change) | Sample Temperature | Sample RH (%) |
|---|---|---|---|---|
| 46.6 | 9.6782 | 0 | 25.46 | 1.1 |
| 71.4 | 9.6928 | 0.151 | 25.32 | 29.94 |
| 91.1 | 9.7055 | 0.282 | 25.31 | 49.86 |
| 111.2 | 9.7248 | 0.482 | 25.3 | 69.77 |
| 129.1 | 9.7344 | 0.581 | 25.29 | 79.70 |
| 160.1 | 9.7519 | 0.762 | 25.3 | 89.72 |
| 180.1 | 9.7291 | 0.526 | 25.30 | 70.11 |
| 200.1 | 9.7134 | 0.364 | 25.3 | 50.07 |
| 218.6 | 9.6957 | 0.181 | 25.29 | 29.99 |
| 234.4 | 9.6859 | 0.080 | 25.29 | 10.06 |

Those skilled in the art will recognize that various modifications, additions, substitutions, and variations to the illustrative examples set forth herein can be made without departing from the spirit of the invention and are, therefore, considered within the scope of the invention.

What is claimed is:

1. A solvate selected from the group consisting of:
   an acetone solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide;
   a non-selective solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; and
   an ethyl acetate solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

2. A composition comprising a solvate according to claim 1.

3. The solvate of claim 1, which is an acetone solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

4. The solvate of claim 1, which is a non-selective solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

5. The solvate of claim 1, which is an ethyl acetate solvate of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

6. A composition comprising the acetone solvate according to claim 3.

7. A composition comprising the non-selective solvate according to claim 4.

8. A composition comprising the ethyl acetate solvate according to claim 5.

9. A method for the treatment of pain in an individual, comprising administering to said individual in need thereof a therapeutically effective amount of the acetone solvate according to claim 3.

10. A method for the treatment of pain in an individual, comprising administering to said individual in need thereof a therapeutically effective amount of the non-selective solvate according to claim 4.

11. A method for the treatment of pain in an individual, comprising administering to said individual in need thereof a therapeutically effective amount of the ethyl acetate solvate according to claim 5.

* * * * *